US012723328B2

(12) United States Patent
Bertoletti et al.

(10) Patent No.: US 12,723,328 B2
(45) Date of Patent: Sep. 1, 2026

(54) HBV SPECIFIC TCR LIBRARY AND ITS USE AS PERSONALISED MEDICINE

(71) Applicant: LION TCR PTE. LTD., Singapore (SG)

(72) Inventors: Antonio Bertoletti, Singapore (SG); Zi Zong Ho, Singapore (SG); Sarene Koh, Singapore (SG); Anthony Tanoto Tan, Singapore (SG); Lu-En Wai, Singapore (SG)

(73) Assignee: LION TCR PTE. LTD., Singapore (SG)

( * ) Notice: Subject to any disclaimer, the term of this patent is extended or adjusted under 35 U.S.C. 154(b) by 986 days.

(21) Appl. No.: 17/794,379

(22) PCT Filed: Jan. 21, 2021

(86) PCT No.: PCT/EP2021/051356
§ 371 (c)(1),
(2) Date: Jul. 21, 2022

(87) PCT Pub. No.: WO2021/148547
PCT Pub. Date: Jul. 29, 2021

(65) Prior Publication Data

US 2023/0061817 A1 Mar. 2, 2023

(30) Foreign Application Priority Data

Jan. 21, 2020 (WO) ................. PCT/EP2020/051439

(51) Int. Cl.
*C40B 40/10* (2006.01)
*A61K 40/32* (2025.01)
*C07K 14/705* (2006.01)

(52) U.S. Cl.
CPC .............. *C40B 40/10* (2013.01); *A61K 40/32* (2025.01); *C07K 14/7051* (2013.01)

(58) Field of Classification Search
None
See application file for complete search history.

(56) References Cited

U.S. PATENT DOCUMENTS

2011/0070208 A1* 3/2011 Bertoletti ............... A61K 40/46
435/325

FOREIGN PATENT DOCUMENTS

| | | | |
|---|---|---|---|
| WO | 2009/136874 | A1 | 11/2009 |
| WO | 2014/090985 | A1 | 6/2014 |
| WO | 2016/138278 | A2 | 9/2016 |
| WO | 2017/120428 | A1 | 7/2017 |
| WO | 2017/120428 | A2 | 7/2017 |
| WO | 2017/171631 | A1 | 10/2017 |
| WO | 2017/194555 | A1 | 11/2017 |
| WO | 2018/056897 | A1 | 3/2018 |
| WO | 2019/004939 | A1 | 1/2019 |

OTHER PUBLICATIONS

Glanville, Jacob, et al., "Identifying specificity groups in the T cell receptor repertoire", Nature Jul. 6, 2017; vol. 547, No. 7661, pp. 94-98. doi:10.1038/nature22976.
Wagner, Ellen K., et al., "Human cytomegalovirus-specific T cell receptor engineered for high affinity and soluble expression using mammalian cell display", Journal of Biological Chemistry (2019) vol. 15, pp. 5790-5804. doi: 10.1074/jbcRA118.007187.
International Search Report and Written Opinion issued for Application No. PCT/EP2021/051356, dated May 21, 2021. 18 pages.
International Search Report and Written Opinion issued for Application No. PCT/EP2020/051439, dated Oct. 28, 2020. 12 pages.
Tan, Anthony Tanoto, et al., "Use of Expression Profiles of HBV-DNA Integrated Into Genomes of Hepatocellular Carcinoma Cells to Select T Cells for Immunotherapy", Gastroenterology, vol. 156, No. 6, May 1, 2019, pp. 1862-1876.e9, XP055738219, DOI:10.1053/j.gastro.2019.01.251.
Banu, Nasirah, et al., "Building and optimizing a virus-specific T cell receptor library for targeted immunotherapy in viral infections" Scientific Reports 4: 4166, pp. 1-10 (2014). XP055533461, DOI: 10.1038/srep04166.
Changhua, Ji, et al., "Targeted delivery of interferon-a to hepatitis B virus-infected cells using T-cell receptor-like antibodies" Hepatology 56 (2012): 2027-2038.
Thakkar, Neerja, et al., "Balancing sensitivity and specificity in distinguishing TCR groups by CDR sequence similarity" BMC Bioinformatics 20.1 (2019): 241, 1-14.
Smith, Sheena, N., et al., "Changing the peptide specificity of a human T-cell receptor by directed evolution." Nature Communications 5:5223 (2014): 1-13, DOI: 10.1038/ncomms6223.
Jon Cohen, "Forgotten No. More—A long-overlooked scourge of millions, hepatitis B is in the crosshairs at last." Science 362, 2018, 984-987.
Walseng, Even, et al., "Soluble T-Cell Receptors Produced in Human Cells for Targeted Delivery" PLOS One 10(4) (2015): DOI:10.1371/journal.pone.0119559 Apr. 13, 2015.
Sastry, Konduru, S.R., et al. "Targeting hepatitis B virus-infected cells with a T-cell receptor-like antibody." Journal of Virology 85.5 (2011): 1935-1942.
Walseng, Even, et al.,"A TCR-based chimeric antigen receptor" Scientific Reports 7.1 (2017): 10713, 1-10, DOI:10.1038/s41598-017-11126-y.
Wei, Xiaohua, et al., "Patterns of HLA Class I Gene Expression", extract from Encyclopedia of Immunology (Second Edition), 1998.

* cited by examiner

*Primary Examiner* — Christian C Boesen
(74) *Attorney, Agent, or Firm* — Meunier Carlin & Curfman LLC

(57) ABSTRACT

The invention provides T cell receptors (TCRs) that bind Hepatitis B virus (HBV) antigens. The present invention also provides methods of producing, screening and selecting the TCRs, therapeutic applications of the TCRs, and libraries of the TCRs.

6 Claims, No Drawings

Specification includes a Sequence Listing.

HBV SPECIFIC TCR LIBRARY AND ITS USE AS PERSONALISED MEDICINE

FIELD OF THE INVENTION

The present invention relates to T cell receptors (TCRs) that have potential for treating Hepatitis B virus (HBV) related diseases. The present invention also relates to methods of producing, screening and selecting the TCRs, therapeutic applications of the TCRs, and libraries of the TCRs.

BACKGROUND

The host immune system acts through T cells to combat viral infection and to keep host cancerous growth in check. Particularly in Hepatitis B virus infection, CD8+ T cells are an important component of the immune system to clear or control viral infections. Patients that resolve the infection have quantitatively stronger CD8+ immune responses compared to chronically infected patients. Conversely, lack of a virus-specific T cell response is associated with failure to control chronic HBV infection. Reconstitution of virus-specific immunity, either through bone marrow transplant or adoptive transfer of virus-specific T cells can control persistent infection, and protect against lethal infection.

External pathogens, such as viruses, can be processed into short peptides and presented by specialized antigen presenting molecules of the 'major histocompatibility complex' (MHC), e.g. human leukocyte antigen (HLA) molecules, on the surface of antigen presenting cells (APCs). There are two main classes of MHC, namely MHC class I and MHC class II. MHC class I molecules (HLA class I in humans) can be expressed by almost all cell types and typically act to present peptide antigens originating from the cytosolic compartment of the cell. This includes the presentation of peptides derived from viral proteins in virus infected cells. In contrast, MHC class II molecules (HLA class II in humans) are expressed by specialized APCs and typically present antigens originating outside the cell that have been endocytosed and processed in the endosomes/lysosomes.

T cell receptors (TCRs) expressed on CD8+ T cells can bind to antigens presented by specific HLA class I molecules on infected cells, which are acting as APCs. Thereafter, the TCRs initiate a series of cellular changes to lyse the infected cells. Strategies to manipulate the T cell response via virus-specific TCRs can provide clinical therapies to treat chronic infections and/or to prevent mortality related to further complications caused by prolonged infections. In particular, hepatocellular carcinoma (HCC) cells often have HBV DNA integration and can be targeted by HBV-specific T cells.

Humans have three major MHC class I genes, which are HLA-A, HLA-B and HLA-C. These three genes respectively express HLA-A, HLA-B and HLA-C molecules in virtually all nucleated human cells (Wei & Orr, 1998, which is hereby specifically incorporated by reference in its entirety).

The HLA class I molecules exhibit polymorphism, meaning that different allelic forms of HLA-A, B and C can be found in different individuals. Conventionally, the study of HBV antigen presentation has focused on HLA-A2 molecules, which present epitopes from the HBV genotypes A, D, and F that are dominant in western populations. By contrast, there has been limited information regarding HLA-B or C-mediated antigen presentation of HBV genotypes B and C that are dominant in Asian populations. Against this background of limited scientific research, HBV infections are widespread across the world, with more than 250 million people being thought to live with HBV infections (Ian Graber-Stiehl, Nature, 2018, which is hereby specifically incorporated by reference in its entirety) causing nearly 900,000 deaths per year from HBV-related cancer or liver cirrhosis (Cohen, Science, 2018, which is hereby specifically incorporated by reference in its entirety). There is a need for further HBV treatments.

SUMMARY OF THE INVENTION

The present inventors have developed a library of TCRs. The library comprises a plurality of TCRs that can be used to target HBV related diseases in individuals that express a broad range of MHC class I molecules. The library includes novel TCRs that bind human MHC class I molecules from all three of the major HLA class I types; HLA-A, HLA-B and HLA-C. A patient can be treated with a T cell expressing a TCR from the library if any of the patient's HLA-A, B and/or C haplotypes can be bound by a TCR from the library. Thus, for a library containing a relatively low number of TCRs, a comparatively broad group of human patients, including those expressing one (or more) of the HLA molecules listed herein, can be selected for a treatment involving a TCR selected from the library of the present invention. The inventors calculate that the 26 TCRs of the present disclosure provide avenues for treating a surprisingly high proportion of human populations. For instance, the proportion of the following populations that have a matching HLA class I molecule is as follows:

Southeast Asia 90%; Northeast Asia 84%; North America 80%; Europe 78%; East Asia 84%. In other words, over three quarters of these populations should be amenable to treatment with a TCR selected from the library of the invention.

A TCR taken from the library can be used in the treatment of a hepatitis patient, an HCC patient, an HBV infected patient, or a patient with an HBV-related infection such as HDV, wherein the patient has been selected according to the disclosed methods. Moreover, the inventors have shown that production and presentation of HBV-specific CD8 T-cell epitopes can take place in naturally HBV serologically negative HCC cells with HBV integration (Tan et al 2019, which is specifically incorporated by reference in its entirety), so that HCC patients selected according to the disclosed methods are also amenable to a treatment involving a TCR taken from the library, even if they are serologically HBV negative.

Accordingly, in some aspects, the invention provides a library of T cell receptors (TCRs), wherein the library includes one or more TCRs as disclosed herein.

The skilled person will appreciate that the number of TCRs in the library is preferably more than one. Thus, in some embodiments, the library of TCRs includes two or more TCRs disclosed herein. In some embodiments, the library includes three or more TCRs disclosed herein. In some embodiments, the library includes four or more TCRs disclosed herein. In some embodiments, the library includes five or more TCRs disclosed herein. In some embodiments, the library includes six or more, seven or more, eight or more, or nine or more TCRs disclosed herein. In some embodiments, the library includes ten or more TCRs disclosed herein. In some embodiments, the library includes more than ten TCRs disclosed herein, for instance 11 or more, 12 or more, 13 or more, 14 or more, 15 or more, 16 or more, 17 or more, 18 or more, 19 or more, 20 or more, 21 or more, 22 or more, 23 or more, 24 or more, 25, or all 26 of the TCRs disclosed herein.

The library can be termed a 'virus specific library' or an 'HBV specific library', but the skilled person will appreciate that, besides treating HBV infections, the TCR libraries of the invention can also be used in related clinical applications such as for use in the treatment of other diseases such as HCC, HDV and liver cirrhosis, which commonly have an HBV infection as an underlying cause.

The library can be defined in whole, or in part, by the MHC restriction of the TCRs of the library. In some embodiments, the TCR library will include, or exclude, one or more TCRs that are restricted to a particular HLA class, a particular HLA subclass, or a particular haplotype. For instance, in some embodiments the TCR library includes one or more TCRs that are restricted to an HLA-A molecule. This HLA-A molecule may be of subclass HLA-A*11. In some embodiments the TCR library includes one or more TCRs that are restricted to HLA-A*1101. In some embodiments the TCR library includes one or more TCRs that are restricted to HLA-A*1102. The HLA-A molecule may be of subclass HLA-A*68. In some embodiments the TCR library includes one or more TCRs that are restricted to HLA-A*6802. The HLA-A molecule may be of subclass HLA-A*24. In some embodiments the TCR library includes one or more TCRs that are restricted to HLA-A*2401. In some embodiments the TCR library includes one or more TCRs that are restricted to HLA-A*2402. In some embodiments the TCR library includes one or more TCRs that are restricted to HLA-A*2407. In some embodiments, the TCR library excludes TCRs that are restricted to certain HLA-A molecules. For instance, the TCR library may exclude TCRs that are restricted to HLA-A*02, such as HLA-A*0201. In some embodiments, the TCR library may exclude TCRs that are restricted to HLA-A molecules besides HLA-A molecules of subclass HLA-A*11, or the TCR library may exclude TCRs that are restricted to HLA-A molecules besides HLA-A molecules of subclass HLA-A*11, HLA-A*68, and/or HLA-A*24.

In some embodiments the TCR library includes one or more TCRs that are restricted to an HLA-B molecule. This HLA-B molecule may be of subclass HLA-B*58. In some embodiments the TCR library includes one or more TCRs that are restricted to HLA-B*5801. The HLA-B molecule may be of subclass HLA-B*07. In some embodiments the TCR library includes one or more TCRs that are restricted to HLA-B*0706. The HLA-B molecule may be of subclass HLA-B*39. In some embodiments the TCR library includes one or more TCRs that are restricted to HLA-B*3915. The HLA-B molecule may be of subclass HLA-B*40. In some embodiments the TCR library includes one or more TCRs that are restricted to HLA-B*4001. In some embodiments the TCR library includes one or more TCRs that are restricted to HLA-B*4040. The HLA-B molecule may be of subclass HLA-B*15. In some embodiments the TCR library includes one or more TCRs that are restricted to HLA-B*1510. The HLA-B molecule may be of subclass HLA-B*44. In some embodiments the TCR library includes one or more TCRs that are restricted to HLA-B*4403. The HLA-B molecule may be of subclass HLA-B*35. In some embodiments the TCR library includes one or more TCRs that are restricted to HLA-B*3501. In some embodiments the TCR library includes one or more TCRs that are restricted to HLA-B*3503. The HLA-B molecule may be of subclass HLA-B*55. In some embodiments the TCR library includes one or more TCRs that are restricted to HLA-B*5502. In some embodiments, the TCR library excludes TCRs that are restricted to certain HLA-B molecules. For instance, the TCR library may exclude TCRs that are restricted to HLA-B*58, such as HLA-B*5801. In some embodiments the TCR library may exclude TCRs that are restricted to HLA-B molecules besides HLA-B molecules of subclass HLA-B*58, HLA-B*07, HLA-B*39, HLA-B*40, HLA-B*15, HLA-B*44, HLA-B*35, and/or HLA-B*55.

In some embodiments the TCR library includes one or more TCRs that are restricted to an HLA-C molecule. This HLA-C molecule may be of subclass HLA-C*03. In some embodiments the TCR library includes one or more TCRs that are restricted to HLA-C*0302. The HLA-C molecule may be of subclass HLA-C*08. In some embodiments the TCR library includes one or more TCRs that are restricted to HLA-C*0822. The HLA-C molecule may be of subclass HLA-C*07. In some embodiments the TCR library includes one or more TCRs that are restricted to HLA-C*0706. The HLA-C molecule may be of subclass HLA-C*12. In some embodiments the TCR library includes one or more TCRs that are restricted to HLA-C*1202. In some embodiments the TCR library includes one or more TCRs that are restricted to HLA-C*1203. In some embodiments, the TCR library excludes TCRs that are restricted to certain HLA-C molecules. For instance, the TCR library may exclude TCRs that are restricted to HLA-C*0801. In some embodiments, the TCR library may exclude TCRs that are restricted to HLA-C molecules besides HLA-C molecules of subclass HLA-C*03, C*08, HLA-C*07 and/or HLA-C*12.

In some embodiments, the TCR library will include two or more TCRs, three or more, four or more, five or more, or six or more TCRs that are restricted to an HLA molecule defined herein.

The TCRs of the present invention are αβ-TCRs (from αβ-T cells). The skilled person knows that αβ-TCRs have an α-chain and a β-chain. The α-chain has three complementarity determining region (CDR) sequences, numbered CDR1a, CDR2a and CDR3a. The β-chain has three CDRs, numbered CDR1 b, CDR2b and CDR3b. The TCRs and functional fragments of the invention will include an α-chain and a β-chain (although in some embodiments, the α-chain and a β-chain may be conjugated together, e.g. as a fusion). The CDR3 sequences are most important for determining the target that is bound by a TCR (Thakkar and Bailey-Kellogg, BMC Bioinformatics 2019).

In some embodiments of the invention, the TCR library comprises one or more of the TCRs defined herein by their complementarity determining region (CDR) sequences. For instance, the TCR library of the invention may include one or more TCRs having a CDR3 sequence selected from the following list:

```
                        (SEQ ID NO: 1)
AETLDNYGQNFV,

                       (SEQ ID NO: 23)
ASSLSAAYEQY,

                       (SEQ ID NO: 19)
ASSNRASSYNEQF,

                       (SEQ ID NO: 20)
ASSSDFGNQPQH,

                        (SEQ ID NO: 2)
ATWLSGSARQLTF,

                        (SEQ ID NO: 3)
AVNLYAGNMLT,

                        (SEQ ID NO: 6)
AVSDNQGGKLI,
```

-continued (SEQ ID NO: 16) CAESMGDFNKFYF, (SEQ ID NO: 13) CAGAGYGGSQGNLIF, (SEQ ID NO: 25) CASEMAGGGDNYGYTF, (SEQ ID NO: 34) CASSASLADNTGELFF, (SEQ ID NO: 26) CASSFSGKASYYEQYF, (SEQ ID NO: 30) CASSIAGGAEQYF, (SEQ ID NO: 22) CASSLELAGPWGNEQFF, (SEQ ID NO: 21) CASSLFKGADTQYF, (SEQ ID NO: 31) CASSLSYRGLGEQFF, (SEQ ID NO: 28) CASSPDSSGANVLTF, (SEQ ID NO: 27) CASSPEPTSGSFNEQFF, (SEQ ID NO: 33) CASSPGEGNQPQHF, (SEQ ID NO: 32) CASSSRQGGTYEQYF, (SEQ ID NO: 12) CAVDGNNRLAF, (SEQ ID NO: 11) CAVNMVAGNMLTF, (SEQ ID NO: 10) CAVRDQTGANNLFF, (SEQ ID NO: 7) CAVRYNNARLMF, (SEQ ID NO: 17) CAVSTNFGNEKLTF, (SEQ ID NO: 15) CAVYHTGFQKLVF, (SEQ ID NO: 14) CAYIGNAGNMLTF, (SEQ ID NO: 5) CAYRSGLNNDMRF, (SEQ ID NO: 4) CGADRGGGKLIF, (SEQ ID NO: 9) CLVGDEDTGRRALTF, (SEQ ID NO: 24) CSAPAGMGYEQYF, (SEQ ID NO: 29) CSVDMDWGIGGYTF, (SEQ ID NO: 8) CVVNGVDSSYKLIF, (SEQ ID NO: 18) SAVDRDEPFHSNQPQH, -continued (SEQ ID NO: 151) CAESTGGSYIPTF, (SEQ ID NO: 160) CASASDSDDEKLFF, (SEQ ID NO: 152) CAVNAPGGYNKLIF, (SEQ ID NO: 161) CASSISQGGYGYTF, (SEQ ID NO: 153) CAVERPTGGYNKLIF, (SEQ ID NO: 162) CASSPGTDYEQYF, (SEQ ID NO: 154) CAVEDYGQNFVF, (SEQ ID NO: 163) CSARDLSGRSLDTQYF, (SEQ ID NO: 155) CALSDSSGGSYIPTF, (SEQ ID NO: 164) CASSLGRQTNTEAFF, (SEQ ID NO: 156) CAACYSGYALNF, (SEQ ID NO: 165) CASSYRPKLDTEAFF, (SEQ ID NO: 157) CAVVTNDYKLSF, (SEQ ID NO: 166) CASSQDLGQGSDTQYF, (SEQ ID NO: 158) CAMRSFAQAGTALIF, (SEQ ID NO: 167) CASSQRGKGQGDEETQYF, (SEQ ID NO: 159) CAGWISPQGAQKLVF, (SEQ ID NO: 168) CASSLSTNTEAFF.

The TCRs of the libraries of the invention may be defined by both their CDR3a and CDR3b sequences. For instance, in some embodiments the library includes one or more TCRs that have a CDR3a/CDR3b pairing as set forth Table 1:

TABLE 1

| CDR3a/CDR3b pairs | | |
|---|---|---|
| TCR | CDR3a | CDR3b |
| 1 | AETLDNYGQNFV (SEQ ID NO: 1) | SAVDRDEPFHSNQPQH (SEQ ID NO: 18) |
| 2 | ATWLSGSARQLTF (SEQ ID NO: 2) | ASSNRASSYNEQF (SEQ ID NO: 19) |
| 3 | AVNLYAGNMLT (SEQ ID NO: 3) | ASSSDFGNQPQH (SEQ ID NO: 20) |
| 4 | CGADRGGGKLIF (SEQ ID NO: 4) | CASSLFKGADTQYF (SEQ ID NO: 21) |
| 5 | CAYRSGLNNDMRF (SEQ ID NO: 5) | CASSLELAGPWGNEQFF (SEQ ID NO: 22) |

TABLE 1-continued

| CDR3a/CDR3b pairs | | |
|---|---|---|
| TCR | CDR3a | CDR3b |
| 6 | AVSDNQGGKLI (SEQ ID NO: 6) | ASSLSAAYEQY (SEQ ID NO: 23) |
| 7 | CAVRYNNARLMF (SEQ ID NO: 7) | CSAPAGMGYEQYF (SEQ ID NO: 24) |
| 8 | CVVNGVDSSYKLIF (SEQ ID NO: 8) | CASEMAGGGDNYGYTF (SEQ ID NO: 25) |
| 9 | CLVGDEDTGRRALTF (SEQ ID NO: 9) | CASSFSGKASYYEQYF (SEQ ID NO: 26) |
| 10 | CAVRDQTGANNLFF (SEQ ID NO: 10) | CASSPEPTSGSFNEQFF (SEQ ID NO: 27) |
| 11 | CAVNMVAGNMLTF (SEQ ID NO: 11) | CASSPDSSGANVLTF (SEQ ID NO: 28) |
| 12 | CAVDGNNRLAF (SEQ ID NO: 12) | CSVDMDWGIGGYTF (SEQ ID NO: 29) |
| 13 | CAGAGYGGSQGNLIF (SEQ ID NO: 13) | CASSIAGGAEQYF (SEQ ID NO: 30) |
| 14 | CAYIGNAGNMLTF (SEQ ID NO: 14) | CASSLSYRGLGEQFF (SEQ ID NO: 31) |
| 15 | CAVYHTGFQKLVF (SEQ ID NO: 15) | CASSSRQGGTYEQYF (SEQ ID NO: 32) |
| 16 | CAESMGDFNKFYF (SEQ ID NO: 16) | CASSPGEGNQPQHF (SEQ ID NO: 33) |
| 17 | CAVSTNFGNEKLTF (SEQ ID NO: 17) | CASSASLADNTGELFF (SEQ ID NO: 34) |
| 18 | CAESTGGSYIPTF (SEQ ID NO: 151) | CASASDSDDEKLFF (SEQ ID NQ: 160) |
| 19 | CAVNAPGGYNKLIF (SEQ ID NO: 152) | CASSISQGGYGYTF (SEQ ID NO: 161) |
| 20 | CAVERPTGGYNKLIF (SEQ ID NO: 153) | CASSPGTDYEQYF (SEQ ID NO: 162) |
| 21 | CAVEDYGQNFVF (SEQ ID NO: 154) | CSARDLSGRSLDTQYF (SEQ ID NO: 163) |
| 22 | CALSDSSGGSYIPTF (SEQ ID NO: 155) | CASSLGRQTNTEAFF (SEQ ID NO: 164) |
| 23 | CAACYSGYALNF (SEQ ID NO: 156) | CASSYRPKLDTEAFF (SEQ ID NO: 165) |
| 24 | CAVVTNDYKLSF (SEQ ID NO: 157) | CASSQDLGQGSDTQYF (SEQ ID NO: 166) |
| 25 | CAMRSFAQAGTALIF (SEQ ID NO: 158) | CASSQRGKGQGDEETQYF (SEQ ID NO: 167) |
| 26 | CAGWISPQGAQKLVF (SEQ ID NO: 159) | CASSLSTNTEAFF (SEQ ID NO: 168) |

The TCRs of the invention may be defined by several CDR sequences. For instance, TCR1 may be defined as comprising an α-chain having the following CDRs:

i) CDR1a: (SEQ ID NO: 58)
DSSSTY;

ii) CDR2a: (SEQ ID NO: 35)
IFSNMDM;

and/or iii) CDR3a: (SEQ ID NO: 1)
AETLDNYGQNFV;

and/or as comprising a β-chain having the following CDRs:

iv) CDR1b: (SEQ ID NO: 72)
DFQATT;

v) CDR2b: (SEQ ID NO: 47)
SNEGSKA;

and/or vi) CDR3b: (SEQ ID NO: 18)
SAVDRDEPFHSNQPQH.

Exemplary sets of CDRs for 17 TCRs are presented in Table 2, below.

TABLE 2

| Exemplary CDR sets for TCRs 1-26 | | | |
|---|---|---|---|
| TCR, a/b chain | CDR1 | CDR2 | CDR3 |
| TCR1, α | DSSSTY (SEQ ID NO: 58) | IFSNMDM (SEQ ID NO: 35) | AETLDNYGQNFV (SEQ ID NO: 1) |
| TCR1, β | DFQATT (SEQ ID NO: 72) | SNEGSKA (SEQ ID NO: 47) | SAVDRDEPFHSNQPQH (SEQ ID NO: 18) |
| TCR2, α | TSINN (SEQ ID NO: 59) | IRSNERE (SEQ ID NO: 36) | ATWLSGSARQLTF (SEQ ID NO: 2) |
| TCR2, β | SGHDY (SEQ ID NO: 73) | FNNNVP (SEQ ID NO: 48) | ASSNRASSYNEQF (SEQ ID NO: 19) |

TABLE 2-continued

Exemplary CDR sets for TCRs 1-26

| TCR, a/b chain | CDR1 | CDR2 | CDR3 |
|---|---|---|---|
| TCR3, α | DRGSQS (SEQ ID NO: 60) | IYSNGD (SEQ ID NO: 37) | AVNLYAGNMLT (SEQ ID NO: 3) |
| TCR3, β | SGHVS (SEQ ID NO: 74) | FQNEAQ (SEQ ID NO: 49) | ASSSDFGNQPQH (SEQ ID NO: 20) |
| TCR4, α | KTLYG (SEQ ID NO: 61) | LQKGGEE (SEQ ID NO: 38) | CGADRGGGKLIF (SEQ ID NO: 4) |
| TCR4, β | MDHEN (SEQ ID NO: 75) | SYDVKM (SEQ ID NO: 50) | CASSLFKGADTQYF (SEQ ID NO: 21) |
| TCR5, α | TSESDYY (SEQ ID NO: 62) | QEAYKQQN (SEQ ID NO: 39) | CAYRSGLNNDMRF (SEQ ID NO: 5) |
| TCR5, β | SGHAT (SEQ ID NO: 76) | FQNNGV (SEQ ID NO: 51) | CASSLELAGPWGNEQFF (SEQ ID NO: 22) |
| TCR6, α | SSVSVY (SEQ ID NO: 63) | YLSGSTLV (SEQ ID NO: 40) | AVSDNQGGKLI (SEQ ID NO: 6) |
| TCR6, β | SGHNS (SEQ ID NO: 77) | FNNNVP (SEQ ID NO: 48) | ASSLSAAYEQY (SEQ ID NO: 23) |
| TCR7, α | TSGFNG (SEQ ID NO: 64) | NVLDGL (SEQ ID NO: 41) | CAVRYNNARLMF (SEQ ID NO: 7) |
| TCR7, β | DFQATT (SEQ ID NO: 72) | SNEGSKA (SEQ ID NO: 47) | CSAPAGMGYEQYF (SEQ ID NO: 24) |
| TCR8, α | NSASQS (SEQ ID NO: 65) | VYSSGN (SEQ ID NO: 42) | CVVNGVDSSYKLIF (SEQ ID NO: 8) |
| TCR8, β | MDHEN (SEQ ID NO: 75) | SYDVKM (SEQ ID NO: 50) | CASEMAGGGDNYGYTF (SEQ ID NO: 25) |
| TCR9, α | NIATNDY (SEQ ID NO: 66) | GYKTK (SEQ ID NO: 43) | CLVGDEDTGRRALTF (SEQ ID NO: 9) |
| TCR9, β | MNHEY (SEQ ID NO: 78) | SMNVEV (SEQ ID NO: 52) | CASSFSGKASYYEQYF (SEQ ID NO: 26) |
| TCR10, α | SVFSS (SEQ ID NO: 67) | WTGGEV (SEQ ID NO: 44) | CAVRDQTGANNLFF (SEQ ID NO: 10) |
| TCR10, β | LGHNA (SEQ ID NO: 79) | YNFKEQ (SEQ ID NO: 53) | CASSPEPTSGSFNEQFF (SEQ ID NO: 27) |
| TCR11, α | DRGSQS (SEQ ID NO: 60) | IYSNGD (SEQ ID NO: 37) | CAVNMVAGNMLTF (SEQ ID NO: 11) |
| TCR11, β | SGHTA (SEQ ID NO: 80) | FQGTGA (SEQ ID NO: 54) | CASSPDSSGANVLTF (SEQ ID NO: 28) |
| TCR12, α | DSVNN (SEQ ID NO: 68) | IPSGT (SEQ ID NO: 45) | CAVDGNNRLAF (SEQ ID NO: 12) |
| TCR12, β | SQVTM (SEQ ID NO: 81) | ANQGSEA (SEQ ID NO: 55) | CSVDMDWGIGGYTF (SEQ ID NO: 29) |
| TCR13, α | SVFSS (SEQ ID NO: 67) | WTGGEV (SEQ ID NO: 44) | CAGAGYGGSQGNLIF (SEQ ID NO: 13) |
| TCR13, β | LNHDA (SEQ ID NO: 82) | SQIVND (SEQ ID NO: 56) | CASSIAGGAEQYF (SEQ ID NO: 30) |
| TCR14, α | TSESDYY (SEQ ID NO: 62) | QEAYKQQN (SEQ ID NO: 39) | CAYIGNAGNMLTF (SEQ ID NO: 14) |
| TCR14, β | MNHEY (SEQ ID NO: 78) | SMNVEV (SEQ ID NO: 52) | CASSLSYRGLGEQFF (SEQ ID NO: 31) |
| TCR15, α | VSGLRG (SEQ ID NO: 69) | LYSAGEE (SEQ ID NO: 46) | CAVYHTGFQKLVF (SEQ ID NO: 15) |

TABLE 2-continued

Exemplary CDR sets for TCRs 1-26

| TCR, a/b chain | CDR1 | CDR2 | CDR3 |
|---|---|---|---|
| TCR15, β | MDHEN (SEQ ID NO: 75) | SYDVKM (SEQ ID NO: 50) | CASSSRQGGTYEQYF (SEQ ID NO: 32) |
| TCR16, α | DSSSTY (SEQ ID NO: 58) | IFSNMDM (SEQ ID NO: 35) | CAESMGDFNKFYF (SEQ ID NO: 16) |
| TCR16, β | MNHEY (SEQ ID NO: 78) | SMNVEV (SEQ ID NO: 52) | CASSPGEGNQPQHF (SEQ ID NO: 33) |
| TCR17, α | DRVSQS (SEQ ID NO: 70) | IYSNGD (SEQ ID NO: 37) | CAVSTNFGNEKLTF (SEQ ID NO: 17) |
| TCR17, β | SGDLS (SEQ ID NO: 83) | YYNGEE (SEQ ID NO: 57) | CASSASLADNTGELFF (SEQ ID NO: 34) |
| TCR18, α | DSSSTY (SEQ ID NO: 58) | IFSNMDM (SEQ ID NO: 35) | CAESTGGSYIPTF (SEQ ID NO: 151) |
| TCR18, β | SNHLY (SEQ ID NO: 187) | FYNNEI (SEQ ID NO: 175) | CASASDSDDEKLFF (SEQ ID NO: 160) |
| TCR19, α | YGGTVN (SEQ ID NO: 181) | TFSGDPLV (SEQ ID NO: 169) | CAVNAPGGYNKLIF (SEQ ID NO: 152) |
| TCR19, β | LNHDA (SEQ ID NO: 82) | SQIVND (SEQ ID NO: 56) | CASSISQGGYGYTF (SEQ ID NO: 161) |
| TCR20, α | DSVNN (SEQ ID NO: 68) | IPSGT (SEQ ID NO: 45) | CAVERPTGGYNKLIF (SEQ ID NO: 153) |
| TCR20, β | SGHRS (SEQ ID NO: 188) | YFSETQ (SEQ ID NO: 176) | CASSPGTDYEQYF (SEQ ID NO: 162) |
| TCR21, α | DSAIYN (SEQ ID NO: 182) | IQSSQRE (SEQ ID NO: 170) | CAVEDYGQNFVF (SEQ ID NO: 154) |
| TCR21, β | DFQATT (SEQ ID NO: 72) | SNEGSKA (SEQ ID NO: 47) | CSARDLSGRSLDTQYF (SEQ ID NO: 163) |
| TCR22, α | TRDTTYY (SEQ ID NO: 183) | RNSFDEQN (SEQ ID NO: 171) | CALSDSSGGSYIPTF (SEQ ID NO: 155) |
| TCR22, β | SEHNR (SEQ ID NO: 189) | FQNEAQ (SEQ ID NO: 49) | CASSLGRQTNTEAFF (SEQ ID NO: 164) |
| TCR23, α | DSASNY (SEQ ID NO: 184) | IRSNVGE (SEQ ID NO: 172) | CAACYSGYALNF (SEQ ID NO: 156) |
| TCR23, β | MNHEY (SEQ ID NO: 78) | SVGAGI (SEQ ID NO: 177) | CASSYRPKLDTEAFF (SEQ ID NO: 165) |
| TCR24, α | DSAIYN (SEQ ID NO: 182) | IQSSQRE (SEQ ID NO: 170) | CAVVTNDYKLSF (SEQ ID NO: 157) |
| TCR24, β | LGHDT (SEQ ID NO: 190) | YNNKEL (SEQ ID NO: 178) | CASSQDLGQGSDTQYF (SEQ ID NO: 166) |
| TCR25, α | TSDQSYG (SEQ ID NO: 185) | QGSYDEQN (SEQ ID NO: 173) | CAMRSFAQAGTALIF (SEQ ID NO: 158) |
| TCR25, β | LGHNA (SEQ ID NO: 79) | YNFKEQ (SEQ ID NO: 53) | CASSQRGKGQGDEETQYF (SEQ ID NO: 167) |
| TCR26, α | TTLSN (SEQ ID NO: 186) | LVKSGEV (SEQ ID NO: 174) | CAGWISPQGAQKLVF (SEQ ID NO: 159) |
| TCR26, β | SSHAT (SEQ ID NO: 191) | FNYEAQ (SEQ ID NO: 180) | CASSLSTNTEAFF (SEQ ID NO: 168) |

In some embodiments, the TCR library will include certain specific TCRs in particular. For instance, the library may include TCR12.

The library may include TCR14.

The library may include TCR18.

The library may include TCR26.

The skilled person will appreciate that TCRs, or functional fragments thereof, which bind the MHC molecules disclosed herein do not necessarily need to have all six CDRs as recited herein.

Moreover, the skilled person will appreciate that some modifications of the recited CDR sequences can be tolerated without abrogating binding activity.

For instance, TCR1 has been shown to function with an alternative CDR1a sequence, DISSTY (SEQ ID NO:71). Thus, TCR1 can alternatively be defined as comprising an α-chain having the following CDRs:

```
i) CDR1a:
                    (SEQ ID NO: 71)
DISSTY;

ii) CDR2a:
                    (SEQ ID NO: 35)
IFSNMDM;
```

and/or

```
iii) CDR3a:
                    (SEQ ID NO: 1)
AETLDNYGQNFV;
```

and/or as comprising a β-chain having the following CDRs:

```
iv) CDR1b:
                    (SEQ ID NO: 72)
DFQATT;

v) CDR2b:
                    (SEQ ID NO: 47)
SNEGSKA;
```

and/or

```
vi) CDR3b:
                    (SEQ ID NO: 18)
SAVDRDEPFHSNQPQH.
```

Thus, the TCRs and functional fragments of the invention include variants of the TCRs defined herein, in which one or two of the amino acid residues of the CDRs are replaced with another amino acid.

Further exemplary TCRs of the invention include:

A TCR or functional fragment thereof, comprising an α-chain having the following CDRs:

```
i) CDR1a:
                    (SEQ ID NO: 59)
TSINN;

ii) CDR2a:
                    (SEQ ID NO: 36)
IRSNERE;
```

and/or

```
iii) CDR3a:
                    (SEQ ID NO: 2)
ATWLSGSARQLTF;
```

and/or as comprising a β-chain having the following CDRs:

```
iv) CDR1b:
                    (SEQ ID NO: 73)
SGHDY;

v) CDR2b:
                    (SEQ ID NO: 48)
FNNNVP;
```

and/or

```
vi) CDR3b:
                    (SEQ ID NO: 19)
ASSNRASSYNEQF,
```

optionally wherein one or two of the amino acid residues of the CDRs are replaced with another amino acid.

A TCR or functional fragment thereof, comprising an α-chain having the following CDRs:

```
i) CDR1a:
                    (SEQ ID NO: 60)
DRGSQS;

ii) CDR2a:
                    (SEQ ID NO: 37)
IYSNGD;
```

and/or

```
iii) CDR3a:
                    (SEQ ID NO: 3)
AVNLYAGNMLT;
```

and/or as comprising a β-chain having the following CDRs:

```
iv) CDR1b:
                    (SEQ ID NO: 74)
SGHVS;

v) CDR2b:
                    (SEQ ID NO: 49)
FQNEAQ;
```

and/or

```
vi) CDR3b:
                    (SEQ ID NO: 20)
ASSSDFGNQPQH,
```

optionally wherein one or two of the amino acid residues of the CDRs are replaced with another amino acid.

A TCR or functional fragment thereof, comprising an α-chain having the following CDRs:

```
i) CDR1a:
                                    (SEQ ID NO: 61)
KTLYG;

ii) CDR2a:
                                    (SEQ ID NO: 38)
LQKGGEE;
```

and/or

```
iii) CDR3a:
                                    (SEQ ID NO: 4)
CGADRGGGKLIF;
```

and/or as comprising a β-chain having the following CDRs:

```
iv) CDR1b:
                                    (SEQ ID NO: 75)
MDHEN;

v) CDR2b:
                                    (SEQ ID NO: 50)
SYDVKM;
```

and/or

```
vi) CDR3b:
                                    (SEQ ID NO: 21)
CASSLFKGADTQYF,
```

optionally wherein one or two of the amino acid residues of the CDRs are replaced with another amino acid.

A TCR or functional fragment thereof, comprising an α-chain having the following CDRs:

```
i) CDR1a:
                                    (SEQ ID NO: 62)
TSESDYY;

ii) CDR2a:
                                    (SEQ ID NO: 39)
QEAYKQQN;
```

and/or

```
iii) CDR3a:
                                    (SEQ ID NO: 5)
CAYRSGLNNDMRF;
```

and/or as comprising a β-chain having the following CDRs:

```
iv) CDR1b:
                                    (SEQ ID NO: 76)
SGHAT;

v) CDR2b:
                                    (SEQ ID NO: 51)
FQNNGV;
```

and/or

```
vi) CDR3b:
                                    (SEQ ID NO: 22)
CASSLELAGPWGNEQFF,
```

optionally wherein one or two of the amino acid residues of the CDRs are replaced with another amino acid.

A TCR or functional fragment thereof, comprising an α-chain having the following CDRs:

```
i) CDR1a:
                                    (SEQ ID NO: 63)
SSVSVY;

ii) CDR2a:
                                    (SEQ ID NO: 40)
YLSGSTLV;
```

and/or

```
CDR3a:
                                    (SEQ ID NO: 6)
AVSDNQGGKLI;
```

and/or as comprising a β-chain having the following CDRs:

```
iv) CDR1b:
                                    (SEQ ID NO: 77)
SGHNS;

v) CDR2b:
                                    (SEQ ID NO: 48)
FNNNVP;
```

and/or

```
vi) CDR3b:
                                    (SEQ ID NO: 23)
ASSLSAAYEQY,
```

optionally wherein one or two of the amino acid residues of the CDRs are replaced with another amino acid.

A TCR or functional fragment thereof, comprising an α-chain having the following CDRs:

```
i) CDR1a:
                                    (SEQ ID NO: 64)
TSGFNG;

ii) CDR2a:
                                    (SEQ ID NO: 41)
NVLDGL;
```

and/or

```
iii) CDR3a:
                                    (SEQ ID NO: 7)
CAVRYNNARLMF;
```

and/or as comprising a β-chain having the following CDRs:

```
iv) CDR1b:
                                    (SEQ ID NO: 72)
DFQATT;

v) CDR2b:
                                    (SEQ ID NO: 47)
SNEGSKA;
```

and/or

```
vi) CDR3b:
                    (SEQ ID NO: 24)
CSAPAGMGYEQYF,
```

optionally wherein one or two of the amino acid residues of the CDRs are replaced with another amino acid.

A TCR or functional fragment thereof, comprising an α-chain having the following CDRs:

```
i) CDR1a:
                    (SEQ ID NO: 65)
NSASQS;
ii) CDR2a:
                    (SEQ ID NO: 42)
VYSSGN;
```

and/or

```
iii) CDR3a:
                    (SEQ ID NO: 8)
CVVNGVDSSYKLIF;
```

and/or as comprising a β-chain having the following CDRs:

```
iv) CDR1b:
                    (SEQ ID NO: 75)
MDHEN;
v) CDR2b:
                    (SEQ ID NO: 50)
SYDVKM;
```

and/or

```
vi) CDR3b:
                    (SEQ ID NO: 25)
CASEMAGGGDNYGYTF,
```

optionally wherein one or two of the amino acid residues of the CDRs are replaced with another amino acid.

A TCR or functional fragment thereof, comprising an α-chain having the following CDRs:

```
i) CDR1a:
                    (SEQ ID NO: 66)
NIATNDY;
ii) CDR2a:
                    (SEQ ID NO: 43)
GYKTK;
```

and/or

```
iii) CDR3a:
                    (SEQ ID NO: 9)
CLVGDEDTGRRALTF;
```

and/or as comprising a β-chain having the following CDRs:

```
iv) CDR1b:
                    (SEQ ID NO: 78)
MNHEY;
```

-continued

```
v) CDR2b:
                    (SEQ ID NO: 52)
SMNVEV;
```

and/or

```
vi) CDR3b:
                    (SEQ ID NO: 26)
CASSFSGKASYYEQYF,
```

optionally wherein one or two of the amino acid residues of the CDRs are replaced with another amino acid.

A TCR or functional fragment thereof, comprising an α-chain having the following CDRs:

```
i) CDR1a:
                    (SEQ ID NO: 67)
SVFSS;
ii) CDR2a:
                    (SEQ ID NO: 44)
VVTGGEV;
```

and/or

```
iii) CDR3a:
                    (SEQ ID NO: 10)
CAVRDQTGANNLFF;
```

and/or as comprising a β-chain having the following CDRs:

```
iv) CDR1b:
                    (SEQ ID NO: 79)
LGHNA;
v) CDR2b:
                    (SEQ ID NO: 53)
YNFKEQ;
```

and/or

```
vi) CDR3b:
                    (SEQ ID NO: 27)
CASSPEPTSGSFNEQFF,
```

optionally wherein one or two of the amino acid residues of the CDRs are replaced with another amino acid.

A TCR or functional fragment thereof, comprising an α-chain having the following CDRs:

```
i) CDR1a:
                    (SEQ ID NO: 60)
DRGSQS;
ii) CDR2a:
                    (SEQ ID NO: 37)
IYSNGD;
```

and/or

```
iii) CDR3a:
                    (SEQ ID NO: 11)
CAVNMVAGNMLTF;
```

and/or as comprising a β-chain having the following CDRs:

```
iv) CDR1b:
                                   (SEQ ID NO: 80)
SGHTA;

v) CDR2b:
                                   (SEQ ID NO: 54)
FQGTGA;
```

and/or

```
vi) CDR3b:
                                   (SEQ ID NO: 28)
CASSPDSSGANVLTF,
```

optionally wherein one or two of the amino acid residues of the CDRs are replaced with another amino acid.

A TCR or functional fragment thereof, comprising an α-chain having the following CDRs:

```
i) CDR1a:
                                   (SEQ ID NO: 68)
DSVNN;

ii) CDR2a:
                                   (SEQ ID NO: 45)
IPSGT;
```

and/or

```
iii) CDR3a:
                                   (SEQ ID NO: 12)
CAVDGNNRLAF;
```

and/or as comprising a β-chain having the following CDRs:

```
iv) CDR1b:
                                   (SEQ ID NO: 81)
SQVTM;

v) CDR2b:
                                   (SEQ ID NO: 55)
ANQGSEA;
```

and/or

```
vi) CDR3b:
                                   (SEQ ID NO: 29)
CSVDMDWGIGGYTF,
```

optionally wherein one or two of the amino acid residues of the CDRs are replaced with another amino acid.

A TCR or functional fragment thereof, comprising an α-chain having the following CDRs:

```
i) CDR1a:
                                   (SEQ ID NO: 67)
SVFSS;

ii) CDR2a:
                                   (SEQ ID NO: 44)
VVTGGEV;
```

and/or

```
iii) CDR3a:
                                   (SEQ ID NO: 13)
CAGAGYGGSQGNLIF;
```

and/or as comprising a β-chain having the following CDRs:

```
iv) CDR1b:
                                   (SEQ ID NO: 82)
LNHDA;

v) CDR2b:
                                   (SEQ ID NO: 56)
SQIVND;
```

and/or

```
vi) CDR3b:
                                   (SEQ ID NO: 30)
CASSIAGGAEQYF,
```

optionally wherein one or two of the amino acid residues of the CDRs are replaced with another amino acid.

A TCR or functional fragment thereof, comprising an α-chain having the following CDRs:

```
i) CDR1a:
                                   (SEQ ID NO: 62)
TSESDYY;

ii) CDR2a:
                                   (SEQ ID NO: 39)
QEAYKQQN;
```

and/or

```
iii) CDR3a:
                                   (SEQ ID NO: 14)
CAYIGNAGNMLTF;
```

and/or as comprising a β-chain having the following CDRs:

```
iv) CDR1b:
                                   (SEQ ID NO: 78)
MNHEY;

v) CDR2b:
                                   (SEQ ID NO: 52)
SMNVEV;
```

and/or

```
vi) CDR3b:
                                   (SEQ ID NO: 31)
CASSLSYRGLGEQFF,
```

optionally wherein one or two of the amino acid residues of the CDRs are replaced with another amino acid.

A TCR or functional fragment thereof, comprising an α-chain having the following CDRs:

i) CDR1a: (SEQ ID NO: 69)
VSGLRG;

ii) CDR2a: (SEQ ID NO: 46)
LYSAGEE;

and/or iii) CDR3a: (SEQ ID NO: 15)
CAVYHTGFQKLVF;

and/or as comprising a β-chain having the following CDRs:

iv) CDR1b: (SEQ ID NO: 75)
MDHEN;

v) CDR2b: (SEQ ID NO: 50)
SYDVKM;

and/or vi) CDR3b: (SEQ ID NO: 32)
CASSSRQGGTYEQYF, optionally wherein one or two of the amino acid residues of the CDRs are replaced with another amino acid.

A TCR or functional fragment thereof, comprising an α-chain having the following CDRs:

i) CDR1a: (SEQ ID NO: 58)
DSSSTY;

ii) CDR2a: (SEQ ID NO: 35)
IFSNMDM;

and/or iii) CDR3a: (SEQ ID NO: 16)
CAESMGDFNKFYF;

and/or as comprising a β-chain having the following CDRs:

iv) CDR1b: (SEQ ID NO: 78)
MNHEY;

v) CDR2b: (SEQ ID NO: 52)
SMNVEV;

and/or vi) CDR3b: (SEQ ID NO: 33)
CASSPGEGNQPQHF, optionally wherein one or two of the amino acid residues of the CDRs are replaced with another amino acid.

A TCR or functional fragment thereof, comprising an α-chain having the following CDRs:

i) CDR1a: (SEQ ID NO: 70)
DRVSQS;

ii) CDR2a: (SEQ ID NO: 37)
IYSNGD;

and/or iii) CDR3a: (SEQ ID NO: 17)
CAVSTNFGNEKLTF;

and/or as comprising a β-chain having the following CDRs:

iv) CDR1b: (SEQ ID NO: 83)
SGDLS;

v) CDR2b: (SEQ ID NO: 57)
YYNGEE;

and/or vi) CDR3b: (SEQ ID NO: 34)
CASSASLADNTGELFF, optionally wherein one or two of the amino acid residues of the CDRs are replaced with another amino acid.

A TCR or functional fragment thereof, comprising an α-chain having the following CDRs:

i) CDR1a: (SEQ ID NO: 58)
DSSSTY;

ii) CDR2a: (SEQ ID NO: 35)
IFSNMDM;

and/or iii) CDR3a: (SEQ ID NO: 151)
CAESTGGSYIPTF;

and/or as comprising a β-chain having the following CDRs:

iv) CDR1b: (SEQ ID NO: 187)
SNHLY;

v) CDR2b: (SEQ ID NO: 175)
FYNNEI;

and/or vi) CDR3b: (SEQ ID NO: 160)
CASASDSDDEKLFF, optionally wherein one or two of the amino acid residues of the CDRs are replaced with another amino acid.

A TCR or functional fragment thereof, comprising an α-chain having the following CDRs:

```
i) CDR1a:
                              (SEQ ID NO: 181)
YGGTVN;

ii) CDR2a:
                              (SEQ ID NO: 169)
YFSGDPLV;
```

and/or

```
iii) CDR3a:
                              (SEQ ID NO: 152)
CAVNAPGGYNKLIF;
```

and/or as comprising a β-chain having the following CDRs:

```
iv) CDR1b:
                              (SEQ ID NO: 82)
LNHDA;

v) CDR2b:
                              (SEQ ID NO: 56)
SQIVND;
```

and/or

```
vi) CDR3b:
                              (SEQ ID NO: 161)
CASSISQGGYGYTF,
```

optionally wherein one or two of the amino acid residues of the CDRs are replaced with another amino acid.

A TCR or functional fragment thereof, comprising an α-chain having the following CDRs:

```
i) CDR1a:
                              (SEQ ID NO: 68)
DSVNN;

ii) CDR2a:
                              (SEQ ID NO: 45)
IPSGT;
```

and/or

```
iii) CDR3a:
                              (SEQ ID NO: 153)
CAVERPTGGYNKLIF;
```

and/or as comprising a β-chain having the following CDRs:

```
iv) CDR1b:
                              (SEQ ID NO: 188)
SGHRS;

v) CDR2b:
                              (SEQ ID NO: 176)
YFSETQ;
```

and/or

```
vi) CDR3b:
                              (SEQ ID NO: 162)
CASSPGTDYEQYF,
```

optionally wherein one or two of the amino acid residues of the CDRs are replaced with another amino acid.

A TCR or functional fragment thereof, comprising an α-chain having the following CDRs:

```
i) CDR1a:
                              (SEQ ID NO: 182)
DSAIYN;

ii) CDR2a:
                              (SEQ ID NO: 170)
IQSSQRE;
```

and/or

```
iii) CDR3a:
                              (SEQ ID NO: 154)
CAVEDYGQNFVF;
```

and/or as comprising a β-chain having the following CDRs:

```
iv) CDR1b:
                              (SEQ ID NO: 72)
DFQATT;

v) CDR2b:
                              (SEQ ID NO: 47)
SNEGSKA;
```

and/or

```
vi) CDR3b:
                              (SEQ ID NO: 163)
CSARDLSGRSLDTQYF,
```

optionally wherein one or two of the amino acid residues of the CDRs are replaced with another amino acid.

A TCR or functional fragment thereof, comprising an α-chain having the following CDRs:

```
i) CDR1a:
                              (SEQ ID NO: 183)
TRDTTYY;

ii) CDR2a:
                              (SEQ ID NO: 171)
RNSFDEQN;
```

and/or

```
iii) CDR3a:
                              (SEQ ID NO: 155)
CALSDSSGGSYIPTF;
```

and/or as comprising a β-chain having the following CDRs:

iv) CDR1b:
(SEQ ID NO: 189)
SEHNR;

v) CDR2b:
(SEQ ID NO: 49)
FQNEAQ;

and/or vi) CDR3b:
(SEQ ID NO: 164)
CASSLGRQTNTEAFF, optionally wherein one or two of the amino acid residues of the CDRs are replaced with another amino acid.

A TCR or functional fragment thereof, comprising an α-chain having the following CDRs:

i) CDR1a:
(SEQ ID NO: 184)
DSASNY;

ii) CDR2a:
(SEQ ID NO: 172)
IRSNVGE;

and/or iii) CDR3a:
(SEQ ID NO: 156)
CAACYSGYALNF;

and/or as comprising a β-chain having the following CDRs:

iv) CDR1b:
(SEQ ID NO: 78)
MNHEY;

v) CDR2b:
(SEQ ID NO: 177)
SVGAGI;

and/or vi) CDR3b:
(SEQ ID NO: 165)
CASSYRPKLDTEAFF, optionally wherein one or two of the amino acid residues of the CDRs are replaced with another amino acid.

A TCR or functional fragment thereof, comprising an α-chain having the following CDRs:

i) CDR1a:
(SEQ ID NO: 182)
DSAIYN;

ii) CDR2a:
(SEQ ID NO: 170)
IQSSQRE;

and/or iii) CDR3a:
(SEQ ID NO: 157)
CAVVTNDYKLSF;

and/or as comprising a β-chain having the following CDRs:

iv) CDR1b:
(SEQ ID NO: 190)
LGHDT;

v) CDR2b:
(SEQ ID NO: 178)
YNNKEL;

and/or vi) CDR3b:
(SEQ ID NO: 166)
CASSQDLGQGSDTQYF, optionally wherein one or two of the amino acid residues of the CDRs are replaced with another amino acid.

A TCR or functional fragment thereof, comprising an α-chain having the following CDRs:

i) CDR1a:
(SEQ ID NO: 185)
TSDQSYG;

i) CDR2a:
(SEQ ID NO: 173)
QGSYDEQN;

and/or iii) CDR3a:
(SEQ ID NO: 158)
CAMRSFAQAGTALIF;

and/or as comprising a β-chain having the following CDRs:

iv) CDR1b:
(SEQ ID NO: 79)
LGHNA;

v) CDR2b:
(SEQ ID NO: 53)
YNFKEQ;

and/or vi) CDR3b:
(SEQ ID NO: 167)
CASSQRGKGQGDEETQYF, optionally wherein one or two of the amino acid residues of the CDRs are replaced with another amino acid.

A TCR or functional fragment thereof, comprising an α-chain having the following CDRs:

i) CDR1a:
(SEQ ID NO: 186)
TTLSN;

ii) CDR2a:
(SEQ ID NO: 174)
LVKSGEV;

and/or

```
iii) CDR3a:
                              (SEQ ID NO: 159)
CAGWISPQGAQKLVF;
```

and/or as comprising a β-chain having the following CDRs:

```
iv) CDR1b:
                              (SEQ ID NO: 191)
SSHAT;

v) CDR2b:
                              (SEQ ID NO: 180)
FNYEAQ;
```

and/or

```
vi) CDR3b:
                              (SEQ ID NO: 168)
CASSLSTNTEAFF,
```

optionally wherein one or two of the amino acid residues of the CDRs are replaced with another amino acid.

In some embodiments, the TCR or functional fragment of the invention is defined by all six CDR sequences recited herein.

In some embodiments, the TCR library of the invention comprises a group of TCRs that share certain structural motifs. For instance, the TCR library may comprise a group of TCRs (two or more, three or more, or four or more TCRs) that each have a "DSSSTY" motif (SEQ ID NO:58) as CDR1a. And/or, the TCR library may comprise a group of TCRs (two or more, three or more, or four or more TCRs) that each have an "SxNN" motif (SEQ ID NO:84) in CDR1a. Preferably the "x" in the SxNN (SEQ ID NO: 84) motif represents isoleucine or valine (see SEQ ID NO:85 and SEQ ID NO:86). And/or, the TCR library may comprise a group of TCRs (two or more, three or more, four or more, or five or more TCRs) that each have an "SQS" motif (SEQ ID NO:87) in CDR1a. The SQS motif may be part of a longer "DRxSQS" motif (SEQ ID NO:89). Preferably the "x" in the DRxSQS motif represents glycine or valine. And/or, the TCR library may comprise a group of TCRs (two or more, three or more, or four or more TCRs) that each have a "TSESDYY" motif (SEQ ID N0:62) as CDR1a. And/or, the TCR library may comprise a group of TCRs (two or more, three or more, four or more, five or more, or six or more TCRs) that each have an "SV" motif (SEQ ID NO:92) in CDR1a. And/or, the TCR library may comprise a group of TCRs (two or more, or three or more, or four or more TCRs) that each have an "SVFSS" motif (SEQ ID NO:93) as CDR1a. And/or, the TCR library may comprise a group of TCRs (two or more, three or more, or four or more TCRs) that each have a "DFQATT" motif (SEQ ID NO:94) as CDR1b. And/or, the TCR library may comprise a group of TCRs (two or more, three or more, four or more, five or more, six or more, seven or more, or eight or more TCRs) that each have a "SG" motif (SEQ ID NO:95) in CDR1b. The SG (SEQ ID NO: 95) motif may be part of a longer "SGH" motif (SEQ ID NO:96). And/or, the TCR library may comprise a group of TCRs (two or more, three or more, four or more, five or more, six or more, or seven or more TCRs) that each have an "MxHEz" motif (SEQ ID NO:97) in CDR1b. Preferably, the x in the MxHEz (SEQ ID NO: 97) motif is asparagine or aspartic acid (see SEQ ID NO:98 and SEQ ID NO:99). Preferably, the z in the MxHEz (SEQ ID NO: 97) motif is asparagine or tyrosine (see SEQ ID NO:100 and SEQ ID NO:101). And/or, the TCR library may comprise a group of TCRs (two or more, three or more, or four or more TCRs) that each have an "GHN" motif (SEQ ID NO:102) in CDR1b. In some cases, the SGH (SEQ ID NO: 96) and GHN (SEQ ID NO: 102) motifs are each part of a single "SGHN" motif (SEQ ID NO:103) in CDR1b. And/or, the TCR library may comprise a group of TCRs (two or more, three or more, four or more, five or more, six or more, seven or more, eight or more, or nine or more TCRs) that each have an "SN" motif (SEQ ID NO:104) in CDR2a. In some cases, the SN (SEQ ID NO: 104) motif is part of a longer "IFSNMDM" motif (SEQ ID NO:105), which forms CDR2a. In other cases, the SN (SEQ ID NO: 104) motif is part of a longer "IYSNGD" motif (SEQ ID NO:106), which forms CDR2a. And/or, the TCR library may comprise a group of TCRs (two or more, three or more, or four or more TCRs) that each have a "GGE" motif (SEQ ID NO:107) in CDR2a. In some cases, the GGE motif is part of a longer "VVTGGEV" motif (SEQ ID NO:108), which forms CDR2a. And/or, the TCR library may comprise a group of TCRs (two or more, three or more, or four or more TCRs) that each have a "YK" motif (SEQ ID NO:109) in CDR2a. In some cases, the YK is part of a longer "QEAYKQQN" motif (SEQ ID NO:110), which forms CDR2a. And/or, the TCR library may comprise a group of TCRs (two or more, three or more, or four or more TCRs) that each have a "GEE" motif (SEQ ID NO:111) in CDR2a. And/or, the TCR library may comprise a group of TCRs (two or more, three or more, or four or more TCRs) that each have a "SNEG-SKA" motif (SEQ ID NO:112), which forms CDR2b. And/or, the TCR library may comprise a group of TCRs (two or more, three or more, or four or more TCRs) that each have a "FNNNVP" motif (SEQ ID NO:113), which forms CDR2b. And/or, the TCR library may comprise a group of TCRs (two or more, three or more, or four or more TCRs) that each have an "FQN" motif (SEQ ID NO:179) in CDR2b. And/or, the TCR library may comprise a group of TCRs (two or more, three or more, or four or more TCRs) that each have a "SYDVKM" motif (SEQ ID NO:114), which forms CDR2b. And/or, the TCR library may comprise a group of TCRs (two or more, three or more, or four or more TCRs) that each have a "SMNVEV" motif (SEQ ID NO:115), which forms CDR2b. And/or, the TCR library may comprise a group of TCRs (two or more, three or more, or four or more TCRs) that each have a "DNxG" motif (SEQ ID NO:116) in CDR3a. Preferably, the "x" in DNxG (SEQ ID NO: 116) is tyrosine. And/or, the TCR library may comprise a group of TCRs (two or more, three or more, four or more, five or more, or six or more TCRs) that each have an "KLI" motif (SEQ ID NO:118) and/or, a "KLxF" motif (SEQ ID NO:) in CDR3a. Thus, the KLI motif may be part of a longer "KLIF" motif (SEQ ID NO:121). And/or, the TCR library may comprise a group of TCRs (two or more, three or more, or four or more, five or more, or six or more TCRs) that each have an "LTF" motif (SEQ ID NO:122) in CDR3a. And/or, the TCR library may comprise a group of TCRs (two or more, three or more, or four or more TCRs) that each have a "AGNMLT" motif (SEQ ID NO:123) in CDR3a. In some cases, the LTF and AGNMLT are each part of a single "AGNMLTF" motif (SEQ ID NO:124). And/or, the TCR library may comprise a group of TCRs (two or more, three or more, or four or more TCRs) that each have a "GGKLI" motif (SEQ ID NO:125) in CDR3a. And/or, the TCR library may comprise a group of TCRs (two or more, three or more, four or more, five or more, six or more, seven or more, eight or more, nine or more, ten or more, or eleven or more TCRs) that each have a "CAV" motif (SEQ ID NO:126) in CDR3a. The CAV motif may be part of a longer "CAVR" motif (SEQ ID NO:127) in CDR3a. And/or, the TCR library may comprise a group of TCRs (two or more, three or more, or four or more TCRs) that each have an "NxRLzF" motif (SEQ ID NO:128) in CDR3a. Preferably, the "x" in NxRLzF is arginine or alanine (see SEQ ID NO:129 and SEQ ID NO:130) and the "z" in NxRLzF is methionine or alanine (see SEQ ID NO:131 and SEQ ID NO:132). And/or, the TCR library may comprise a group of TCRs (two or more, three or more, or four or more TCRs) that each have a "GGS" motif (SEQ ID NO:193) in CDR3a. And/or, the TCR library may comprise a group of TCRs (two or more, three or more, or four or more TCRs) that each have a "NQPQH" motif (SEQ ID NO:133) in CDR3b. And/or, the TCR library may comprise a group of TCRs (two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, 20 or more, 21 or more, or 22 or more TCRs) that each have an "ASS" motif (SEQ ID NO:134) in CDR3b. The ASS motif may form part of a longer "ASSL" motif (SEQ ID NO:135), "ASSS" motif (SEQ ID NO:136) and/or "CASS" motif (SEQ ID NO:137) in CDR3b. Thus, the TCR library may comprise a group of TCRs that each have a "CASSL" motif (SEQ ID NO:138) in CDR3b. And/or, the TCR library may comprise a group of TCRs (two or more, three or more, or four or more TCRs) that each have an "EQFF" motif (SEQ ID NO:139) in CDR3b The NQPQH motif may be part of a longer "GNQPQH" motif (SEQ ID NO:140). And/or, the TCR library may comprise a group of TCRs (two or more, three or more, four or more five or more, six or more, seven or more, eight or more, or nine or more TCRs) that each have a "QYF" motif (SEQ ID NO:141) in CDR3b. And/or, the TCR library may comprise a group of TCRs five or more, six or more, seven or more, eight or more, nine or more, or ten or more) that each have an "EQ" motif (SEQ ID NO:142) in CDR3b. The QYF motif may be part of a longer "EQYF" motif (SEQ ID NO:143) and/or "YEQYF" motif (SEQ ID NO:144) in CDR3b. The EQ motif may be part of a longer "EQF" motif (SEQ ID NO:145), "NEQF" motif (SEQ ID NO:146), and/or "NEQFF" motif (SEQ ID NO:147); or the EQ motif may be part of a longer "EQY" motif (SEQ ID NO:148) and/or "YEQY" motif (SEQ ID NO:149) in CDR3b. And/or, the TCR library may comprise a group of TCRs (two or more, three or more, or four or more TCRs) that each have a "GYTF" motif (SEQ ID NO:150) in CDR3b. And/or, the TCR library may comprise a group of TCRs (two or more, three or more, or four or more TCRs) that each have a "TEAFF" motif (SEQ ID NO:192) in CDR3b.

The library of the invention may include more than one group of TCRs that share certain structural motifs described herein. For instance the TCR library can include two groups of TCRs, wherein the TCRs of each group share a particular structural motif described herein. Similarly, the TCR library can include three, four, five or six groups of TCRs, wherein the TCRs of each group share a particular structural motif described herein.

The skilled person will appreciate that the TCRs of the invention that have a CDR sequence defined herein will generally also bind to one or more of the MHC molecules listed herein. The TCRs of the invention may therefore be defined both by sequence and binding properties. For instance, the TCRs of the libraries of the invention may be defined by a particular combination of (i) CDR sequence and (ii) the MHC molecule (or molecules) that can be specifically bound. Thus, in some embodiments the library includes one or more of the TCRs defined by Table 3. (Table 3 defines the TCRs by their CDR3 sequences and by their MHC restriction. Further sequence information disclosed herein may be used to define these TCRs.)

TABLE 3

TCR/MHC-restriction

| TCR | CDR3a/CDR3b | MHC restriction |
|---|---|---|
| 1 | AETLDNYGQNFV (SEQ ID NO: 1) SAVDRDEPFHSNQPQH (SEQ ID NO: 18) | HLA-C*0801 |
| 2 | ATWLSGSARQLTF (SEQ ID NO: 2) ASSNRASSYNEQF (SEQ ID NO: 19) | HLA-A*0201; HLA-A*0203; HLA-A*0206; HLA-A*0207 |
| 3 | AVNLYAGNMLT (SEQ ID NO: 3) ASSSDFGNQPQH (SEQ ID NO: 20) | HLA-A*0201; HLA-A*0203; HLA-A*0206; HLA-A*0207 |
| 4 | CGADRGGGKLIF (SEQ ID NO: 4) CASSLFKGADTQYF (SEQ ID NO: 21) | HLA-A*0201; HLA-A*0203; HLA-A*0206; HLA-A*0207 |
| 5 | CAYRSGLNNDMRF (SEQ ID NO: 5) CASSLELAGPWGNEQFF (SEQ ID NO: 22) | HLA-A*1101; HLA-A*1102 |
| 6 | AVSDNQGGKLI (SEQ ID NO: 6) ASSLSAAYEQY (SEQ ID NO: 23) | HLA-B*5801/HLA-C*0302 |
| 7 | CAVRYNNARLMF (SEQ ID NO: 7) CSAPAGMGYEQYF (SEQ ID NO: 24) | HLA-B*5801/HLA-C*0302 |
| 8 | CVVNGVDSSYKLIF (SEQ ID NO: 8) CASEMAGGGDNYGYTF (SEQ ID NO: 25) | HLA-A*0201; HLA-A*0203; HLA-A*0206; HLA-A*0207 |
| 9 | CLVGDEDTGRRALTF (SEQ ID NO: 9) CASSFSGKASYYEQYF (SEQ ID NO: 26) | HLA-B*0706; HLA-B*3915 |
| 10 | CAVRDQTGANNLFF (SEQ ID NO: 10) CASSPEPTSGSFNEQFF (SEQ ID NO: 27) | HLA-A*0201; HLA-A*0203; HLA-A*0206; HLA-A*0207 |
| 11 | CAVNMVAGNMLTF (SEQ ID NO: 11) CASSPDSSGANVLTF (SEQ ID NO: 28) | HLA-A*0201; HLA-A*0203; HLA-A*0206; HLA-A*0207 |
| 12 | CAVDGNNRLAF (SEQ ID NO: 12) CSVDMDWGIGGYTF (SEQ ID NO: 29) | HLA-A*1101; HLA-A*1102 |
| 13 | CAGAGYGGSQGNLIF (SEQ ID NO: 13) CASSIAGGAEQYF (SEQ ID NO: 30) | HLA-B*4001 |

TABLE 3-continued

TCR/MHC-restriction

| TCR | CDR3a/CDR3b | MHC restriction |
|---|---|---|
| 14 | CAYIGNAGNMLTF (SEQ ID NO: 14) CASSLSYRGLGEQFF (SEQ ID NO: 31) | HLA-A*1101; HLA-A*1102 |
| 15 | CAVYHTGFQKLVF (SEQ ID NO: 15) CASSSRQGGTYEQYF (SEQ ID NO: 32) | HLA-B*4040; HLA-C*0822 |
| 16 | CAESMGDFNKFYF (SEQ ID NO: 16) CASSPGEGNQPQHF (SEQ ID NO: 33) | HLA-A*6802; HLA-B*1510 |
| 17 | CAVSTNFGNEKLTF (SEQ ID NO: 17) CASSASLADNTGELFF (SEQ ID NO: 34) | HLA-C*0706 |
| 18 | CAESTGGSYIPTF (SEQ ID NO: 151) CASASDSDDEKLFF (SEQ ID NO: 160) | HLA-A*2401; HLA-A*2402; HLA-A*2407 |
| 19 | CAVNAPGGYNKLIF (SEQ ID NO: 152) CASSISQGGYGYTF (SEQ ID NO: 161) | HLA-B*4403 |
| 20 | CAVERPTGGYNKLIF (SEQ ID NO: 153) CASSPGTDYEQYF (SEQ ID NO: 162) | HLA-A*1101; HLA-A*1102 |
| 21 | CAVEDYGQNFVF (SEQ ID NO: 154) CSARDLSGRSLDTQYF (SEQ ID NO: 163) | HLA-B*3501; HLA-B*3503 |
| 22 | CALSDSSGGSYIPTF (SEQ ID NO: 155) CASSLGRQTNTEAFF (SEQ ID NO: 164) | HLA-B*5502 |
| 23 | CAACYSGYALNF (SEQ ID NO: 156) CASSYRPKLDTEAFF (SEQ ID NO: 165) | HLA-C*1202; HLA-C*1203 |
| 24 | CAVVTNDYKLSF (SEQ ID NO: 157) CASSQDLGQGSDTQYF (SEQ ID NO: 166) | HLA-C*1202; HLA-C*1203 |
| 25 | CAMRSFAQAGTALIF (SEQ ID NO: 158) CASSQRGKGQGDEETQYF (SEQ ID NO: 167) | HLA-B*5801; HLA-C*0302 |
| 26 | CAGWISPQGAQKLVF (SEQ ID NO: 159) CASSLSTNTEAFF (SEQ ID NO: 168) | HLA-A*2401; HLA-A*2402; HLA-A*2407 |

The skilled person will note that some of the TCRs of the invention are capable of specifically binding to more than one MHC haplotype (MHC molecule). In other words some of the TCRs of the invention are 'restricted' to more than one MHC molecule. For instance, TCR2, TCR3, TCR4, TCR8, TCR10 and TCR11 can each bind HLA-A*0201, HLA-A*0203, HLA-A*0206 and HLA-A*0207.

In some embodiments, the TCR library of the invention includes two or more, three or more, or four or more TCRs that are restricted to HLA-A*0201, HLA-A*0203, HLA-A*0206 and/or HLA-A*0207. In some embodiments, the TCR library of the invention includes five or more TCRs that are restricted to HLA-A*0201, HLA-A*0203, HLA-A*0206 and/or HLA-A*0207. In some embodiments, the TCR library of the invention includes six or more TCRs that are restricted to HLA-A*0201, HLA-A*0203, HLA-A*0206 and/or HLA-A*0207.

In some embodiments, the TCR library of the invention includes one or more TCRs that are restricted to HLA-A*1101 and/or HLA-A*1102. In some embodiments, the TCR library of the invention includes two or more TCRs that are restricted to HLA-A*1101 and/or HLA-A*1102. In some embodiments, the TCR library of the invention includes three or more TCRs that are restricted to HLA-A*1101 and/or HLA-A*1102. In some embodiments, the TCR library of the invention includes four or more TCRs that are restricted to HLA-A*1101 and/or HLA-A*1102.

In some embodiments, the TCR library of the invention includes one or more TCRs that are restricted to HLA-A*2401, HLA-A*2402 and/or HLA-A*2407. In some embodiments, the TCR library of the invention includes two or more TCRs that are restricted to HLA-A*2401, HLA-A*2402 and/or HLA-A*2407.

In some embodiments, the TCR library of the invention includes one or more TCRs that are restricted to HLA-B*5801/HLA-C*0302. In some embodiments, the TCR library of the invention includes two or more TCRs that are restricted to HLA-B*5801/HLA-C*0302. In some embodiments, the TCR library of the invention includes three or more TCRs that are restricted to HLA-B*5801/HLA-C*0302. (The HLA-B*5801 and HLA-C*0302 haplotypes are always found together in individuals.)

In some embodiments, the TCR library of the invention includes one or more TCRs that are restricted to HLA-B*0706 and/or HLA-B*3915.

In some embodiments, the TCR library of the invention includes one or more TCRs that are restricted to HLA-B*3501 and/or HLA-B*3503.

In some embodiments, the TCR library of the invention includes one or more TCRs that are restricted to HLA-C*1202 and/or HLA-C*1203. In some embodiments, the TCR library of the invention includes two or more TCRs that are restricted to HLA-C*1202 and/or HLA-C*1203.

In some embodiments, the TCR library of the invention includes one or more TCRs that are restricted to HLA-B*4001. In some embodiments, the TCR library of the invention includes one or more TCRs that are restricted to HLA-B*4040 and/or HLA-C*0822. In some embodiments, the TCR library of the invention includes one or more TCRs that are restricted to HLA-A*6802 and/or HLA-B*1510.

The skilled person will also appreciate that the number of TCRs defined (wholly or in part) by CDR sequence present in the library of the invention is preferably greater than one. Accordingly, the library of TCRs may include two or more TCRs that each have a CDR sequence listed herein. In some embodiments, the library includes three or more TCRs that each have a CDR sequence listed herein. In some embodiments, the library includes four or more TCRs that each have a CDR sequence listed herein. In some embodiments, the library includes five or more TCRs that each have a CDR sequence listed herein. In some embodiments, the library includes six or more, seven or more, eight or more, or nine or more TCRs that each have a CDR sequence listed herein. In some embodiments, the library includes ten or more TCRs that each have a CDR sequence listed herein. In some embodiments, the library includes more than ten TCRs that each have a CDR sequence listed herein, for instance 11 or more, 12 or more, 13 or more, 14 or more, 15 or more, or 16 or more, 17 or more, 18 or more, 19 or more, 20 or more, 21 or more, 22 or more, 23 or more, 24 or more, 25, or all 26 TCRs that each have a CDR sequence listed herein.

Whilst the TCR library includes one or more of the TCRs disclosed herein, in some embodiments, the library can be defined as excluding particular TCRs disclosed herein. For instance the TCR library may exclude any or all of TCR1, TCR2, TCR3 and/or, TCR4 (as defined herein, e.g. in Tables 1 and 2). For instance, the TCR library of the invention may exclude TCR1. The TCR library of the invention may exclude TCR2. The TCR library of the invention may exclude TCR3. The TCR library of the invention may exclude TCR4. The TCR library of the invention may exclude TCRs 1 and 2. The TCR library of the invention may exclude TCRs 1 and 3. The TCR library of the invention may exclude TCRs 1 and 4. The TCR library of the invention may exclude TCRs 2 and 3. The TCR library of the invention may exclude TCRs 2 and 4. The TCR library of the invention may exclude TCRs 3 and 4. The TCR library of the invention may exclude TCRs 1, 2 and 3. The TCR library of the invention may exclude TCRs 1, 2 and 4. The TCR library of the invention may exclude TCRs 2, 3 and 4. The TCR library of the invention may exclude TCRs 1, 2, 3 and 4.

In another aspect, the invention provides a TCR disclosed herein. This TCR can be considered to be 'selected from' the TCR library of the invention, although it can also be defined without regard to the library. For instance, the TCR of this aspect can be defined by one or more of its CDR sequences (e.g. by its CDR3 sequences, or by some or all of its six CDR sequences) and/or by the MHC molecule that it binds. The TCR selected from the TCR library of the invention may expressly be selected from a subset of the TCRs as disclosed herein, for instance, the TCR selected from the TCR library of the invention may exclude particular TCRs. In some embodiments, the TCR selected from the TCR library of the invention does not comprise SEQ ID NO:1 or 18. In some embodiments, the TCR selected from the TCR library of the invention does not comprise SEQ ID NO:2 or 19. In some embodiments, the TCR selected from the TCR library of the invention does not comprise SEQ ID NO:3 or 20. In some embodiments, the TCR selected from the TCR library of the invention does not comprise SEQ ID NO:4 or 21. In some embodiments, the TCR selected from the TCR library of the invention does not comprise SEQ ID NO:5 or 22. In some embodiments, the TCR selected from the TCR library of the invention does not comprise SEQ ID NO:6 or 23.

In another aspect, the invention provides a nucleic acid, which is optionally isolated, which encodes the alpha chain of a TCR of the invention. The related aspect is a nucleic acid, which is optionally isolated, which encodes the beta chain of a TCR of the invention. In some embodiments, the optionally isolated nucleic acid encodes both the alpha and beta chains. In other embodiments, the alpha and beta chains are encoded by two separate nucleic acids (which can be termed 'a pair of nucleic acids') and these nucleic acids can be used in conjunction with each other e.g. to express a TCR of the invention in an expression system, e.g. a cell. Preferably the cell is a eukaryotic cell. In embodiments in which a single nucleic acid encodes both the alpha and beta chain, the nucleic acid may comprise (a) a nucleic acid sequence encoding a TCR α-chain comprising a variable region and a constant region; (b) a nucleic acid sequence encoding a TCR β-chain comprising a variable region and a constant region; and (c) a nucleic acid sequence encoding a cleavable linker, wherein sequence (c) is located in the isolated nucleic acid between sequences (a) and (b), and wherein sequences (a), (b) and (c) are in the same reading frame. In some embodiments the cleavable linker is a Picornavirus 2A (P2A) linker. In some embodiments the constant region of the TCR α-chain and/or the constant region of the TCR β-chain additionally encode at least one non-native cysteine residue for forming a disulphide bond between the TCR α-chain and TCR β-chain.

In another aspect the present invention provides a vector comprising an isolated nucleic acid according to the present invention, wherein the vector is selected from the group consisting of plasmids, binary vectors, DNA vectors, mRNA vectors, retroviral vectors, lentiviral vectors, transposon-based vectors, and artificial chromosomes.

In another aspect, the invention provides a library of isolated nucleic acids, which each encode a TCR according to the invention. In some embodiments, the library of isolated nucleic acids encodes two or more of the disclosed TCRs. In some embodiments, library of isolated nucleic acids encodes three or more of the disclosed TCRs. In some embodiments, the library of isolated nucleic acids encodes four or more of the disclosed TCRs. In some embodiments, the library of isolated nucleic acids encodes five or more of the disclosed TCRs. In some embodiments, the library of isolated nucleic acids encodes six or more, seven or more, eight or more, or nine or more of the disclosed TCRs. In some embodiments, the library of isolated nucleic acids encodes ten or more of the disclosed TCRs. In some embodiments, the library of isolated nucleic acids encodes more than ten of the disclosed TCRs, for instance 11 or more, 12 or more, 13 or more, 14 or more, 15 or more, 16 or more, 17 or more, 18 or more, 19 or more, 20 or more, 21 or more, 22 or more, 23 or more, 24 or more, 25, or all 26 isolated nucleic acids.

In another aspect, the present invention provides an isolated polypeptide encoded by an isolated nucleic acid or vector according to the present invention.

In another aspect, the present invention provides an in vitro method of producing an HBV reactive T cell, comprising introducing into a target cell a nucleic acid or vector according to the present invention. The nucleic acid or vector can be introduced into the cell by any suitable method, for instance electroporation, transfection or transduction and/or CRISPR/Cas9-type gene editing techniques. The target cell, which receives the nucleic acid or vector can be termed a recipient cell. In some embodiments, the recipient cell is a T cell or T cell precursor. In preferred embodiments, the recipient cell is an activated T cell. Alternatively, the recipient cell may be a non-activated (resting) T cell, e.g. as disclosed by WO2017/171631. The recipient cells (e.g. T cell precursors and/or T cells) may be present in a cellular mixture, for instance a solution of peripheral blood mononuclear cells (PBMCs). Thus, the in vitro method of producing a HBV reactive T cell may involve introducing the nucleic acid or vector into PBMCs, e.g. via transfection. The recipient cell may have been obtained from a patient who has, or had, or is at risk of contracting an HBV infection or a hepatocellular carcinoma. The patient may have hepatitis. In some embodiments, the method additionally comprises propagating and/or culturing the cell under conditions suitable for expression of the isolated nucleic acid or vector by the cell.

In a related aspect, the present invention provides a cell, optionally isolated, which is obtained or obtainable by the method of producing a HBV reactive T cell according to the present invention. Thus, in one aspect the invention provides a T cell that expresses a TCR disclosed herein. In some embodiments, the T cell has been isolated from a patient sample. The T cell may also expresses a further endogenous TCR that is not from the TCR library. Preferably, the T cell is a CD8+ T cell. The skilled person will appreciate that the cell of the invention can be used in medicine.

In some aspects, the invention provides a method of selecting a patient for treatment, wherein the method comprises determining the HLA-A haplotype, the HLA-B haplotype, and/or the HLA-C haplotype of the patient, and then selecting a TCR from the TCR library of the invention, wherein the selected TCR is capable of specifically binding an HLA-A, HLA-B, and/or HLA-C molecule expressed by the patient. In other words, the patient is selected for treatment if they are immunologically compatible with one or more of the TCRs in the library. The step of determining the HLA-A haplotype of the patient does not need to be performed at the same time or place, or by the same entity, as the step of selecting the TCR from the library. In some embodiments, the patient is a hepatitis patient, e.g. an HBV patient or a hepatitis D (HDV) patient. In some embodiments, the patient has, or had, or is at risk of contracting an HBV and/or HDV infection or a hepatocellular carcinoma. The patient may have hepatitis. The patient may have been diagnosed with recurrent HBV-related HCC. The method may also comprise a step (prior to selecting the TCR from the TCR library) of detecting an HBV antigen and/or an HBV nucleic acid fragment in a sample that has been taken from the patient. In some embodiments, the patient has not received a liver transplant. In other embodiments, the patient has received, or is scheduled to receive, a liver transplant, and the method may further comprise a step (prior to selecting the TCR from the TCR library) of determining the HLA-A haplotype, the HLA-B haplotype, and/or the HLA-C haplotype of the transplanted liver. The chosen TCR should not bind an HLA expressed by the transplanted liver but should bind an HLA expressed by the patient, in order to ensure immunological compatibility.

In some aspects, the invention provides a method of treating a patient that has been selected by the selection methods described herein. In related aspects, the invention provides a lymphocyte (e.g. T cell) of the invention for use in a method of treating patient that has been selected by the selection methods described herein. The step of selecting the patient does not need to be performed at the same time or place, or by the same entity, as the step of treating the patient. In other related aspects, the invention provides the use of a TCR of the invention, or of a lymphocyte (e.g. T cell) of the invention, in the manufacture of a medicament for treating patient that has been selected by the selection methods described herein. In these aspects, the treatment comprises administering a lymphocyte (e.g. T cell), which expresses a TCR of the invention, to the patient. The lymphocyte (e.g. T cell) may be administered via intravenous infusion. The lymphocyte (e.g. T cell) may be administered via intra-tumoral infusion. Alternatively, the lymphocyte (e.g. T cell) may be administered via intra-arterial infusion, in an artery that supplies blood to a tumour. The lymphocyte (e.g. T cell) may be derived from an autologous lymphocyte (e.g. T cell) that had been harvested from the patient and into which has been modified to express a TCR described herein, e.g. via the introduction of a nucleic acid encoding the TCR into the autologous lymphocyte (e.g. T cell). In some embodiments, the patient is an HBV patient. In some embodiments, the patient has, or had, or is at risk of contracting an HBV infection or a hepatocellular carcinoma. The patient may be have hepatitis. In some embodiments, the patient has been diagnosed with recurrent HBV-related HCC. In some embodiments, the patient has received, or is scheduled to receive, a liver transplant. In some embodiments, the patient is a HDV patient, optionally co-infected with HBV.

The invention includes the combination of the aspects and preferred features described except where such a combination is clearly impermissible or expressly avoided.

DETAILED DESCRIPTION OF THE INVENTION

Aspects and embodiments of the present invention will now be discussed with reference to the accompanying figures. Further aspects and embodiments will be apparent to those skilled in the art. All documents mentioned in this text are incorporated herein by reference.

T Cell Receptor

T Cell Receptors (TCRs) are heterodimeric, antigen-binding molecules typically comprising an α-chain and a β-chains. In nature, α-chain and β-chains are expressed at the cell surface of T cells (αβ T cells) as a complex with invariant CD3 chains. An alternative TCR comprising γ and δ chains is expressed on a subset of T cells (γδ T cells). TCRs recognise (bind to) antigens presented by major histocompatibility complex (MHC) molecules. TCR structure and recognition of MHC-presented antigens is described in detail for example in Immunobiology, 5th Edn. Janeway C A Jr, Travers P, Walport M, et al. New York: Garland Science (2001), Chapters 3 and 6, which are hereby incorporated by reference in their entirety.

TCR α-chain and β-chains comprise a constant (C) region, and a variable (V) region. The variable regions of the α-chain and β-chain polypeptides bind to the MHC molecule via three complementary determining regions (CDRs), which are the regions of the V region that determines its binding specificity. The CDRs for the TCR α-chain and β-chain are designated CDR1a-3a and CDR1b-3b respectively. The capacity for CDR sequences to determine TCR specificity is illustrated by studies showing that TCR specificity can be switched via directed mutation of the CDRs (Smith et al, Nature Communications 2014, which is hereby incorporated by reference in its entirety.) Recent studies have shown that CDR3s are particularly important for determining TCR specificities and that TCRs with matching CDR3 sequences are likely to have the same specificity (Thakkar and Bailey-Kellogg, BMC Bioinformatics 2019, which is hereby incorporated by reference in its entirety.)

In some embodiments of the present invention a TCR, fragment or polypeptide may be defined by reference to CDR1a, CDR2a, CDR3a, CDR1b, CDR2b and/or CDR3b. The variable regions of the α-chain and β-chain also comprise framework regions between the CDRs.

TCRs, fragments and polypeptides according to the invention may comprise one or more CDRs which are variant CDRs of the CDRs described herein. A variant may have one or two amino acid substitutions in the CDR sequence. In some embodiments, a variant may have three or four amino acid substitutions in the CDR sequence.

The CDRs described herein may be useful in conjunction with a number of different framework regions. Amino acid sequences for TCR α-chain and TCR β-chain framework regions are well known in the art, and can for example be identified with reference to, or retrieved from, the immunogenetics (IMGT) database (http://www.imgt.org).

The skilled person would understand that the CDR sequences of the invention can be grafted onto framework regions with which the CDRs are not naturally associated to produce a new, artificial TCR, which retains the target specificity of the donor TCR (as defined by the CDRs) and/or substantially the same binding affinity for the target.

Soluble TCRs

In some embodiments, the TCR is a soluble TCR (sTCR), optionally wherein the soluble TCR does not comprise a transmembrane domain and/or a cytoplasmic domain. Soluble TCRs can be expressed in bacterial, fungal, mammalian and insect cells. For example, soluble TCRs can be expressed in human cells using a bicistronic vector encoding both the TCRα and β chains, without the transmembrane and intracellular domains, separated by the ribosomal skipping sequence 2A found in the picorna virus (Walseng, et al. 2015). Additionally, the interchain affinity of the sTCR can be increased by the addition of a cysteine bridge or a leucine zipper (LZ) pair. The use of cysteine bridge or a leucine zipper may facilitate pairing of α and β chains that otherwise would not naturally pair (Walseng, et al. 2015).

The advantage of sTCR is that they can be internalised into the target cell upon binding of the cognate target. MHC complexes are constitutively internalised and recycled and this mechanism can be exploited to transport sTCRs inside target cells (Walseng, et al. 2015). Without being bound by theory, it is anticipated that these sTCRs could be utilised to transport cargo into target cells. A cargo could be linked to the C- or N-terminal of the TCR α and/or β chains. Examples of cargo include a radionuclide, a biotoxin, a cytokine, an antibody, an antibody Fc fragment, a virus particle, a liposome, a prodrug, and a drug (e.g. chemotherapeutic agent).

Chimeric TCRs

It has been reported that soluble TCRs can be fused to a Chimeric Antigen Receptor (CAR)-signalling tail to give rise to a TCR-CAR. The sTCR may be linked to the transmembrane and signalling domains of a CAR construct, for example, CD28 transmembrane followed by part of CD28 and CD3ζ intracellular domains. Importantly, the specificity of the TCR is maintained when the TCR is combined with the transmembrane and signalling domains of CAR. In some embodiments, these TCR-CARs can be used to re-direct cells other than T cells such as NK cells, this is based on the finding that TCR-CAR maintained its specificity in CD3-free NK cells (Walseng, et al. 2017).

The Library

The library of the invention can take various physical forms. At its broadest, the library is a collection of TCR sequences—and the sequences can be can be simply written on the page and/or stored in digital form on a computer readable medium, which is preferably a non-transitory storage medium. In this form, the step of selecting a TCR may be followed by the step of generating a corresponding nucleic acid sequence, or obtaining the corresponding nucleic acid sequence from a 3$^{rd}$ party manufacturer. Additionally or alternatively, the TCR sequences of the library are maintained as a collection of nucleic acid samples, preferably DNA samples. Each nucleic acid (which encodes a TCR of the library) is preferably stored in its own container, which will be labelled (or identifiable in some way) to enable identification of the TCR sequence encoded by the nucleic acid sample. Thus, the library of the invention can be stored in the form of nucleic acids in a set of containers. The nucleic acids that encode the TCRs of the invention may be formulated ready for delivery into cells, e.g. within a viral or non-viral delivery vector. Thus, the library may by in the form of a set of vectors, each in a separate container. Additionally or alternatively, the library can take the form of a set of T cells, which each express a TCR of the invention. The T cells may be frozen for storage.

Specific Binding

The skilled person will understand that, in the context of this patent application, the ability of a TCR to "specifically bind" to a particular target distinguishes this binding from the kinds of low affinity protein-protein interactions that are commonly termed unspecific binding or non-specific binding. The specific binding of a TCR will generally be of a high enough affinity to induce an immune reaction of a T cell that expresses the TCR when the specific binding occurs. Thus, the specific binding of a TCR can be considered to be immunologically effective binding. The skilled person will understand that, in the context of this patent application, the ability of a TCR to "specifically bind" a particular target does not imply that the TCR cannot specifically bind any other targets. On the contrary, as described herein, many TCRs of the present invention are able to specifically bind to several different MHC molecules such that an effective immunological reaction can be triggered. This ability to specifically bind to more than one target may be referred to as 'promiscuity' in this patent application.

Peptide Antigen Presentation

Antigens are processed by the molecular machinery of antigen presenting cells (APCs) to peptides, which then become associated with MHC molecules and presented as peptide-MHC complexes at the cell surface. Antigen processing, loading and presentation on MHC is described in detail in, for example, Immunobiology, 5$^{th}$ Edn. Janeway C A Jr, Travers P, Walport M, et al. New York: Garland Science (2001), Chapter 5, which is hereby incorporated by reference in entirety.

The present invention is particularly concerned with T cells reactive to HBV. Accordingly, in embodiments of the present invention the TCRs, fragments, polypeptides and cells are capable of binding to an MHC molecule defined herein, presenting a peptide derived from a HBV polypeptide.

An "HBV polypeptide" as used herein refers to a polypeptide derived from a HBV virion or encoded by nucleic acid from HBV. The nucleic acid from HBV may be a sequence that originated from HBV but has integrated into the genomic DNA of a host cell. Integrated HBV sequences can give rise to the expression of HBV peptides or polypeptides in patients, e.g. HCC patients, even after the original HBV infection has cleared. The skilled person can readily identify such viral sequences that are integrated into the genome of host cells, e.g. human cells.

"HBV" as used herein refers to any HBV. In some embodiments, a HBV is a HBV of serotype adr, adw, ayr or ayw. In some embodiments, a HBV is a HBV of genotype A, B, C, D, E, F, G, H, I or J (see e.g. Sunbul, World J Gastroenerol (2014) 20(18): 5427-5434). In particular embodiments, the HBV genotype is B or C.

As used herein a "peptide" refers to a chain of two or more amino acid monomers linked by peptide bonds. In some embodiments a peptide may be 50 amino acids or fewer in length. A "polypeptide" as used herein refers to a chain of two or more peptides linked by peptide bonds.

TCR and Cell Therapies (e.g. T Cell Therapies)

The TCRs of the present invention may be used in a method of treating a disease or condition in a patient. Patients may be treated with a lymphocyte (e.g. T cell) that express a TCR from the TCR library of the invention, soluble TCRs using the TCR library of the invention, or chimeric TCRs formed using the TCR library of the invention. Also provided is a method of preventing a disease or condition using the TCRs of the invention.

The lymphocytes (e.g. T cells) of the immunotherapy can come from any source known in the art. For example, T cells can be differentiated in vitro from a hematopoietic stem cell population, or T cells can be obtained from a subject. T cells can be obtained from, e.g., peripheral blood mononuclear cells (PBMCs), bone marrow, lymph node tissue, cord blood, thymus tissue, tissue from a site of infection, ascites, pleural effusion, spleen tissue, and tumours. In addition, the T cells can be derived from one or more T cell lines available in the art. T cells can also be obtained from a unit of blood collected from a subject using any number of techniques known to the skilled artisan, such as apheresis. Furthermore, it is anticipated that expression of the TCR in other cell lines, such as NK cells can be used therapeutically.

In some embodiments, the use of the TCRs of the invention in methods of treatment/prevention of diseases/conditions by adoptive cell transfer (ACT) is contemplated. Adoptive cell transfer generally refers to a process by which cells (e.g. immune cells) are obtained from a subject, typically by drawing a blood sample from which the cells are isolated. The cells are then typically modified and/or expanded, and then administered either to the same subject (in the case of adoptive transfer of autologous/autogeneic cells) or to a different subject (in the case of adoptive transfer of allogeneic cells). The treatment is typically aimed at providing a population of cells with certain desired characteristics to a subject, or increasing the frequency of such cells with such characteristics in that subject. Adoptive transfer may be performed with the aim of introducing a cell or population of cells into a subject, and/or increasing the frequency of a cell or population of cells in a subject. T cells can be engineered to express T cell receptor (TCR) from the TCR library of the invention.

Adoptive transfer of immune cells is described, for example, in Kalos and June 2013, Immunity 39(1): 49-60, and Davis et al. 2015, Cancer J. 21(6): 486-491, both of which are hereby incorporated by reference in their entirety. The skilled person is able to determine appropriate reagents and procedures for adoptive transfer of cells according to the present disclosure, for example by reference to Dai et al., 2016 J Nat Cancer Inst 108(7): djv439, which is incorporated by reference in its entirety.

In some embodiments, the subject from which the immune cells are isolated is the same subject to which cells are administered (i.e., adoptive transfer may be of autologous/autogeneic cells). In some embodiments, the subject from which the immune cells are isolated is a different subject to the subject to which cells are administered (i.e., adoptive transfer may be of allogeneic cells).

It will be appreciated that the therapeutic and prophylactic utility of the populations of cells generated in accordance with the present disclosure extends to the treatment/prevention of any disease/condition that would derive therapeutic or prophylactic benefit from a reduction in HBV/HDV load, and/or the number/activity of cells infected with HBV/HDV.

The methods may be effective to reduce the development/progression of a disease/condition, alleviate the symptoms of a disease/condition or lead to a reduction in the pathology of a disease/condition. The methods may be effective to prevent progression of the disease/condition, e.g. to prevent worsening of, or to slow the rate of development of, the disease/condition. In some embodiments the methods may lead to an improvement in the disease/condition, e.g. a reduction in the symptoms of the disease/condition or reduction in some other correlate of the severity/activity of the disease/condition. In some embodiments the methods may prevent development of the disease/condition a later stage (e.g. a chronic stage or metastasis).

Other Lymphocytes

The term "lymphocyte" includes T cells, B cells, natural killer (NK) cells and natural killer T (NKT) cells. NK cells are a type of cytotoxic (cell toxic) lymphocyte that represent a major component of the inherent immune system. NK cells reject tumors and cells infected by viruses. It works through the process of apoptosis or programed cell death. They were originally termed "natural killers" because they do not require activation in order to kill cells. NKT cells are a heterogeneous group of T cells that share properties of both T cells and natural killer (NK) cells. In contrast to conventional T cells, NKTs are functionally mature when they exit the thymus, primed for rapid cytokine production. TCRs of the disclosed TCR library can be readily expressed by T cells, or NK cells, and/or NK T cells via standard molecular biology techniques.

Subjects

The subject in accordance with aspects the invention described herein may be any animal or human. The subject is preferably mammalian, more preferably human. The subject may be a non-human mammal, but is more preferably human. The subject may be male or female. The subject may be a patient. A subject may have been diagnosed with a disease or condition requiring treatment (e.g. a cancer, an infectious disease or an autoimmune disease), may be suspected of having such a disease/condition, or may be at risk of developing/contracting such a disease/condition.

In embodiments according to the present invention the subject is preferably a human subject. In some embodiments, the subject to be treated according to a therapeutic or prophylactic method of the invention herein is a subject having, or at risk of developing, a disease/condition. In embodiments according to the present invention, a subject may be selected for treatment according to the methods based on characterisation for certain markers of such a disease/condition.

Pharmaceutical Compositions

The TCRs of the present invention and/or T cells transfected with TCRs of the present invention may be provided in a pharmaceutical composition together with a pharmaceutically acceptable carrier. In some embodiments the TCRs may be a soluble TCR and/or a chimeric TCR. The term "pharmaceutically acceptable carrier" refers to a carrier for use in administering the therapeutic agents. The pharmaceutical composition can be in any appropriate form (depending upon the desired method of administration to a patient). It can be provided in unit dosage form, generally provided in a sealed container, and can be provided as part of a kit. The kit may include a plurality of said unit dosage forms. Also provided is an isolated population of cells comprising the TCR of the invention as a pharmaceutical composition.

The features disclosed in the foregoing description, or in the following claims, expressed in their specific forms or in terms of a means for performing the disclosed function, or a method or process for obtaining the disclosed results, as appropriate, may, separately, or in any combination of such features, be utilised for realising the invention in diverse forms thereof.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

For the avoidance of any doubt, any theoretical explanations provided herein are provided for the purposes of improving the understanding of a reader. The inventors do not wish to be bound by any of these theoretical explanations.

Any section headings used herein are for organizational purposes only and are not to be construed as limiting the subject matter described.

Throughout this specification, including the claims which follow, unless the context requires otherwise, the word "comprise" and "include", and variations such as "comprises", "comprising", and "including" will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means for example+/−10%.

NUMBERED EMBODIMENTS OF THE INVENTION

1. A library of T cell receptors (TCRs), wherein the library includes one or more TCRs that have a CDR3a/CDR3b pairing selected from the following list:

CDR3a: (SEQ ID NO: 1)
AETLDNYGQNFV
and

CDR3b: (SEQ ID NO: 18)
SAVDRDEPFHSNQPQH;

CDR3a: (SEQ ID NO: 2)
ATWLSGSARQLTF
and

CDR3b: (SEQ ID NO: 19)
ASSNRASSYNEQF;

CDR3a: (SEQ ID NO: 3)
AVNLYAGNMLT
and

CDR3b: (SEQ ID NO: 20)
ASSSDFGNQPQH;

CDR3a: (SEQ ID NO: 4)
CGADRGGGKLIF
and

-continued

CDR3b: (SEQ ID NO: 21)
CASSLFKGADTQYF;

CDR3a: (SEQ ID NO: 5)
CAYRSGLNNDMRF
and

CDR3b: (SEQ ID NO: 22)
CASSLELAGPWGNEQFF;

CDR3a: (SEQ ID NO: 6)
AVSDNQGGKLI
and

CDR3b: (SEQ ID NO: 23)
ASSLSAAYEQY;

CDR3a: (SEQ ID NO: 7)
CAVRYNNARLMF
and

CDR3b: (SEQ ID NO: 24)
CSAPAGMGYEQYF;

CDR3a: (SEQ ID NO: 8)
CVVNGVDSSYKLIF
and

CDR3b: (SEQ ID NO: 25)
CASEMAGGGDNYGYTF;

CDR3a: (SEQ ID NO: 9)
CLVGDEDTGRRALTF
and

CDR3b: (SEQ ID NO: 26)
CASSFSGKASYYEQYF;

CDR3a: (SEQ ID NO: 10)
CAVRDQTGANNLFF
and

CDR3b: (SEQ ID NO: 27)
CASSPEPTSGSFNEQFF;

CDR3a: (SEQ ID NO: 11)
CAVNMVAGNMLTF
and

CDR3b: (SEQ ID NO: 28)
CASSPDSSGANVLTF;

CDR3a: (SEQ ID NO: 12)
CAVDGNNRLAF
and

CDR3b: (SEQ ID NO: 29)
CSVDMDWGIGGYTF;

CDR3a: (SEQ ID NO: 13)
CAGAGYGGSQGNLIF
and

-continued

CDR3b:
(SEQ ID NO: 30)
CASSIAGGAEQYF;

CDR3a:
(SEQ ID NO: 14)
CAYIGNAGNMLTF
and

CDR3b:
(SEQ ID NO: 31)
CASSLSYRGLGEQFF;

CDR3a:
(SEQ ID NO: 15)
CAVYHTGFQKLVF
and

CDR3b:
(SEQ ID NO: 32)
CASSSRQGGTYEQYF;

CDR3a:
(SEQ ID NO: 16)
CAESMGDFNKFYF
and

CDR3b:
(SEQ ID NO: 33)
CASSPGEGNQPQHF;

CDR3a:
(SEQ ID NO: 17)
CAVSTNFGNEKLTF
and

CDR3b:
(SEQ ID NO: 34)
CASSASLADNTGELFF,

CDR3a:
(SEQ ID NO: 151)
CAESTGGSYIPTF
and

CDR3b:
(SEQ ID NO: 160)
CASASDSDDEKLFF,

CDR3a:
(SEQ ID NO: 152)
CAVNAPGGYNKLIF
and

CDR3b:
(SEQ ID NO: 161)
CASSISQGGYGYTF,

CDR3a:
(SEQ ID NO: 153)
CAVERPTGGYNKLIF
and

CDR3b:
(SEQ ID NO: 162)
CASSPGTDYEQYF,

CDR3a:
(SEQ ID NO: 154)
CAVEDYGQNFVF
and

CDR3b:
(SEQ ID NO: 163)
CSARDLSGRSLDTQYF,

CDR3a:
(SEQ ID NO: 155)
CALSDSSGGSYIPTF
and

-continued

CDR3b:
(SEQ ID NO: 164)
CASSLGRQTNTEAFF,

CDR3a:
(SEQ ID NO: 156)
CAACYSGYALNF
and

CDR3b:
(SEQ ID NO: 165)
CASSYRPKLDTEAFF,

CDR3a:
(SEQ ID NO: 157)
CAVVTNDYKLSF
and

CDR3b:
(SEQ ID NO: 166)
CASSQDLGQGSDTQYF,

CDR3a:
(SEQ ID NO: 158)
CAMRSFAQAGTALIF
and

CDR3b:
(SEQ ID NO: 167)
CASSQRGKGQGDEETQYF,

CDR3a:
(SEQ ID NO: 159)
CAGWISPQGAQKLVF
and

CDR3b:
(SEQ ID NO: 168)
CASSLSTNTEAFF, and/or wherein the TCR library includes one or more TCRs that have CDR3a and CDR3b sequences corresponding to a pairing set forth in the above list, in which one or two amino acids are replaced with another amino acid.

2. The TCR library according to embodiment 1, wherein the library includes one or more TCRs which have the CDR3a and CDR3b sequences, and the MHC restriction, as shown in Table 3, or wherein the library includes one or more TCRs that have the MHC restriction and the CDR sequences corresponding to the CDRs as shown in Table 3, in which one or two amino acids of the TCR are replaced with another amino acid.

3. The TCR library according to embodiment 1 or 2, wherein the TCR library includes one or more TCRs that are restricted to an HLA-A molecule of subtype HLA-A*02, HLA-A*11, HLA-A*68, or HLA-A*24; and/or wherein the TCR library includes one or more TCRs that are restricted to an HLA-B molecule of subtype HLA-B*07, HLA-B*15, HLA-B*39, HLA-B*40, HLA-B*58, HLA-B*44, HLA-B*35, HLA-B*55; and/or wherein the TCR library includes one or more TCRs that are restricted to an HLA-C molecule of subtype HLA-C*03, HLA-C*07, HLA-C*08 or HLA-C*12.

4. The TCR library according to any one of embodiments 1-3, wherein the TCR library includes one or more TCRs that have a CDR3a sequence comprising an amino acid motif selected from the following list: DNYG (SEQ ID NO:117), KLI (SEQ ID NO:118), LTF (SEQ ID NO:122), AGNMLT (SEQ ID NO:123), GGKLI (SEQ ID NO:125), CAV (SEQ ID NO:126), GGS (SEQ ID NO:193), and NxRLzF (SEQ ID NO:128), wherein the x in NxRLzF (SEQ ID NO:128) is arginine (R) or alanine (A) and the z in NxRLzF (SEQ ID NO:128) is methionine (M) or alanine (A);

and/or wherein the TCR library includes one or more TCRs that have a CDR3b sequence comprising an amino acid motif selected from the following list: NQPQH (SEQ ID NO:133), ASS (SEQ ID NO:134), EQFF (SEQ ID NO:139), QYF (SEQ ID NO:141), EQ (SEQ ID NO:142), GYTF (SEQ ID NO:150) and TEAFF (SEQ ID NO:192).

5. The TCR library according to any one of the preceding embodiments, wherein the library includes two or more TCRs selected from Table 2, or wherein the library includes two or more TCRs that have CDR sequences corresponding to the CDRs of a TCR set forth in Table 2, wherein one or two amino acids of the CDRs of the TCR as set forth in the table may be replaced with another amino acid in the TCRs of the library.

6. The TCR library according to embodiment 5, wherein the TCR library includes one or more TCRs that have a CDR1 a sequence comprising an amino acid motif selected from the following list: DSSSTY (SEQ ID NO:58), SQS (SEQ ID NO:87), TSESDYY (SEQ ID NO:62), SVFSS (SEQ ID NO:67), and SxNN (SEQ ID NO:84), wherein the x in SxNN (SEQ ID NO:84) is isoleucine (I) or valine (V);

and/or wherein the TCR library includes one or more TCRs that have a CDR1 b sequence comprising an amino acid motif selected from the following list: DFQATT (SEQ ID NO:72), SG (SEQ ID NO:95), GHN (SEQ ID NO:102), and MxHEz (SEQ ID NO:97), wherein the x in MxHEz (SEQ ID NO:97) is asparagine (N) or aspartic acid (D) and wherein the z in MxHEz (SEQ ID NO:97) is asparagine (N) or tyrosine (Y);

and/or wherein the TCR library includes one or more TCRs that have a CDR2a sequence comprising an amino acid motif selected from the following list: SN (SEQ ID NO:104), GGE (SEQ ID NO:107), YK (SEQ ID NO:109), and GEE (SEQ ID NO:111);

and/or wherein the TCR library includes one or more TCRs that have a CDR2b sequence comprising an amino acid motif selected from the following list: SNEGSKA (SEQ ID NO:47), FNNNVP (SEQ ID NO:48), FQN (SEQ ID NO:179), SYDVKM (SEQ ID NO:50), and SMNVEV (SEQ ID NO:52).

7. A TCR selected from the TCR library according to any one of the preceding embodiments.

8. An isolated nucleic acid encoding the alpha and/or beta chain of TCR according to embodiment 7.

9. The isolated nucleic acid according to embodiment 8, wherein the nucleic acid encodes both the alpha and beta chain.

10. The isolated nucleic acid according to embodiment 9, wherein the nucleic acid comprises:

(a) a nucleic acid sequence encoding a TCR α-chain comprising a variable region and a constant region;

(b) a nucleic acid sequence encoding a TCR β-chain comprising a variable region and a constant region; and (c) a nucleic acid sequence encoding a cleavable linker, wherein sequence (c) is located in the isolated nucleic acid between sequences (a) and (b), and wherein sequences (a), (b) and (c) are in the same reading frame.

11. A pair of isolated nucleic acids, each according to embodiment 8, wherein a first member of the pair encodes the alpha chain and wherein a second member of the pair encodes the beta chain.

12. A vector comprising the nucleic acid or nucleic acids according to any one of embodiments 8-11.

13. A library of isolated nucleic acids according to embodiments 8-11, or of vectors according to embodiment 12, wherein the library of nucleic acids or vectors encodes a TCR library according to any one of embodiments 1-6.

14. A method of producing a T cell that is capable of participating in an immune reaction against an HBV infected cell, an HBV/HDV co-infected cell, and/or against a transformed cell that expresses an HBV antigen, the method comprising introducing a nucleic acid according to any one of embodiments 8-11 or a vector according to embodiment 12 into a recipient T cell or T cell precursor and then propagating the recipient T cell or T cell precursor.

15. The method according to embodiment 14, wherein recipient T cell or T cell precursor has been obtained from a patient who has, or had, or is at risk of contracting an HBV infection, an HDV infection, and/or a hepatocellular carcinoma.

16. The method according to embodiment 15, wherein the nucleic acid or vector is introduced into the recipient T cell or T cell precursor by electroporation.

17. The method according to embodiment 15 or embodiment 16, wherein the recipient T cell is an activated T cell.

18. A method of selecting a patient for treatment, wherein the method comprises determining the HLA-A haplotype, the HLA-B haplotype, and/or the HLA-C haplotype of the patient, and then selecting a TCR from a TCR library according to any one of embodiments 1-6, wherein the selected TCR is restricted to an HLA-A, HLA-B, and/or HLA-C molecule expressed by the patient.

19. The method according to embodiment 18, wherein the patient has, or had, or is at risk of contracting an HBV infection, an HDV infection, and/or a hepatocellular carcinoma.

20. The method according to embodiment 18 or embodiment 19, wherein the method further comprises detecting an HBV antigen and/or an HBV nucleic acid fragment in a sample that has been taken from the patient prior to selecting the TCR from the TCR library.

21. The method according to any one of embodiments 18-20, wherein the patient has not received a liver transplant.

22. The method according to any one of embodiments 18-20, wherein the patient has received, or is scheduled to receive, a liver transplant.

23. The method according to embodiment 22, wherein the method further comprises determining the HLA-A haplotype, the HLA-B haplotype, and/or the HLA-C haplotype of the transplanted liver.

24. A method of treating a patient that has been selected by the method of any one of embodiments 18-23, the method comprising administering to the patient a T cell that expresses the selected TCR.

25. The method according to embodiment 24, wherein the T cell is administered via intravenous infusion.

26. The method according to embodiment 24, wherein the T cell is administered via intra-tumoral injection.

27. The method according to embodiment 24, wherein the T cell is administered via intra-arterial injection.

28. The method according to any one of embodiments 24-27, wherein the T cell that expresses the TCR selected from the library has been produced by introducing a nucleic acid according to any one of embodiments 8-11 or a vector according to embodiment 12 into an autologous T cell that had been harvested from the patient.

29. The method according to any one of embodiments 24-28, wherein the patient has been diagnosed with recurrent HBV-related HCC.

30. The method according to any one of embodiments 24-29, wherein the patient has received, or is scheduled to receive, a liver transplant.

31. A T cell that expresses a TCR from the TCR library according to any one of embodiments 1-6.

32. The T cell according to embodiment 31, wherein the T cell also expresses a further endogenous TCR that is not from the TCR library.

33. The T cell according to embodiment 31 or embodiment 32, wherein the T cell is a CD8+ T cell.

34. The T cell according to any one of embodiments 31-33 for use in medicine.

35. The T cell according to any one of embodiments 31-33 for use in a method of treating a patient that has been selected by the method of any one of embodiments 18-23, the method comprising administering the T cell to the patient.

36. The T cell for the use according to embodiment 35, wherein the T cell is administered via intravenous infusion.

37. The T cell for the use according to embodiment 35 or embodiment 36, wherein the T cell has been produced by introducing a nucleic acid according to any one of embodiments 8-11 or a vector according to embodiment 12 into an autologous T cell that had been harvested from the patient.

38. The T cell for the use according to any one of embodiments 35-37, wherein the patient has been diagnosed with recurrent HBV-related HCC.

39. The T cell for the use according to any one of embodiments 35-38, wherein the patient has received, or is scheduled to receive, a liver transplant.

40. Use of the T cell according to any one of embodiments 31-33 in the manufacture of a medicament for treating a patient that has been selected by the method of any one of embodiments 18-23.

41. Use of the TCR according to embodiment 7 in the manufacture of a medicament for treating a patient that has been selected by the method of any one of embodiments 18-23.

42. The use according to embodiment 40, wherein the T cell is administered to the patient via intravenous infusion.

43. The use according to embodiment 40 or embodiment 42, wherein the T cell has been produced by introducing a nucleic acid according to any one of embodiments 8-11 or a vector according to embodiment 12 into an autologous T cell that had been harvested from the patient.

44. The use according to any one of embodiments 40-43, wherein the patient has been diagnosed with recurrent HBV-related HCC.

45. The use according to any one of embodiments 40-44, wherein the patient has received, or is scheduled to receive, a liver transplant.

Sequences of the Invention

The invention may include one or more TCRs comprising one or more of the sequences recited herein, for instance as set forth in Table 4:

TABLE 4

Sequences of the invention

| Sequence identifier (SEQ ID NO) | Sequence type | Amino acid sequence |
|---|---|---|
| 1 | TCR CDR3a | AETLDNYGQNFV |
| 2 | TCR CDR3a | ATWLSGSARQLTF |
| 3 | TCR CDR3a | AVNLYAGNMLT |
| 4 | TCR CDR3a | CGADRGGGKLIF |
| 5 | TCR CDR3a | CAYRSGLNNDMRF |
| 6 | TCR CDR3a | AVSDNQGGKLI |
| 7 | TCR CDR3a | CAVRYNNARLMF |
| 8 | TCR CDR3a | CVVNGVDSSYKLIF |
| 9 | TCR CDR3a | CLVGDEDTGRRALTF |
| 10 | TCR CDR3a | CAVRDQTGANNLFF |
| 11 | TCR CDR3a | CAVNMVAGNMLTF |
| 12 | TCR CDR3a | CAVDGNNRLAF |
| 13 | TCR CDR3a | CAGAGYGGSQGNLIF |
| 14 | TCR CDR3a | CAYIGNAGNMLTF |
| 15 | TCR CDR3a | CAVYHTGFQKLVF |
| 16 | TCR CDR3a | CAESMGDFNKFYF |
| 17 | TCR CDR3a | CAVSTNFGNEKLTF |
| 18 | TCR CDR3b | SAVDRDEPFHSNQPQH |
| 19 | TCR CDR3b | ASSNRASSYNEQF |
| 20 | TCR CDR3b | ASSSDFGNQPQH |
| 21 | TCR CDR3b | CASSLFKGADTQYF |
| 22 | TCR CDR3b | CASSLELAGPWGNEQFF |
| 23 | TCR CDR3b | ASSLSAAYEQY |
| 24 | TCR CDR3b | CSAPAGMGYEQYF |
| 25 | TCR CDR3b | CASEMAGGGDNYGYTF |
| 26 | TCR CDR3b | CASSFSGKASYYEQYF |
| 27 | TCR CDR3b | CASSPEPTSGSFNEQFF |
| 28 | TCR CDR3b | CASSPDSSGANVLTF |
| 29 | TCR CDR3b | CSVDMDWGIGGYTF |
| 30 | TCR CDR3b | CASSIAGGAEQYF |
| 31 | TCR CDR3b | CASSLSYRGLGEQFF |
| 32 | TCR CDR3b | CASSSRQGGTYEQYF |
| 33 | TCR CDR3b | CASSPGEGNQPQHF |
| 34 | TCR CDR3b | CASSASLADNTGELFF |
| 35 | TCR CDR2a | IFSNMDM |
| 36 | TCR CDR2a | IRSNERE |
| 37 | TCR CDR2a | IYSNGD |

TABLE 4-continued

| Sequences of the invention | | |
|---|---|---|
| Sequence identifier (SEQ ID NO) | Sequence type | Amino acid sequence |
| 38 | TCR CDR2a | LQKGGEE |
| 39 | TCR CDR2a | QEAYKQQN |
| 40 | TCR CDR2a | YLSGSTLV |
| 41 | TCR CDR2a | NVLDGL |
| 42 | TCR CDR2a | VYSSGN |
| 43 | TCR CDR2a | GYKTK |
| 44 | TCR CDR2a | VVTGGEV |
| 45 | TCR CDR2a | IPSGT |
| 46 | TCR CDR2a | LYSAGEE |
| 47 | TCR CDR2b | SNEGSKA |
| 48 | TCR CDR2b | FNNNVP |
| 49 | TCR CDR2b | FQNEAQ |
| 50 | TCR CDR2b | SYDVKM |
| 51 | TCR CDR2b | FQNNGV |
| 52 | TCR CDR2b | SMNVEV |
| 53 | TCR CDR2b | YNFKEQ |
| 54 | TCR CDR2b | FQGTGA |
| 55 | TCR CDR2b | ANQGSEA |
| 56 | TCR CDR2b | SQIVND |
| 57 | TCR CDR2b | YYNGEE |
| 58 | TCR CDR1a | DSSSTY |
| 59 | TCR CDR1a | TSINN |
| 60 | TCR CDR1a | DRGSQS |
| 61 | TCR CDR1a | KTLYG |
| 62 | TCR CDR1a | TSESDYY |
| 63 | TCR CDR1a | SSVSVY |
| 64 | TCR CDR1a | TSGFNG |
| 65 | TCR CDR1a | NSASQS |
| 66 | TCR CDR1a | NIATNDY |
| 67 | TCR CDR1a | SVFSS |
| 68 | TCR CDR1a | DSVNN |
| 69 | TCR CDR1a | VSGLRG |
| 70 | TCR CDR1a | DRVSQS |
| 71 | TCR CDR1a | DISSTY |
| 72 | TCR CDR1b | DFQATT |
| 73 | TCR CDR1b | SGHDY |

TABLE 4-continued

| Sequences of the invention | | |
|---|---|---|
| Sequence identifier (SEQ ID NO) | Sequence type | Amino acid sequence |
| 74 | TCR CDR1b | SGHVS |
| 75 | TCRCDRIb | MDHEN |
| 76 | TCR CDR1b | SGHAT |
| 77 | TCR CDR1b | SGHNS |
| 78 | TCR CDR1b | MNHEY |
| 79 | TCR CDR1b | LGHNA |
| 80 | TCR CDR1b | SGHTA |
| 81 | TCR CDR1b | SQVTM |
| 82 | TCRCDRIb | LNHDA |
| 83 | TCR CDR1b | SGDLS |
| 84 | TCR motif | SxNN (x is any amino acid residue) |
| 85 | TCR motif | SINN |
| 86 | TCR motif | SVNN |
| 87 | TCR motif | SQS |
| 89 | TCR motif | DRxSQS (x is any amino acid residue) |
| 90 | TCR motif | DRGSQS |
| 91 | TCR motif | DRVSQS |
| 92 | TCR motif | SV |
| 93 | TCR motif | SVFSS |
| 94 | TCR motif | DFQATT |
| 95 | TCR motif | SG |
| 96 | TCR motif | SGH |
| 97 | TCR motif | MxHEz (x and z are independently any amino acid residue) |
| 98 | TCR motif | MNHEz (z is any amino acid residue) |
| 99 | TCR motif | MDHEz (z is any amino acid residue) |
| 100 | TCR motif | MxHEN (x is any amino acid residue) |
| 101 | TCR motif | MxHEY (x is any amino acid residue) |
| 102 | TCR motif | GHN |
| 103 | TCR motif | SGHN |

TABLE 4-continued

Sequences of the invention

| Sequence identifier (SEQ ID NO) | Sequence type | Amino acid sequence |
|---|---|---|
| 104 | TCR motif | SN |
| 105 | TCR motif | IFSNMDM |
| 106 | TCR motif | IYSNGD |
| 107 | TCR motif | GGE |
| 108 | TCR motif | VVTGGEV |
| 109 | TCR motif | YK |
| 110 | TCR motif | QEAYKQQN |
| 111 | TCR motif | GEE |
| 112 | TCR motif | SNEGSKA |
| 113 | TCR motif | FNNNVP |
| 114 | TCR motif | SYDVKM |
| 115 | TCR motif | SMNVEV |
| 116 | TCR motif | DNxG (x is any amino acid residue) |
| 117 | TCR motif | DNYG |
| 118 | TCR motif | KLI |
| 119 | TCR motif | KLxF (x is any amino acid residue) |
| 120 | TCR motif | KLxF |
| 121 | TCR motif | KLIF |
| 122 | TCR motif | LTF |
| 123 | TCR motif | AGNMLT |
| 124 | TCR motif | AGNMLTF |
| 125 | TCR motif | GGKLI |
| 126 | TCR motif | CAV |
| 127 | TCR motif | CAVR |
| 128 | TCR motif | NxRLzF (x and z are independently any amino acid residue) |
| 129 | TCR motif | NRRLzF (z is independently any amino acid residue) |
| 130 | TCR motif | NARLzF (z is independently any amino acid residue) |
| 131 | TCR motif | NxRLMF (x is independently any amino acid residue) |
| 132 | TCR motif | NxRLAF (x is independently any amino acid residue) |
| 133 | TCR motif | NQPQH |
| 134 | TCR motif | ASS |
| 135 | TCR motif | ASSL |
| 136 | TCR motif | ASSS |
| 137 | TCR motif | CASS |
| 138 | TCR motif | CASSL |
| 139 | TCR motif | EQFF |
| 140 | TCR motif | GNQPQH |
| 141 | TCR motif | QYF |
| 142 | TCR motif | EQ |
| 143 | TCR motif | EQYF |
| 144 | TCR motif | YEQYF |
| 145 | TCR motif | EQF |
| 146 | TCR motif | NEQF |
| 147 | TCR motif | NEQFF |
| 148 | TCR motif | EQY |
| 149 | TCR motif | YEQY |
| 150 | TCR motif | GYTF |
| 151 | TCR CDR3a | CAESTGGSYIPTF |
| 152 | TCR CDR3a | CAVNAPGGYNKLIF |
| 153 | TCR CDR3a | CAVERPTGGYNKLIF |
| 154 | TCR CDR3a | CAVEDYGQNFVF |
| 155 | TCR CDR3a | CALSDSSGGSYIPTF |
| 156 | TCR CDR3a | CAACYSGYALNF |
| 157 | TCR CDR3a | CAVVTNDYKLSF |
| 158 | TCR CDR3a | CAMRSFAQAGTALIF |
| 159 | TCR CDR3a | CAGWISPQGAQKLVF |
| 160 | TCR CDR3b | CASASDSDDEKLFF |
| 161 | TCR CDR3b | CASSISQGGYGYTF |
| 162 | TCR CDR3b | CASSPGTDYEQYF |
| 163 | TCR CDR3b | CSARDLSGRSLDTQYF |
| 164 | TCR CDR3b | CASSLGRQTNTEAFF |
| 165 | TCR CDR3b | CASSYRPKLDTEAFF |
| 166 | TCR CDR3b | CASSQDLGQGSDTQYF |

TABLE 4-continued

| Sequences of the invention | | |
|---|---|---|
| Sequence identifier (SEQ ID NO) | Sequence type | Amino acid sequence |
| 167 | TCR CDR3b | CASSQRGKGQGDEETQYF |
| 168 | TCR CDR3b | CASSLSTNTEAFF |
| 169 | TCR CDR2a | YFSGDPLV |
| 170 | TCR CDR2a | IQSSQRE |
| 171 | TCR CDR2a | RNSFDEQN |
| 172 | TCR CDR2a | IRSNVGE |
| 173 | TCR CDR2a | QGSYDEQN |
| 174 | TCR CDR2a | LVKSGEV |
| 175 | TCR CDR2b | FYNNEI |
| 176 | TCR CDR2b | YFSETQ |
| 177 | TCR CDR2b | SVGAGI |
| 178 | TCR CDR2b | YNNKEL |
| 179 | TCR motif | FQN |
| 180 | TCR CDR2b | FNYEAQ |
| 181 | TCR CDR1a | YGGTVN |
| 182 | TCR CDR1a | DSAIYN |
| 183 | TCR CDR1a | TRDTTYY |
| 184 | TCR CDR1a | DSASNY |
| 185 | TCR CDR1a | TSDQSYG |
| 186 | TCR CDR1a | TTLSN |
| 187 | TCR CDR1b | SNHLY |
| 188 | TCR CDR1b | SGHRS |
| 189 | TCR CDR1b | SEHNR |
| 190 | TCRCDRIb | LGHDT |
| 191 | TCR CDR1b | SSHAT |
| 192 | TCR motif | TEAFF |
| 193 | TCR motif | GGS |

EXAMPLES

In Vitro Stimulation of PBMCs

Peripheral blood mononuclear cells (PBMC) were expanded using antigens derived from HBV via a protocol adapted from Tan A T et al 2008 J Virol 82(22):10986-10997, which is hereby specifically incorporated by reference in its entirety.

The procedure is outlined as follows. An aliquot of PBMCs were stimulated with HBV derived antigens. The stimulated PBMCs were then washed and co-cultured with unstimulated PBMCs in the presence of IL-2 to expand target-specific T cells. PHA blasts (antigen presenting cells) were generated from a further PBMC sample stimulated with phytohaemagglutinin (PHA), IL-2, IL-7 and IL-15. The PHA blasts were pulsed with HBV antigen and then irradiated. The stimulated, expanded PBMCs were then incubated with both the irradiated PHA blasts and with irradiated buffy coat-derived PBMC feeder cells.

Identifying T Cell Responders

IFN-Y enzyme-linked immunospot (ELISPOT) assays were performed as previously described (Boni C 2007 J Virol 81(8):4215-4225, which is hereby specifically incorporated by reference in its entirety) using HBV derived antigens. HBV-specific T-cell responses were analyzed in IFN-Y ELISPOT assays using the expanded PBMCs described above or using short-term HBV-specific polyclonal T cell lines expanded for 10 days. Briefly, 96-well plates (Multiscreen-HTS; Millipore, Billerica, MA) were coated overnight at 4° C. with 5 μg/ml capture mouse anti-human IFN-Y mAb (1DIK; Mabtech, Sweden). The plates were washed with phosphate-buffered saline (PBS) and blocked with AIM-V supplemented with 10% heat-inactivated fetal calf serum for 30 min at room temperature. The wells were seeded with the expanded PBMCs described above or using short-term HBV-specific polyclonal T cell lines and then incubated in the presence or absence of HBV derived antigens. IFN-Y levels were then assayed using anti-human IFN-Y mAb (7B6-1; Mabtech, Sweden), streptavidin-conjugated alkaline phosphatase (Mabtech, Sweden) and 5-bromo-4-chloro-3-indolyl phosphate—nitro blue tetrazolium chloride [BCIP-NBT] substrate (KPL, Gaithersburg, MD). The number of IFN-Y-producing cells was expressed in spot-forming units (SFU) per $1\times10^5$ cells. The number of specific IFN-Y-secreting cells was calculated by subtracting the non-stimulated control value from the stimulated sample. Positive controls consisted of PBMCs stimulated with phorbol myristate acetate (10 ng/ml) and ionomycin (100 ng/ml).

Assessing Specificity

Every positive ELISPOT response was reconfirmed using IFN-Y intracellular cytokine staining (ICS). Briefly, in vitro expanded PBMCs were stimulated overnight with PHA blasts loaded with HBV antigen in the presence of Brefeldin A. The cells were then stained with labelled anti-CD8, before being washed, fixed, permeabilised and analysed by flow cytometry for IFNγ production. To assess the cytotoxic ability of the in vitro expanded PBMCs, their degranulation activity was assessed using CD107a. Briefly, in vitro expanded PBMCs were stimulated for 5 h with HBV antigen in the presence of Brefeldin A and CD107a antibody. The cells were then washed and labelled with anti-CD8 antibody, before being analysed by flow cytometry for $CD8^+$ $CD107a^+$ positive response.

Determining HLA Restriction of Responding Peptides

The PBMCs tested were HLA typed by BGI (Hong Kong, China). Short-term HBV-specific T cell lines were cocultured with a panel of Epstein-Barr virus (EBV)-transformed B cells (which had one or more HLA class I alleles matching that of the PBMCs) pulsed with HBV antigen. IFN-Y- and CD107a-expressing $CD8^+$ cells were quantified by flow cytometry. The HLA restriction of the CD8+ T cells is indicated by the responsive EBV-transformed B cell line(s). The TCR alpha and beta chain sequences of the CD8+ T cells were determined essentially as described by Banu et al, 2004.

Engineering HBV-Specific TCR-Redirected T Cells

Peripheral blood mononuclear cells (PBMC) from the patient were isolated by Ficoll density gradient centrifugation and PBMC were cryopreserved. Depending on the schedule for infusion, frozen PBMC were thawed on day −9 followed by activation for 8 days with 600 IU/mL of GMP grade IL-2 (Miltenyi) and 50 ng/mL of GMP grade OKT-3 (Miltenyi) in cell therapy grade AIM-V (Invitrogen) supplemented with 5% CTS Serum Replacement (Invitrogen). Activated T cells were then electroporated using the AgilePulse Max system (BTX) with mRNA encoding the selected HBV-specific TCR according to the manufacturer's recommended protocol. After electroporation, cells were left to rest overnight in AIM-V+5% CTS Serum Replacement+100 IU/mL IL-2 at 37° C. and 5% $CO_2$. Quality control experiments were then performed to characterize HBV-specific TCR expression levels and function of the engineered T cells. Electroporation efficiency was quantified by staining with the appropriate TCR-Vβ antibody (Beckman Coulter) and anti-CD8 antibody. To characterize the TCR T-cell function, EBV B cells expressing the appropriate HLA molecules were first pulsed with HBV antigen for 1 hour at 37° C. The TCR T cells were then co-cultured with the pulsed EBV B cells overnight in the presence of 2 µg/mL Brefeldin A before intracellular staining with anti-CD8 and anti-IFN-gamma antibodies. To characterize the TCR T-cell cytotoxic ability, the degranulation activity was assessed using a 5 h CD107a assay, as described above. In addition, the ability of the TCR T-cells to lyse hepatocyte-like cells lines expressing HBV antigens was assessed. Briefly, an xCELLigence real-time cytotoxicity assay was carried out by seeding hepatocyte-like cell lines expressing HBV antigens in xCELLigence E-Plates for 16-18 h, before adding TCR T-cells at varying effector:target ratios, and continuously monitoring the impedance across 3-5 days.

TABLE 5

Functional responses of the TCRs of the library of the invention

| TCR # | MHC restriction tested | IFNg+ response |
|---|---|---|
| 1 | HLA-C*0801 | ++++ |
| 2 | HLA-A*0201 | ++ |
| | HLA-A*0203 | + |
| | HLA-A*0206 | ++ |
| | HLA-A*0207 | ++ |
| 3 | HLA-A*0201 | ++++ |
| | HLA-A*0203 | + |
| | HLA-A*0206 | − |
| | HLA-A*0207 | +++ |
| 4 | HLA-A*0201 | ++++ |
| | HLA-A*0203 | − |
| | HLA-A*0206 | + |
| | HLA-A*0207 | + |
| 5 | HLA-A*1101 | +++ |
| | HLA-A*1102 | +++ |
| 6 | HLA-B*5801/HLA-C*0302 | +++ |
| 7 | HLA-B*5801/HLA-C*0302 | ++++ |
| 8 | HLA-A*0201 | ++ |
| | HLA-A*0203 | + |
| | HLA-A*0206 | + |
| | HLA-A*0207 | + |
| 9 | HLA-B*0706/HLA-B*3915 | + |
| 10 | HLA-A*0201 | +++ |
| | HLA-A*0203 | − |
| | HLA-A*0206 | − |
| | HLA-A*0207 | +++ |
| 11 | HLA-A*0201 | +++ |
| | HLA-A*0203 | − |
| | HLA-A*0206 | − |
| | HLA-A*0207 | ++++ |
| 12 | HLA-A*1101 | ++ |
| | HLA-A*1102 | + |
| 13 | HLA-B*4001 | +++ |

TABLE 5-continued

Functional responses of the TCRs of the library of the invention

| TCR # | MHC restriction tested | IFNg+ response |
|---|---|---|
| 14 | HLA-A*1101 | +++ |
| | HLA-A*1102 | +++ |
| 15 | HLA-B*4040/HLA-C*0822 | + |
| 16 | HLA-A*6802/HLA-B*1510 | +++ |
| 17 | HLA-C*0706 | +++ |
| 18 | HLA-A*2402 | +++ |
| | HLA-A*2407 | +++ |
| 19 | HLA-B*4403 | + |
| 20 | HLA-A*1101 | ++++ |
| | HLA-A*1102 | ++++ |
| 21 | HLA-B*3503 | ++++ |
| | HLA-B*3501 | + |
| 22 | HLA-B*5502 | +++ |
| 23 | HLA-C*1203 | +++ |
| | HLA-C*1202 | + |
| 24 | HLA-C*1203 | + |
| | HLA-C*1202 | − |
| 25 | HLA-B*5801/HLA-C*0302 | + |
| 26 | HLA-A*2402 | ++++ |
| | HLA-A*2407 | ++++ |

TABLE 6

Functional responses of other TCRs

| TCR # | MHC restriction tested | IFNg+ response |
|---|---|---|
| 27 | HLA-A*1101 | − |
| | HLA-A*1102 | − |
| 28 | HLA-A*1101 | − |
| | HLA-A*1102 | − |
| 29 | HLA-C*0304 | − |
| 30 | HLA-A*2402 | − |
| 31 | HLA-A*2402 | − |

Infusion of HBV-Specific TCR-Redirected T Cells

HBV-specific TCR T cells were calculated based on study subject's body weight, frequency of $CD8^+$ TCR-$V\beta^+$ cells out of total viable cells, and the specific dose level assigned based on the clinical protocol. The cells were resuspended in 5% Albutein (Grifols, Barcelona, Spain) and given as a single intravenous infusion in a total volume of 60 mL.

Successful T Cell Immunotherapy

The inventors have demonstrated efficient production of HBV-specific TCR T cells from liver-transplanted patients, and demonstrated of the safety and efficacy of immunotherapy with an autologous HBV-specific TCR T-cell (Tan et al, 2019). In particular, the levels of the soluble tumour marker AFP were found to decline during treatment with a T cell immunotherapy using autologous T cells transiently expressing a TCR chosen for immunological compatibility. T cell expression of the selected TCR had been achieved by electroporation. Most of the pulmonary metastasis decreased in size, with one completely disappearing without recurrence. (A second patient, who received fewer doses and had an advanced cancer with metastases in the bone, did not respond and pulled out of the study.)

This demonstrates the utility of the 'personalised treatments' that are provided by the present invention. A key inventive contribution of the present invention is the provision of a wide range of characterised TCRs that enable such personalised treatments to be made available to a broad population of subjects, having very diverse HLA haplotypes.

Dosing for Recurrent HBV-Related HCC Post Liver Transplantation

The primary objective is to assess the safety and tolerability of HBV-specific TCR T cells in subjects with recurrent HBV-related HCC post liver transplantation. Cells will be given as a intravenous infusion on Day 1, Day 8, Day 15 and Day 22 of the first 28-day treatment cycle, followed by every 2-week dosing on Day 1, Day 15, Day 29 and Day 43 of repeated 56-day cycle. A 21-day treatment break will be given between each cycle. Escalating doses of $1\times10^4$ kg, $1\times10^5$ kg, $1\times10^6$ kg, $5\times10^6$ kg (±25%) TCR T cells weekly during the first cycle. If the doses were adequately tolerant during the first cycle, subjects will receive doses of $5\times10^6$/kg (±25%) TCR T cells in every 2-week dosing cycle until disease progression, unacceptable toxicity, or other reason for treatment discontinuation.

REFERENCES

A number of publications are cited above in order to more fully describe and disclose the invention and the state of the art to which the invention pertains. Full citations for these references are provided below. The entirety of each of these references is incorporated herein.

Banu et al, "Building and Optimizing a Virus-specific T Cell Receptor Library for Targeted Immunotherapy in Viral Infections" *Scientific Reports,* 4:4166, 2014

Tan et al, "Use of Expression Profiles of HBV-DNA Integrated Into Genomes of Hepatocellular Carcinoma Cells to Select T Cells for Immunotherapy" *Gastroenterology,* 2019

Thakkar and Bailey-Kellogg, "Balancing sensitivity and specificity in distinguishing TCR groups by CDR sequence similarity" *BMC Bioinformatics* 2019

Smith et al, "Changing the peptide specificity of a human T-cell receptor by directed evolution" Nature Communications 2014

Wei & Orr, "Patterns of HLA class I gene expression" *Encyclopedia of Immunology* (second edition), 1998

Ian Graber-Stiehl, "The silent epidemic killing more people than HIV, malaria or TB" *Nature* 564; pp 24-27, 2018

Cohen, "Forgotten no more" *Science* 362; 6418, 2018

Walseng et al, "Soluble T-cell Receptors Produced in Human Cells for Targeted Delivery" *PLOS One*, e0119559

Walseng et al, "A TCR-based Chimeric Antigen Receptor" *Scientific Reports,* 7:10713

For standard molecular biology techniques, see Sambrook, J., Russel, D. W. *Molecular Cloning, A Laboratory Manual.* 3 ed. 2001, Cold Spring Harbor, New York: Cold Spring Harbor Laboratory Press

The invention claimed is:

1. A library of T cell receptors (TCRs), wherein the TCR library comprises at least 26 TCRs, wherein the TCR library includes TCRs that have CDR3a and CDR3b sequences that respectively correspond to each CDR3a/CDR3b pairing of the following list:

CDR3a: (SEQ ID NO: 1)
AETLDNYGQNFV
and
CDR3b: (SEQ ID NO: 18)
SAVDRDEPFHSNQPQH;

CDR3a: (SEQ ID NO: 2)
ATWLSGSARQLTF
and
CDR3b: (SEQ ID NO: 19)
ASSNRASSYNEQF;

CDR3a: (SEQ ID NO: 3)
AVNLYAGNMLT
and
CDR3b: (SEQ ID NO: 20)
ASSSDFGNQPQH;

CDR3a: (SEQ ID NO: 4)
CGADRGGGKLIF
and
CDR3b: (SEQ ID NO: 21)
CASSLFKGADTQYF;

CDR3a: (SEQ ID NO: 5)
CAYRSGLNNDMRF
and
CDR3b: (SEQ ID NO: 22)
CASSLELAGPWGNEQFF;

CDR3a: (SEQ ID NO: 6)
AVSDNQGGKLI
and
CDR3b: (SEQ ID NO: 23)
ASSLSAAYEQY;

CDR3a: (SEQ ID NO: 7)
CAVRYNNARLMF
and
CDR3b: (SEQ ID NO: 24)
CSAPAGMGYEQYF;

CDR3a:

-continued (SEQ ID NO: 8)
CVVNGVDSSYKLIF
and
CDR3b: (SEQ ID NO: 25)
CASEMAGGGDNYGYTF;

CDR3a: (SEQ ID NO: 9)
CLVGDEDTGRRALTF
and
CDR3b: (SEQ ID NO: 26)
CASSFSGKASYYEQYF;

CDR3a: (SEQ ID NO: 10)
CAVRDQTGANNLFF
and
CDR3b: (SEQ ID NO: 27)
CASSPEPTSGSFNEQFF;

CDR3a: (SEQ ID NO: 11)
CAVNMVAGNMLTF
and
CDR3b: (SEQ ID NO: 28)
CASSPDSSGANVLTF;

CDR3a: (SEQ ID NO: 12)
CAVDGNNRLAF
and
CDR3b: (SEQ ID NO: 29)
CSVDMDWGIGGYTF;

CDR3a: (SEQ ID NO: 13)
CAGAGYGGSQGNLIF
and
CDR3b: (SEQ ID NO: 30)
CASSIAGGAEQYF;

CDR3a: (SEQ ID NO: 14)
CAYIGNAGNMLTF
and
CDR3b: (SEQ ID NO: 31)
CASSLSYRGLGEQFF;

CDR3a: (SEQ ID NO: 15)
CAVYHTGFQKLVF
and
CDR3b: (SEQ ID NO: 32)
CASSSRQGGTYEQYF;

CDR3a:

-continued (SEQ ID NO: 16)
CAESMGDFNKFYF
and

CDR3b:
(SEQ ID NO: 33)
CASSPGEGNQPQHF;

CDR3a:
(SEQ ID NO: 17)
CAVSTNFGNEKLTF
and

CDR3b:
(SEQ ID NO: 34)
CASSASLADNTGELFF,

CDR3a:
(SEQ ID NO: 151)
CAESTGGSYIPTF
and

CDR3b:
(SEQ ID NO: 160)
CASASDSDDEKLFF,

CDR3a:
(SEQ ID NO: 152)
CAVNAPGGYNKLIF
and

CDR3b:
(SEQ ID NO: 161)
CASSISQGGYGYTF,

CDR3a:
(SEQ ID NO: 153)
CAVERPTGGYNKLIF
and

CDR3b:
(SEQ ID NO: 162)
CASSPGTDYEQYF,

CDR3a:
(SEQ ID NO: 154)
CAVEDYGQNFVF
and

CDR3b:
(SEQ ID NO: 163)
CSARDLSGRSLDTQYF,

CDR3a:
(SEQ ID NO: 155)
CALSDSSGGSYIPTF

-continued and

CDR3b:
(SEQ ID NO: 164)
CASSLGRQTNTEAFF,

CDR3a:
(SEQ ID NO: 156)
CAACYSGYALNF
and

CDR3b:
(SEQ ID NO: 165)
CASSYRPKLDTEAFF,

CDR3a:
(SEQ ID NO: 157)
CAVVTNDYKLSF
and

CDR3b:
(SEQ ID NO: 166)
CASSQDLGQGSDTQYF,

CDR3a:
(SEQ ID NO: 158)
CAMRSFAQAGTALIF
and

CDR3b:
(SEQ ID NO: 167)
CASSQRGKGQGDEETQYF,
and

CDR3a:
(SEQ ID NO: 159)
CAGWISPQGAQKLVF
and (SEQ ID NO: 168)
CDR3b:
CASSLSTNTEAFF, such that each listed CDR3a/CDR3b pairing is present in the TCR library;

and/or wherein the TCR library includes TCRs that have CDR3a and CDR3b sequences that respectively correspond to each pairing set forth in the above list, in which one or two amino acids are replaced with another amino acid, such that each CDR3a/CDR3b pairing is present with up to one or two amino acid substitutions in the TCR library.

2. The TCR library according to claim 1, wherein the TCRs of the TCR library have the CDR3a and CDR3b sequences and the MHC restrictions, as shown the following table:

| TCR | CDR3a/CDR3b | MHC restriction |
|---|---|---|
| 1 | AETLDNYGQNFV (SEQ ID NO: 1)<br>SAVDRDEPFHSNQPQH (SEQ ID NO: 18) | HLA-C*0801 |
| 2 | ATWLSGSARQLTF (SEQ ID NO: 2)<br>ASSNRASSYNEQF (SEQ ID NO: 19) | HLA-A*0201; HLA-A*0203;<br>HLA-A*0206; HLA-A*0207 |
| 3 | AVNLYAGNMLT (SEQ ID NO: 3)<br>ASSSDFGNQPQH (SEQ ID NO: 20) | HLA-A*0201; HLA-A*0203;<br>HLA-A*0206; HLA-A*0207 |
| 4 | CGADRGGGKLIF (SEQ ID NO: 4)<br>CASSLFKGADTQYF (SEQ ID NO: 21) | HLA-A*0201; HLA-A*0203;<br>HLA-A*0206; HLA-A*0207 |
| 5 | CAYRSGLNNDMRF (SEQ ID NO: 5)<br>CASSLELAGPWGNEQFF (SEQ ID NO: 22) | HLA-A*1101; HLA-A*1102 |
| 6 | AVSDNQGGKLI (SEQ ID NO: 6)<br>ASSLSAAYEQY (SEQ ID NO: 23) | HLA-B*5801/HLA-C*0302 |

-continued

| TCR | CDR3a/CDR3b | MHC restriction |
|---|---|---|
| 7 | CAVRYNNARLMF (SEQ ID NO: 7)<br>CSAPAGMGYEQYF (SEQ ID NO: 24) | HLA-B*5801/HLA-C*0302 |
| 8 | CVVNGVDSSYKLIF (SEQ ID NO: 8)<br>CASEMAGGGDNYGYTF (SEQ ID NO: 25) | HLA-A*0201; HLA-A*0203;<br>HLA-A*0206; HLA-A*0207 |
| 9 | CLVGDEDTGRRALTF (SEQ ID NO: 9)<br>CASSFSGKASYYEQYF (SEQ ID NO: 26) | HLA-B*0706; HLA-B*3915 |
| 10 | CAVRDQTGANNLFF (SEQ ID NO: 10)<br>CASSPEPTSGSFNEQFF (SEQ ID NO: 27) | HLA-A*0201; HLA-A*0203;<br>HLA-A*0206; HLA-A*0207 |
| 11 | CAVNMVAGNMLTF (SEQ ID NO: 11)<br>CASSPDSSGANVLTF (SEQ ID NO: 28) | HLA-A*0201; HLA-A*0203;<br>HLA-A*0206; HLA-A*0207 |
| 12 | CAVDGNNRLAF (SEQ ID NO: 12)<br>CSVDMDWGIGGYTF (SEQ ID NO: 29) | HLA-A*1101; HLA-A*1102 |
| 13 | CAGAGYGGSQGNLIF (SEQ ID NO: 13)<br>CASSIAGGAEQYF (SEQ ID NO: 30) | HLA-B*4001 |
| 14 | CAYIGNAGNMLTF (SEQ ID NO: 14)<br>CASSLSYRGLGEQFF (SEQ ID NO: 31) | HLA-A*1101; HLA-A*1102 |
| 15 | CAVYHTGFQKLVF (SEQ ID NO: 15)<br>CASSSRQGGTYEQYF (SEQ ID NO: 32) | HLA-B*4040; HLA-C*0822 |
| 16 | CAESMGDFNKFYF (SEQ ID NO: 16)<br>CASSPGEGNQPQHF (SEQ ID NO: 33) | HLA-A*6802; HLA-B*1510 |
| 17 | CAVSTNFGNEKLTF (SEQ ID NO: 17)<br>CASSASLADNTGELFF (SEQ ID NO: 34) | HLA-C*0706 |
| 18 | CAESTGGSYIPTF (SEQ ID NO: 151)<br>CASASDSDDEKLFF (SEQ ID NO: 160) | HLA-A*2401; HLA-A*2402;<br>HLA-A*2407 |
| 19 | CAVNAPGGYNKLIF (SEQ ID NO: 152)<br>CASSISQGGYGYTF (SEQ ID NO: 161) | HLA-B*4403 |
| 20 | CAVERPTGGYNKLIF (SEQ ID NO: 153)<br>CASSPGTDYEQYF (SEQ ID NO: 162) | HLA-A*1101; HLA-A*1102 |
| 21 | CAVEDYGQNFVF (SEQ ID NO: 154)<br>CSARDLSGRSLDTQYF (SEQ ID NO: 163) | HLA-B*3501; HLA-B*3503 |
| 22 | CALSDSSGGSYIPTF (SEQ ID NO: 155)<br>CASSLGRQTNTEAFF (SEQ ID NO: 164) | HLA-B*5502 |
| 23 | CAACYSGYALNF (SEQ ID NO: 156)<br>CASSYRPKLDTEAFF (SEQ ID NO: 165) | HLA-C*1202; HLA-C*1203 |
| 24 | CAVVTNDYKLSF (SEQ ID NO: 157)<br>CASSQDLGQGSDTQYF (SEQ ID NO: 166) | HLA-C*1202; HLA-C*1203 |
| 25 | CAMRSFAQAGTALIF (SEQ ID NO: 158)<br>CASSQRGKGQGDEETQYF (SEQ ID NO: 167) | HLA-B*5801; HLA-C*0302 |
| 26 | CAGWISPQGAQKLVF (SEQ ID NO: 159)<br>CASSLSTNTEAFF (SEQ ID NO: 168) | HLA-A*2401; HLA-A*2402;<br>HLA-A*2407 |

or wherein the TCRs of the TCR library have the MHC restriction and the CDR sequences as shown in the above table, in which one or two amino acids of the CDR sequences are replaced with another amino acid.

3. The TCR library according to claim 1, wherein the TCR library includes fourteen or more TCRs that are restricted to an HLA-A molecule of subtype HLA-A*02, HLA-A*11, HLA-A*68, or HLA-A*24; and/or wherein the TCR library includes eleven or more TCRs that are restricted to an HLA-B molecule of subtype HLA-B*07, HLA-B*15, HLA-B*39, HLA-B*40, HLA-B*58, HLA-B*44, HLA-B*35, or HLA-B*55; and/or wherein the TCR library includes nine or more TCRs that are restricted to an HLA-C molecule of subtype HLA-C*03, HLA-C*07, HLA-C*08, or HLA-C*12.

4. The TCR library according to claim 1, wherein the TCR library includes three or more TCRs that have a CDR3a sequence comprising amino acid motif DNYG (SEQ ID NO:117), and/or six or more TCRs that have a CDR3a sequence comprising amino acid motif KLI (SEQ ID NO:118), and/or six or more TCRs that have a CDR3a sequence comprising amino acid motif LTF (SEQ ID NO:122), and/or four or more TCRs that have a CDR3a sequence comprising amino acid motif AGNMLT (SEQ ID NO: 123), and/or three or more TCRs that have a CDR3a sequence comprising amino acid motif GGKLI (SEQ ID NO:125), and/or eleven or more TCRs that have a CDR3a sequence comprising amino acid motif CAV (SEQ ID NO:126), and/or four or more TCRs that have a CDR3a sequence comprising amino acid motif GGS (SEQ ID NO:193), and/or three or more TCRs that have a CDR3a sequence comprising amino acid motif NxRLzF (SEQ ID NO:128), wherein the x in NxRLzF (SEQ ID NO:128) is arginine (R) or alanine (A) and the z in NxRLzF (SEQ ID NO:128) is methionine (M) or alanine (A);

and/or wherein the TCR library includes four or more TCRs that have a CDR3b sequence comprising amino acid motif NQPQH (SEQ ID NO:133), and/or 21 or more TCRs that have a CDR3b sequence comprising amino acid motif AS(SEQ ID NO:134), and/or four or more TCRs that have a CDR3b sequence comprising amino acid motif EQFF (SEQ ID NO:139), and/or nine or more TCRs that have a CDR3b sequence comprising amino acid motif QYF (SEQ ID NO: 141), and/or ten or more TCRs that have a CDR3b sequence comprising amino acid motif EQ (SEQ ID NO:142), and/or four or more TCRs that have a CDR3b sequence comprising amino acid motif GYTF (SEQ ID NO:150), and/or four or more TCRs that have a CDR3b sequence comprising amino acid motif TEAFF (SEQ ID NO:192).

5. The TCR library according to claim 1, wherein the TCRs of the TCR library have the CDRs shown in the following table:

| TCR, a/b chain | CDR1 | CDR2 | CDR3 |
|---|---|---|---|
| TCR1, α | DSSSTY (SEQ ID NO: 58) | IFSNMDM (SEQ ID NO: 35) | AETLDNYGQNFV (SEQ ID NO: 1) |
| TCR1, β | DFQATT (SEQ ID NO: 72) | SNEGSKA (SEQ ID NO: 47) | SAVDRDEPFHSNQPQH (SEQ ID NO: 18) |
| TCR2, α | TSINN (SEQ ID NO: 59) | IRSNERE (SEQ ID NO: 36) | ATWLSGSARQLTF (SEQ ID NO: 2) |
| TCR2, β | SGHDY (SEQ ID NO: 73) | FNNNVP (SEQ ID NO: 48) | ASSNRASSYNEQF (SEQ ID NO: 19) |
| TCR3, α | DRGSQS (SEQ ID NO: 60) | IYSNGD (SEQ ID NO: 37) | AVNLYAGNMLT (SEQ ID NO: 3) |
| TCR3, β | SGHVS (SEQ ID NO: 74) | FQNEAQ (SEQ ID NO: 49) | ASSSDFGNQPQH (SEQ ID NO: 20) |
| TCR4, α | KTLYG (SEQ ID NO: 61) | LQKGGEE (SEQ ID NO: 38) | CGADRGGGKLIF (SEQ ID NO: 4) |
| TCR4, β | MDHEN (SEQ ID NO: 75) | SYDVKM (SEQ ID NO: 50) | CASSLFKGADTQYF (SEQ ID NO: 21) |
| TCR5, α | TSESDYY (SEQ ID NO: 62) | QEAYKQQ N(SEQ ID NO: 39) | CAYRSGLNNDMRF (SEQ ID NO: 5) |
| TCR5, β | SGHAT (SEQ ID NO: 76) | FQNNGV (SEQ ID NO: 51) | CASSLELAGPWGNEQFF (SEQ ID NO: 22) |
| TCR6, α | SSVSVY (SEQ ID NO: 63) | YLSGSTLV (SEQ ID NO: 40) | AVSDNQGGKLI (SEQ ID NO: 6) |
| TCR6, β | SGHNS (SEQ ID NO: 77) | FNNNVP (SEQ ID NO: 48) | ASSLSAAYEQY (SEQ ID NO: 23) |
| TCR7, α | TSGFNG (SEQ ID NO: 64) | NVLDGL (SEQ ID NO: 41) | CAVRYNNARLMF (SEQ ID NO: 7) |
| TCR7, β | DFQATT (SEQ ID NO: 72) | SNEGSKA (SEQ ID NO: 47) | CSAPAGMGYEQYF (SEQ ID NO: 24) |
| TCR8, α | NSASQS (SEQ ID NO: 65) | VYSSGN (SEQ ID NO: 42) | CVVNGVDSSYKLIF (SEQ ID NO: 8) |

-continued

| TCR, a/b chain | CDR1 | CDR2 | CDR3 |
| --- | --- | --- | --- |
| TCR8, β | MDHEN (SEQ ID NO: 75) | SYDVKM (SEQ ID NO: 50) | CASEMAGGGDNYGYTF (SEQ ID NO: 25) |
| TCR9, α | NIATNDY (SEQ ID NO: 66) | GYKTK (SEQ ID NO: 43) | CLVGDEDTGRRALTF (SEQ ID NO: 9) |
| TCR9, β | MNHEY (SEQ ID NO: 78) | SMNVEV (SEQ ID NO: 52) | CASSFSGKASYYEQYF (SEQ ID NO: 26) |
| TCR10, α | SVFSS (SEQ ID NO: 67) | VVTGGEV (SEQ ID NO: 44) | CAVRDQTGANNLFF (SEQ ID NO: 10) |
| TCR10, β | LGHNA (SEQ ID NO: 79) | YNFKEQ (SEQ ID NO: 53) | CASSPEPTSGSFNEQFF (SEQ ID NO: 27) |
| TCR11, α | DRGSQS (SEQ ID NO: 60) | IYSNGD (SEQ ID NO: 37) | CAVNMVAGNMLTF (SEQ ID NO: 11) |
| TCR11, β | SGHTA (SEQ ID NO: 80) | FQGTGA (SEQ ID NO: 54) | CASSPDSSGANVLTF (SEQ ID NO: 28) |
| TCR12, α | DSVNN (SEQ ID NO: 68) | IPSGT (SEQ ID NO: 45) | CAVDGNNRLAF (SEQ ID NO: 12) |
| TCR12, β | SQVTM (SEQ ID NO: 81) | ANQGSEA (SEQ ID NO: 55) | CSVDMDWGIGGYTF (SEQ ID NO: 29) |
| TCR13, α | SVFSS (SEQ ID NO: 67) | VVTGGEV (SEQ ID NO: 44) | CAGAGYGGSQGNLIF (SEQ ID NO: 13) |
| TCR13, β | LNHDA (SEQ ID NO: 82) | SQIVND (SEQ ID NO: 56) | CASSIAGGAEQYF (SEQ ID NO: 30) |
| TCR14, α | TSESDYY (SEQ ID NO: 62) | QEAYKQQ N(SEQ ID NO: 39) | CAYIGNAGNMLTF (SEQ ID NO: 14) |
| TCR14, β | MNHEY (SEQ ID NO: 78) | SMNVEV (SEQ ID NO: 52) | CASSLSYRGLGEQFF (SEQ ID NO: 31) |
| TCR15, α | VSGLRG (SEQ ID NO: 69) | LYSAGEE (SEQ ID NO: 46) | CAVYHTGFQKLVF (SEQ ID NO: 15) |
| TCR15, β | MDHEN (SEQ ID NO: 75) | SYDVKM (SEQ ID NO: 50) | CASSSRQGGTYEQYF (SEQ ID NO: 32) |
| TCR16, α | DSSSTY (SEQ ID NO: 58) | IFSNMDM (SEQ ID NO: 35) | CAESMGDFNKFYF (SEQ ID NO: 16) |
| TCR16, β | MNHEY (SEQ ID NO: 78) | SMNVEV (SEQ ID NO: 52) | CASSPGEGNQPQHF (SEQ ID NO: 33) |
| TCR17, α | DRVSQS (SEQ ID NO: 70) | IYSNGD (SEQ ID NO: 37) | CAVSTNFGNEKLTF (SEQ ID NO: 17) |
| TCR17, β | SGDLS (SEQ ID NO: 83) | YYNGEE (SEQ ID NO: 57) | CASSASLADNTGELFF (SEQ ID NO: 34) |

-continued

| TCR, a/b chain | CDR1 | CDR2 | CDR3 |
|---|---|---|---|
| TCR18, α | DSSSTY (SEQ ID NO: 58) | IFSNMDM (SEQ ID NO: 35) | CAESTGGSYIPTF (SEQ ID NO: 151) |
| TCR18, β | SNHLY (SEQ ID NO: 187) | FYNNEI (SEQ ID NO: 175) | CASASDSDDEKLFF (SEQ ID NO: 160) |
| TCR19, α | YGGTVN (SEQ ID NO: 181) | YFSGDPLV (SEQ ID NO: 169) | CAVNAPGGYNKLIF (SEQ ID NO: 152) |
| TCR19, β | LNHDA (SEQ ID NO: 82) | SQIVND (SEQ ID NO: 56) | CASSISQGGYGYTF (SEQ ID NO: 161) |
| TCR20, α | DSVNN (SEQ ID NO: 68) | IPSGT (SEQ ID NO: 45) | CAVERPTGGYNKLIF (SEQ ID NO: 153) |
| TCR20, β | SGHRS (SEQ ID NO: 188) | YFSETQ (SEQ ID NO: 176) | CASSPGTDYEQYF (SEQ ID NO: 162) |
| TCR21, α | DSAIYN (SEQ ID NO: 182) | IQSSQRE (SEQ ID NO: 170) | CAVEDYGQNFVF (SEQ ID NO: 154) |
| TCR21, β | DFQATT (SEQ ID NO: 72) | SNEGSKA (SEQ ID NO: 47) | CSARDLSGRSLDTQYF (SEQ ID NO: 163) |
| TCR22, α | TRDTTYY (SEQ ID NO: 183) | RNSFDEQN (SEQ ID NO: 171) | CALSDSSGGSYIPTF (SEQ ID NO: 155) |
| TCR22, β | SEHNR (SEQ ID NO: 189) | FQNEAQ (SEQ ID NO: 49) | CASSLGRQTNTEAFF (SEQ ID NO: 164) |
| TCR23, α | DSASNY (SEQ ID NO: 184) | IRSNVGE (SEQ ID NO: 172) | CAACYSGYALNF (SEQ ID NO: 156) |
| TCR23, β | MNHEY (SEQ ID NO: 78) | SVGAGI (SEQ ID NO: 177) | CASSYRPKLDTEAFF (SEQ ID NO: 165) |
| TCR24, α | DSAIYN (SEQ ID NO: 182) | IQSSQRE (SEQ ID NO: 170) | CAVVTNDYKLSF (SEQ ID NO: 157) |
| TCR24, β | LGHDT (SEQ ID NO: 190) | YNNKEL (SEQ ID NO: 178) | CASSQDLGQGSDTQYF (SEQ ID NO: 166) |
| TCR25, α | TSDQSYG (SEQ ID NO: 185) | QGSYDEQN (SEQ ID NO: 173) | CAMRSFAQAGTALIF (SEQ ID NO: 158) |
| TCR25, β | LGHNA (SEQ ID NO: 79) | YNFKEQ (SEQ ID NO: 53) | CASSQRGKGQGDEETQYF (SEQ ID NO: 167) |
| TCR26, α | TTLSN (SEQ ID NO: 186) | LVKSGEV (SEQ ID NO: 174) | CAGWISPQGAQKLVF (SEQ ID NO: 159) |
| TCR26, β | SSHAT (SEQ ID NO: 191) | FNYEAQ (SEQ ID NO: 180) | CASSLSTNTEAFF (SEQ ID NO: 168) |

or wherein the TCRs of the library have CDR sequences corresponding to the CDRs set forth in the above table, wherein one or two amino acids of the CDRs of the TCR as set forth in the table may be replaced with another amino acid in the TCRs of the library.

6. The TCR library according to claim 5, wherein the TCR library includes four or more TCRs that have a CDR1a sequence comprising amino acid motif DSSSTY (SEQ ID NO:58), and/or five or more TCRs that have a CDR1a sequence comprising amino acid motif SQS (SEQ ID NO:87), and/or three or more TCRs that have a CDR1a sequence comprising amino acid motif TSESDYY (SEQ ID NO:62), and/or three or more TCRs that have a CDR1a sequence comprising amino acid motif SVFSS (SEQ ID NO: 67), and/or three or more TCRs that have a CDR1a sequence comprising amino acid motif SxNN (SEQ ID NO:84), wherein the x in SxNN (SEQ ID NO:84) is isoleucine (I) or valine (V);

and/or wherein the TCR library includes four or more TCRs that have a CDR1b sequence comprising amino acid motif DFQATT (SEQ ID NO:72), and/or eight or more TCRs that have a CDR1b sequence comprising amino acid motif SG (SEQ ID NO:95), and/or four or more TCRs that have a CDR1b sequence comprising amino acid motif GHN (SEQ ID NO:102), and/or seven or more TCRs that have a CDR1b sequence comprising amino acid motif MxHEz (SEQ ID NO:97), wherein the x in MxHEz (SEQ ID NO:97) is asparagine (N) or aspartic acid (D) and wherein the z in MxHEz (SEQ ID NO:97) is asparagine (N) or tyrosine (Y);

and/or wherein the TCR library includes nine or more TCRs that have a CDR2a sequence comprising amino acid: SN (SEQ ID NO:104), and/or three or more TCRs that have a CDR2a sequence comprising amino acid motif GGE (SEQ ID NO:107), and/or four or more TCRs that have a CDR2a sequence comprising amino acid motif YK (SEQ ID NO:109), and/or three or more TCRs that have a CDR2a sequence comprising amino acid motif GEE (SEQ ID NO: 111);

and/or wherein the TCR library includes four or more TCRs that have a CDR2b sequence comprising amino acid motif SNEGSKA (SEQ ID NO:47), and/or three or more TCRs that have a CDR2b sequence comprising amino acid motif FNNNVP (SEQ ID NO:48), and/or four or more TCRs that have a CDR2b sequence comprising amino acid motif FQN (SEQ ID NO: 179), and/or four or more TCRs that have a CDR2b sequence comprising amino acid motif SYDVKM (SEQ ID NO:50), and/or four or more TCRs that have a CDR2b sequence comprising amino acid motif SMNVEV (SEQ ID NO:52);

and/or wherein the TCRs are chimeric TCRs.

* * * * *

SEQUENCE LISTING

```
<160> NUMBER OF SEQ ID NOS: 193

<210> SEQ ID NO 1
<211> LENGTH: 12
<212> TYPE: PRT
<213> ORGANISM: Artificial Sequence
<220> FEATURE:
<223> OTHER INFORMATION: TCR CDR3a

<400> SEQUENCE: 1

Ala Glu Thr Leu Asp Asn Tyr Gly Gln Asn Phe Val
1               5                   10


<210> SEQ ID NO 2
<211> LENGTH: 13
<212> TYPE: PRT
<213> ORGANISM: Artificial Sequence
<220> FEATURE:
<223> OTHER INFORMATION: TCR CDR3a

<400> SEQUENCE: 2

Ala Thr Trp Leu Ser Gly Ser Ala Arg Gln Leu Thr Phe
1               5                   10


<210> SEQ ID NO 3
<211> LENGTH: 11
<212> TYPE: PRT
<213> ORGANISM: Artificial Sequence
<220> FEATURE:
<223> OTHER INFORMATION: TCR CDR3a

<400> SEQUENCE: 3

Ala Val Asn Leu Tyr Ala Gly Asn Met Leu Thr
1               5                   10


<210> SEQ ID NO 4
<211> LENGTH: 12
<212> TYPE: PRT
<213> ORGANISM: Artificial Sequence
<220> FEATURE:
```

<223> OTHER INFORMATION: TCR CDR3a

<400> SEQUENCE: 4

Cys Gly Ala Asp Arg Gly Gly Gly Lys Leu Ile Phe
1 5 10

<210> SEQ ID NO 5
<211> LENGTH: 13
<212> TYPE: PRT
<213> ORGANISM: Artificial Sequence
<220> FEATURE:
<223> OTHER INFORMATION: TCR CDR3a

<400> SEQUENCE: 5

Cys Ala Tyr Arg Ser Gly Leu Asn Asn Asp Met Arg Phe
1 5 10

<210> SEQ ID NO 6
<211> LENGTH: 11
<212> TYPE: PRT
<213> ORGANISM: Artificial Sequence
<220> FEATURE:
<223> OTHER INFORMATION: TCR CDR3a

<400> SEQUENCE: 6

Ala Val Ser Asp Asn Gln Gly Gly Lys Leu Ile
1 5 10

<210> SEQ ID NO 7
<211> LENGTH: 12
<212> TYPE: PRT
<213> ORGANISM: Artificial Sequence
<220> FEATURE:
<223> OTHER INFORMATION: TCR CDR3a

<400> SEQUENCE: 7

Cys Ala Val Arg Tyr Asn Asn Ala Arg Leu Met Phe
1 5 10

<210> SEQ ID NO 8
<211> LENGTH: 14
<212> TYPE: PRT
<213> ORGANISM: Artificial Sequence
<220> FEATURE:
<223> OTHER INFORMATION: TCR CDR3a

<400> SEQUENCE: 8

Cys Val Val Asn Gly Val Asp Ser Ser Tyr Lys Leu Ile Phe
1 5 10

<210> SEQ ID NO 9
<211> LENGTH: 15
<212> TYPE: PRT
<213> ORGANISM: Artificial Sequence
<220> FEATURE:
<223> OTHER INFORMATION: TCR CDR3a

<400> SEQUENCE: 9

Cys Leu Val Gly Asp Glu Asp Thr Gly Arg Arg Ala Leu Thr Phe
1 5 10 15

<210> SEQ ID NO 10
<211> LENGTH: 14
<212> TYPE: PRT
<213> ORGANISM: Artificial Sequence
<220> FEATURE:
<223> OTHER INFORMATION: TCR CDR3a

<400> SEQUENCE: 10

Cys Ala Val Arg Asp Gln Thr Gly Ala Asn Asn Leu Phe Phe
1 5 10

<210> SEQ ID NO 11
<211> LENGTH: 13
<212> TYPE: PRT
<213> ORGANISM: Artificial Sequence
<220> FEATURE:
<223> OTHER INFORMATION: TCR CDR3a

<400> SEQUENCE: 11

Cys Ala Val Asn Met Val Ala Gly Asn Met Leu Thr Phe
1 5 10

<210> SEQ ID NO 12
<211> LENGTH: 11
<212> TYPE: PRT
<213> ORGANISM: Artificial Sequence
<220> FEATURE:
<223> OTHER INFORMATION: TCR CDR3a

<400> SEQUENCE: 12

Cys Ala Val Asp Gly Asn Asn Arg Leu Ala Phe
1 5 10

<210> SEQ ID NO 13
<211> LENGTH: 15
<212> TYPE: PRT
<213> ORGANISM: Artificial Sequence
<220> FEATURE:
<223> OTHER INFORMATION: TCR CDR3a

<400> SEQUENCE: 13

Cys Ala Gly Ala Gly Tyr Gly Gly Ser Gln Gly Asn Leu Ile Phe
1 5 10 15

<210> SEQ ID NO 14
<211> LENGTH: 13
<212> TYPE: PRT
<213> ORGANISM: Artificial Sequence
<220> FEATURE:
<223> OTHER INFORMATION: TCR CDR3a

<400> SEQUENCE: 14

Cys Ala Tyr Ile Gly Asn Ala Gly Asn Met Leu Thr Phe
1 5 10

<210> SEQ ID NO 15
<211> LENGTH: 13
<212> TYPE: PRT
<213> ORGANISM: Artificial Sequence
<220> FEATURE:
<223> OTHER INFORMATION: TCR CDR3a

<400> SEQUENCE: 15

Cys Ala Val Tyr His Thr Gly Phe Gln Lys Leu Val Phe
1 5 10

<210> SEQ ID NO 16
<211> LENGTH: 13
<212> TYPE: PRT
<213> ORGANISM: Artificial Sequence
<220> FEATURE:
<223> OTHER INFORMATION: TCR CDR3a

<400> SEQUENCE: 16

Cys Ala Glu Ser Met Gly Asp Phe Asn Lys Phe Tyr Phe
1               5                   10

<210> SEQ ID NO 17
<211> LENGTH: 14
<212> TYPE: PRT
<213> ORGANISM: Artificial Sequence
<220> FEATURE:
<223> OTHER INFORMATION: TCR CDR3a

<400> SEQUENCE: 17

Cys Ala Val Ser Thr Asn Phe Gly Asn Glu Lys Leu Thr Phe
1               5                   10

<210> SEQ ID NO 18
<211> LENGTH: 16
<212> TYPE: PRT
<213> ORGANISM: Artificial Sequence
<220> FEATURE:
<223> OTHER INFORMATION: TCR CDR3b

<400> SEQUENCE: 18

Ser Ala Val Asp Arg Asp Glu Pro Phe His Ser Asn Gln Pro Gln His
1               5                   10                  15

<210> SEQ ID NO 19
<211> LENGTH: 13
<212> TYPE: PRT
<213> ORGANISM: Artificial Sequence
<220> FEATURE:
<223> OTHER INFORMATION: TCR CDR3b

<400> SEQUENCE: 19

Ala Ser Ser Asn Arg Ala Ser Ser Tyr Asn Glu Gln Phe
1               5                   10

<210> SEQ ID NO 20
<211> LENGTH: 12
<212> TYPE: PRT
<213> ORGANISM: Artificial Sequence
<220> FEATURE:
<223> OTHER INFORMATION: TCR CDR3b

<400> SEQUENCE: 20

Ala Ser Ser Ser Asp Phe Gly Asn Gln Pro Gln His
1               5                   10

<210> SEQ ID NO 21
<211> LENGTH: 14
<212> TYPE: PRT
<213> ORGANISM: Artificial Sequence
<220> FEATURE:
<223> OTHER INFORMATION: TCR CDR3b

<400> SEQUENCE: 21

Cys Ala Ser Ser Leu Phe Lys Gly Ala Asp Thr Gln Tyr Phe
1               5                   10

<210> SEQ ID NO 22
<211> LENGTH: 17
<212> TYPE: PRT
<213> ORGANISM: Artificial Sequence
<220> FEATURE:
<223> OTHER INFORMATION: TCR CDR3b

<400> SEQUENCE: 22

Cys Ala Ser Ser Leu Glu Leu Ala Gly Pro Trp Gly Asn Glu Gln Phe
1               5                   10                  15

Phe

<210> SEQ ID NO 23
<211> LENGTH: 11
<212> TYPE: PRT
<213> ORGANISM: Artificial Sequence
<220> FEATURE:
<223> OTHER INFORMATION: TCR CDR3b

<400> SEQUENCE: 23

Ala Ser Ser Leu Ser Ala Ala Tyr Glu Gln Tyr
1               5                   10

<210> SEQ ID NO 24
<211> LENGTH: 13
<212> TYPE: PRT
<213> ORGANISM: Artificial Sequence
<220> FEATURE:
<223> OTHER INFORMATION: TCR CDR3b

<400> SEQUENCE: 24

Cys Ser Ala Pro Ala Gly Met Gly Tyr Glu Gln Tyr Phe
1               5                   10

<210> SEQ ID NO 25
<211> LENGTH: 16
<212> TYPE: PRT
<213> ORGANISM: Artificial Sequence
<220> FEATURE:
<223> OTHER INFORMATION: TCR CDR3b

<400> SEQUENCE: 25

Cys Ala Ser Glu Met Ala Gly Gly Gly Asp Asn Tyr Gly Tyr Thr Phe
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: TCR CDR3b

<400> SEQUENCE: 26

Cys Ala Ser Ser Phe Ser Gly Lys Ala Ser Tyr Tyr Glu Gln Tyr Phe
1               5                   10                  15

<210> SEQ ID NO 27
<211> LENGTH: 17
<212> TYPE: PRT
<213> ORGANISM: Artificial Sequence
<220> FEATURE:
<223> OTHER INFORMATION: TCR CDR3b

<400> SEQUENCE: 27

Cys Ala Ser Ser Pro Glu Pro Thr Ser Gly Ser Phe Asn Glu Gln Phe
1               5                   10                  15

Phe

<210> SEQ ID NO 28
<211> LENGTH: 15
<212> TYPE: PRT
<213> ORGANISM: Artificial Sequence
<220> FEATURE:

<223> OTHER INFORMATION: TCR CDR3b

<400> SEQUENCE: 28

Cys Ala Ser Ser Pro Asp Ser Ser Gly Ala Asn Val Leu Thr Phe
1 5 10 15

<210> SEQ ID NO 29
<211> LENGTH: 14
<212> TYPE: PRT
<213> ORGANISM: Artificial Sequence
<220> FEATURE:
<223> OTHER INFORMATION: TCR CDR3b

<400> SEQUENCE: 29

Cys Ser Val Asp Met Asp Trp Gly Ile Gly Gly Tyr Thr Phe
1 5 10

<210> SEQ ID NO 30
<211> LENGTH: 13
<212> TYPE: PRT
<213> ORGANISM: Artificial Sequence
<220> FEATURE:
<223> OTHER INFORMATION: TCR CDR3b

<400> SEQUENCE: 30

Cys Ala Ser Ser Ile Ala Gly Gly Ala Glu Gln Tyr Phe
1 5 10

<210> SEQ ID NO 31
<211> LENGTH: 15
<212> TYPE: PRT
<213> ORGANISM: Artificial Sequence
<220> FEATURE:
<223> OTHER INFORMATION: TCR CDR3b

<400> SEQUENCE: 31

Cys Ala Ser Ser Leu Ser Tyr Arg Gly Leu Gly Glu Gln Phe Phe
1 5 10 15

<210> SEQ ID NO 32
<211> LENGTH: 15
<212> TYPE: PRT
<213> ORGANISM: Artificial Sequence
<220> FEATURE:
<223> OTHER INFORMATION: TCR CDR3b

<400> SEQUENCE: 32

Cys Ala Ser Ser Ser Arg Gln Gly Gly Thr Tyr Glu Gln Tyr Phe
1 5 10 15

<210> SEQ ID NO 33
<211> LENGTH: 14
<212> TYPE: PRT
<213> ORGANISM: Artificial Sequence
<220> FEATURE:
<223> OTHER INFORMATION: TCR CDR3b

<400> SEQUENCE: 33

Cys Ala Ser Ser Pro Gly Glu Gly Asn Gln Pro Gln His Phe
1 5 10

<210> SEQ ID NO 34
<211> LENGTH: 16
<212> TYPE: PRT
<213> ORGANISM: Artificial Sequence
<220> FEATURE:
<223> OTHER INFORMATION: TCR CDR3b

<400> SEQUENCE: 34

Cys Ala Ser Ser Ala Ser Leu Ala Asp Asn Thr Gly Glu Leu Phe Phe
1 5 10 15

<210> SEQ ID NO 35
<211> LENGTH: 7
<212> TYPE: PRT
<213> ORGANISM: Artificial Sequence
<220> FEATURE:
<223> OTHER INFORMATION: TCR CDR2a

<400> SEQUENCE: 35

Ile Phe Ser Asn Met Asp Met
1 5

<210> SEQ ID NO 36
<211> LENGTH: 7
<212> TYPE: PRT
<213> ORGANISM: Artificial Sequence
<220> FEATURE:
<223> OTHER INFORMATION: TCR CDR2a

<400> SEQUENCE: 36

Ile Arg Ser Asn Glu Arg Glu
1 5

<210> SEQ ID NO 37
<211> LENGTH: 6
<212> TYPE: PRT
<213> ORGANISM: Artificial Sequence
<220> FEATURE:
<223> OTHER INFORMATION: TCR CDR2a

<400> SEQUENCE: 37

Ile Tyr Ser Asn Gly Asp
1 5

<210> SEQ ID NO 38
<211> LENGTH: 7
<212> TYPE: PRT
<213> ORGANISM: Artificial Sequence
<220> FEATURE:
<223> OTHER INFORMATION: TCR CDR2a

<400> SEQUENCE: 38

Leu Gln Lys Gly Gly Glu Glu
1 5

<210> SEQ ID NO 39
<211> LENGTH: 8
<212> TYPE: PRT
<213> ORGANISM: Artificial Sequence
<220> FEATURE:
<223> OTHER INFORMATION: TCR CDR2a

<400> SEQUENCE: 39

Gln Glu Ala Tyr Lys Gln Gln Asn
1 5

<210> SEQ ID NO 40
<211> LENGTH: 8
<212> TYPE: PRT
<213> ORGANISM: Artificial Sequence
<220> FEATURE:
<223> OTHER INFORMATION: TCR CDR2a

<400> SEQUENCE: 40

Tyr Leu Ser Gly Ser Thr Leu Val
1 5

<210> SEQ ID NO 41
<211> LENGTH: 6
<212> TYPE: PRT
<213> ORGANISM: Artificial Sequence
<220> FEATURE:
<223> OTHER INFORMATION: TCR CDR2a

<400> SEQUENCE: 41

Asn Val Leu Asp Gly Leu
1 5

<210> SEQ ID NO 42
<211> LENGTH: 6
<212> TYPE: PRT
<213> ORGANISM: Artificial Sequence
<220> FEATURE:
<223> OTHER INFORMATION: TCR CDR2a

<400> SEQUENCE: 42

Val Tyr Ser Ser Gly Asn
1 5

<210> SEQ ID NO 43
<211> LENGTH: 5
<212> TYPE: PRT
<213> ORGANISM: Artificial Sequence
<220> FEATURE:
<223> OTHER INFORMATION: TCR CDR2a

<400> SEQUENCE: 43

Gly Tyr Lys Thr Lys
1 5

<210> SEQ ID NO 44
<211> LENGTH: 7
<212> TYPE: PRT
<213> ORGANISM: Artificial Sequence
<220> FEATURE:
<223> OTHER INFORMATION: TCR CDR2a

<400> SEQUENCE: 44

Val Val Thr Gly Gly Glu Val
1 5

<210> SEQ ID NO 45
<211> LENGTH: 5
<212> TYPE: PRT
<213> ORGANISM: Artificial Sequence
<220> FEATURE:
<223> OTHER INFORMATION: TCR CDR2a

<400> SEQUENCE: 45

Ile Pro Ser Gly Thr
1 5

<210> SEQ ID NO 46
<211> LENGTH: 7
<212> TYPE: PRT
<213> ORGANISM: Artificial Sequence
<220> FEATURE:
<223> OTHER INFORMATION: TCR CDR2a

<400> SEQUENCE: 46

Leu Tyr Ser Ala Gly Glu Glu
1 5

<210> SEQ ID NO 47
<211> LENGTH: 7
<212> TYPE: PRT
<213> ORGANISM: Artificial Sequence
<220> FEATURE:
<223> OTHER INFORMATION: TCR CDR2b

<400> SEQUENCE: 47

Ser Asn Glu Gly Ser Lys Ala
1 5

<210> SEQ ID NO 48
<211> LENGTH: 6
<212> TYPE: PRT
<213> ORGANISM: Artificial Sequence
<220> FEATURE:
<223> OTHER INFORMATION: TCR CDR2b

<400> SEQUENCE: 48

Phe Asn Asn Asn Val Pro
1 5

<210> SEQ ID NO 49
<211> LENGTH: 6
<212> TYPE: PRT
<213> ORGANISM: Artificial Sequence
<220> FEATURE:
<223> OTHER INFORMATION: TCR CDR2b

<400> SEQUENCE: 49

Phe Gln Asn Glu Ala Gln
1 5

<210> SEQ ID NO 50
<211> LENGTH: 6
<212> TYPE: PRT
<213> ORGANISM: Artificial Sequence
<220> FEATURE:
<223> OTHER INFORMATION: TCR CDR2b

<400> SEQUENCE: 50

Ser Tyr Asp Val Lys Met
1 5

<210> SEQ ID NO 51
<211> LENGTH: 6
<212> TYPE: PRT
<213> ORGANISM: Artificial Sequence
<220> FEATURE:
<223> OTHER INFORMATION: TCR CDR2b

<400> SEQUENCE: 51

Phe Gln Asn Asn Gly Val
1 5

<210> SEQ ID NO 52
<211> LENGTH: 6
<212> TYPE: PRT
<213> ORGANISM: Artificial Sequence
<220> FEATURE:
<223> OTHER INFORMATION: TCR CDR2b

<400> SEQUENCE: 52

Ser Met Asn Val Glu Val
1 5

<210> SEQ ID NO 53
<211> LENGTH: 6
<212> TYPE: PRT
<213> ORGANISM: Artificial Sequence
<220> FEATURE:
<223> OTHER INFORMATION: TCR CDR2b

<400> SEQUENCE: 53

Tyr Asn Phe Lys Glu Gln
1 5

<210> SEQ ID NO 54
<211> LENGTH: 6
<212> TYPE: PRT
<213> ORGANISM: Artificial Sequence
<220> FEATURE:
<223> OTHER INFORMATION: TCR CDR2b

<400> SEQUENCE: 54

Phe Gln Gly Thr Gly Ala
1 5

<210> SEQ ID NO 55
<211> LENGTH: 7
<212> TYPE: PRT
<213> ORGANISM: Artificial Sequence
<220> FEATURE:
<223> OTHER INFORMATION: TCR CDR2b

<400> SEQUENCE: 55

Ala Asn Gln Gly Ser Glu Ala
1 5

<210> SEQ ID NO 56
<211> LENGTH: 6
<212> TYPE: PRT
<213> ORGANISM: Artificial Sequence
<220> FEATURE:
<223> OTHER INFORMATION: TCR CDR2b

<400> SEQUENCE: 56

Ser Gln Ile Val Asn Asp
1 5

<210> SEQ ID NO 57
<211> LENGTH: 6
<212> TYPE: PRT
<213> ORGANISM: Artificial Sequence
<220> FEATURE:
<223> OTHER INFORMATION: TCR CDR2b

<400> SEQUENCE: 57

Tyr Tyr Asn Gly Glu Glu
1 5

<210> SEQ ID NO 58
<211> LENGTH: 6
<212> TYPE: PRT
<213> ORGANISM: Artificial Sequence
<220> FEATURE:
<223> OTHER INFORMATION: TCR CDR1a

<400> SEQUENCE: 58

Asp Ser Ser Ser Thr Tyr 1 5

<210> SEQ ID NO 59
<211> LENGTH: 5
<212> TYPE: PRT
<213> ORGANISM: Artificial Sequence
<220> FEATURE:
<223> OTHER INFORMATION: TCR CDR1a

<400> SEQUENCE: 59

Thr Ser Ile Asn Asn
1 5

<210> SEQ ID NO 60
<211> LENGTH: 6
<212> TYPE: PRT
<213> ORGANISM: Artificial Sequence
<220> FEATURE:
<223> OTHER INFORMATION: TCR CDR1a

<400> SEQUENCE: 60

Asp Arg Gly Ser Gln Ser
1 5

<210> SEQ ID NO 61
<211> LENGTH: 5
<212> TYPE: PRT
<213> ORGANISM: Artificial Sequence
<220> FEATURE:
<223> OTHER INFORMATION: TCR CDR1a

<400> SEQUENCE: 61

Lys Thr Leu Tyr Gly
1 5

<210> SEQ ID NO 62
<211> LENGTH: 7
<212> TYPE: PRT
<213> ORGANISM: Artificial Sequence
<220> FEATURE:
<223> OTHER INFORMATION: TCR CDR1a

<400> SEQUENCE: 62

Thr Ser Glu Ser Asp Tyr Tyr
1 5

<210> SEQ ID NO 63
<211> LENGTH: 6
<212> TYPE: PRT
<213> ORGANISM: Artificial Sequence
<220> FEATURE:
<223> OTHER INFORMATION: TCR CDR1a

<400> SEQUENCE: 63

Ser Ser Val Ser Val Tyr
1 5

<210> SEQ ID NO 64
<211> LENGTH: 6
<212> TYPE: PRT
<213> ORGANISM: Artificial Sequence
<220> FEATURE:
<223> OTHER INFORMATION: TCR CDR1a

<400> SEQUENCE: 64

Thr Ser Gly Phe Asn Gly
1 5

-continued

<210> SEQ ID NO 65
<211> LENGTH: 6
<212> TYPE: PRT
<213> ORGANISM: Artificial Sequence
<220> FEATURE:
<223> OTHER INFORMATION: TCR CDR1a

<400> SEQUENCE: 65

Asn Ser Ala Ser Gln Ser
1               5

<210> SEQ ID NO 66
<211> LENGTH: 7
<212> TYPE: PRT
<213> ORGANISM: Artificial Sequence
<220> FEATURE:
<223> OTHER INFORMATION: TCR CDR1a

<400> SEQUENCE: 66

Asn Ile Ala Thr Asn Asp Tyr
1               5

<210> SEQ ID NO 67
<211> LENGTH: 5
<212> TYPE: PRT
<213> ORGANISM: Artificial Sequence
<220> FEATURE:
<223> OTHER INFORMATION: TCR CDR1a

<400> SEQUENCE: 67

Ser Val Phe Ser Ser
1               5

<210> SEQ ID NO 68
<211> LENGTH: 5
<212> TYPE: PRT
<213> ORGANISM: Artificial Sequence
<220> FEATURE:
<223> OTHER INFORMATION: TCR CDR1a

<400> SEQUENCE: 68

Asp Ser Val Asn Asn
1               5

<210> SEQ ID NO 69
<211> LENGTH: 6
<212> TYPE: PRT
<213> ORGANISM: Artificial Sequence
<220> FEATURE:
<223> OTHER INFORMATION: TCR CDR1a

<400> SEQUENCE: 69

Val Ser Gly Leu Arg Gly
1               5

<210> SEQ ID NO 70
<211> LENGTH: 6
<212> TYPE: PRT
<213> ORGANISM: Artificial Sequence
<220> FEATURE:
<223> OTHER INFORMATION: TCR CDR1a

<400> SEQUENCE: 70

Asp Arg Val Ser Gln Ser
1               5

-continued

<210> SEQ ID NO 71
<211> LENGTH: 6
<212> TYPE: PRT
<213> ORGANISM: Artificial Sequence
<220> FEATURE:
<223> OTHER INFORMATION: TCR CDR1a

<400> SEQUENCE: 71

Asp Ile Ser Ser Thr Tyr
1               5

<210> SEQ ID NO 72
<211> LENGTH: 6
<212> TYPE: PRT
<213> ORGANISM: Artificial Sequence
<220> FEATURE:
<223> OTHER INFORMATION: TCR CDR1b

<400> SEQUENCE: 72

Asp Phe Gln Ala Thr Thr
1               5

<210> SEQ ID NO 73
<211> LENGTH: 5
<212> TYPE: PRT
<213> ORGANISM: Artificial Sequence
<220> FEATURE:
<223> OTHER INFORMATION: TCR CDR1b

<400> SEQUENCE: 73

Ser Gly His Asp Tyr
1               5

<210> SEQ ID NO 74
<211> LENGTH: 5
<212> TYPE: PRT
<213> ORGANISM: Artificial Sequence
<220> FEATURE:
<223> OTHER INFORMATION: TCR CDR1b

<400> SEQUENCE: 74

Ser Gly His Val Ser
1               5

<210> SEQ ID NO 75
<211> LENGTH: 5
<212> TYPE: PRT
<213> ORGANISM: Artificial Sequence
<220> FEATURE:
<223> OTHER INFORMATION: TCR CDR1b

<400> SEQUENCE: 75

Met Asp His Glu Asn
1               5

<210> SEQ ID NO 76
<211> LENGTH: 5
<212> TYPE: PRT
<213> ORGANISM: Artificial Sequence
<220> FEATURE:
<223> OTHER INFORMATION: TCR CDR1b

<400> SEQUENCE: 76

Ser Gly His Ala Thr
1               5

<210> SEQ ID NO 77
<211> LENGTH: 5
<212> TYPE: PRT
<213> ORGANISM: Artificial Sequence
<220> FEATURE:
<223> OTHER INFORMATION: TCR CDR1b

<400> SEQUENCE: 77

Ser Gly His Asn Ser
1 5

<210> SEQ ID NO 78
<211> LENGTH: 5
<212> TYPE: PRT
<213> ORGANISM: Artificial Sequence
<220> FEATURE:
<223> OTHER INFORMATION: TCR CDR1b

<400> SEQUENCE: 78

Met Asn His Glu Tyr
1 5

<210> SEQ ID NO 79
<211> LENGTH: 5
<212> TYPE: PRT
<213> ORGANISM: Artificial Sequence
<220> FEATURE:
<223> OTHER INFORMATION: TCR CDR1b

<400> SEQUENCE: 79

Leu Gly His Asn Ala
1 5

<210> SEQ ID NO 80
<211> LENGTH: 5
<212> TYPE: PRT
<213> ORGANISM: Artificial Sequence
<220> FEATURE:
<223> OTHER INFORMATION: TCR CDR1b

<400> SEQUENCE: 80

Ser Gly His Thr Ala
1 5

<210> SEQ ID NO 81
<211> LENGTH: 5
<212> TYPE: PRT
<213> ORGANISM: Artificial Sequence
<220> FEATURE:
<223> OTHER INFORMATION: TCR CDR1b

<400> SEQUENCE: 81

Ser Gln Val Thr Met
1 5

<210> SEQ ID NO 82
<211> LENGTH: 5
<212> TYPE: PRT
<213> ORGANISM: Artificial Sequence
<220> FEATURE:
<223> OTHER INFORMATION: TCR CDR1b

<400> SEQUENCE: 82

Leu Asn His Asp Ala
1 5

<210> SEQ ID NO 83

<211> LENGTH: 5
<212> TYPE: PRT
<213> ORGANISM: Artificial Sequence
<220> FEATURE:
<223> OTHER INFORMATION: TCR CDR1b

<400> SEQUENCE: 83

Ser Gly Asp Leu Ser
1 5

<210> SEQ ID NO 84
<211> LENGTH: 4
<212> TYPE: PRT
<213> ORGANISM: Artificial Sequence
<220> FEATURE:
<223> OTHER INFORMATION: TCR motif
<220> FEATURE:
<221> NAME/KEY: misc_feature
<222> LOCATION: (2)..(2)
<223> OTHER INFORMATION: Xaa can be any naturally occurring amino acid

<400> SEQUENCE: 84

Ser Xaa Asn Asn
1

<210> SEQ ID NO 85
<211> LENGTH: 4
<212> TYPE: PRT
<213> ORGANISM: Artificial Sequence
<220> FEATURE:
<223> OTHER INFORMATION: TCR motif

<400> SEQUENCE: 85

Ser Ile Asn Asn
1

<210> SEQ ID NO 86
<211> LENGTH: 4
<212> TYPE: PRT
<213> ORGANISM: Artificial Sequence
<220> FEATURE:
<223> OTHER INFORMATION: TCR motif

<400> SEQUENCE: 86

Ser Val Asn Asn
1

<210> SEQ ID NO 87
<211> LENGTH: 3
<212> TYPE: PRT
<213> ORGANISM: Artificial Sequence
<220> FEATURE:
<223> OTHER INFORMATION: TCR motif

<400> SEQUENCE: 87

Ser Gln Ser
1

<210> SEQ ID NO 88

<400> SEQUENCE: 88

000

<210> SEQ ID NO 89
<211> LENGTH: 6
<212> TYPE: PRT
<213> ORGANISM: Artificial Sequence
<220> FEATURE:
<223> OTHER INFORMATION: TCR motif
<220> FEATURE:
<221> NAME/KEY: misc_feature
<222> LOCATION: (3)..(3)
<223> OTHER INFORMATION: Xaa can be any naturally occurring amino acid

<400> SEQUENCE: 89

Asp Arg Xaa Ser Gln Ser
1               5

<210> SEQ ID NO 90
<211> LENGTH: 6
<212> TYPE: PRT
<213> ORGANISM: Artificial Sequence
<220> FEATURE:
<223> OTHER INFORMATION: TCR motif

<400> SEQUENCE: 90

Asp Arg Gly Ser Gln Ser
1               5

<210> SEQ ID NO 91
<211> LENGTH: 6
<212> TYPE: PRT
<213> ORGANISM: Artificial Sequence
<220> FEATURE:
<223> OTHER INFORMATION: TCR motif

<400> SEQUENCE: 91

Asp Arg Val Ser Gln Ser
1               5

<210> SEQ ID NO 92
<211> LENGTH: 2
<212> TYPE: PRT
<213> ORGANISM: Artificial Sequence
<220> FEATURE:
<223> OTHER INFORMATION: TCR motif

<400> SEQUENCE: 92

Ser Val
1

<210> SEQ ID NO 93
<211> LENGTH: 5
<212> TYPE: PRT
<213> ORGANISM: Artificial Sequence
<220> FEATURE:
<223> OTHER INFORMATION: TCR motif

<400> SEQUENCE: 93

Ser Val Phe Ser Ser
1               5

<210> SEQ ID NO 94
<211> LENGTH: 6
<212> TYPE: PRT
<213> ORGANISM: Artificial Sequence
<220> FEATURE:
<223> OTHER INFORMATION: TCR motif

<400> SEQUENCE: 94

Asp Phe Gln Ala Thr Thr
1               5

<210> SEQ ID NO 95

<211> LENGTH: 2
<212> TYPE: PRT
<213> ORGANISM: Artificial Sequence
<220> FEATURE:
<223> OTHER INFORMATION: TCR motif

<400> SEQUENCE: 95

Ser Gly
1

<210> SEQ ID NO 96
<211> LENGTH: 3
<212> TYPE: PRT
<213> ORGANISM: Artificial Sequence
<220> FEATURE:
<223> OTHER INFORMATION: TCR motif

<400> SEQUENCE: 96

Ser Gly His
1

<210> SEQ ID NO 97
<211> LENGTH: 5
<212> TYPE: PRT
<213> ORGANISM: Artificial Sequence
<220> FEATURE:
<223> OTHER INFORMATION: TCR motif
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 97

Met Xaa His Glu Xaa
1               5

<210> SEQ ID NO 98
<211> LENGTH: 5
<212> TYPE: PRT
<213> ORGANISM: Artificial Sequence
<220> FEATURE:
<223> OTHER INFORMATION: TCR motif
<220> FEATURE:
<221> NAME/KEY: misc_feature
<222> LOCATION: (5)..(5)
<223> OTHER INFORMATION: Xaa can be any naturally occurring amino acid

<400> SEQUENCE: 98

Met Asn His Glu Xaa
1               5

<210> SEQ ID NO 99
<211> LENGTH: 5
<212> TYPE: PRT
<213> ORGANISM: Artificial Sequence
<220> FEATURE:
<223> OTHER INFORMATION: TCR motif
<220> FEATURE:
<221> NAME/KEY: misc_feature
<222> LOCATION: (5)..(5)
<223> OTHER INFORMATION: Xaa can be any naturally occurring amino acid

<400> SEQUENCE: 99

Met Asp His Glu Xaa
1               5

<210> SEQ ID NO 100
<211> LENGTH: 5
<212> TYPE: PRT
<213> ORGANISM: Artificial Sequence
<220> FEATURE:
<223> OTHER INFORMATION: TCR motif
<220> FEATURE:
<221> NAME/KEY: misc_feature
<222> LOCATION: (2)..(2)
<223> OTHER INFORMATION: Xaa can be any naturally occurring amino acid

<400> SEQUENCE: 100

Met Xaa His Glu Asn
1               5

<210> SEQ ID NO 101
<211> LENGTH: 5
<212> TYPE: PRT
<213> ORGANISM: Artificial Sequence
<220> FEATURE:
<223> OTHER INFORMATION: TCR motif
<220> FEATURE:
<221> NAME/KEY: misc_feature
<222> LOCATION: (2)..(2)
<223> OTHER INFORMATION: Xaa can be any naturally occurring amino acid

<400> SEQUENCE: 101

Met Xaa His Glu Tyr
1               5

<210> SEQ ID NO 102
<211> LENGTH: 3
<212> TYPE: PRT
<213> ORGANISM: Artificial Sequence
<220> FEATURE:
<223> OTHER INFORMATION: TCR motif

<400> SEQUENCE: 102

Gly His Asn
1

<210> SEQ ID NO 103
<211> LENGTH: 4
<212> TYPE: PRT
<213> ORGANISM: Artificial Sequence
<220> FEATURE:
<223> OTHER INFORMATION: TCR motif

<400> SEQUENCE: 103

Ser Gly His Asn
1

<210> SEQ ID NO 104
<211> LENGTH: 2
<212> TYPE: PRT
<213> ORGANISM: Artificial Sequence
<220> FEATURE:
<223> OTHER INFORMATION: TCR motif

<400> SEQUENCE: 104

Ser Asn
1

<210> SEQ ID NO 105
<211> LENGTH: 7
<212> TYPE: PRT
<213> ORGANISM: Artificial Sequence
<220> FEATURE:

<223> OTHER INFORMATION: TCR motif

<400> SEQUENCE: 105

Ile Phe Ser Asn Met Asp Met
1 5

<210> SEQ ID NO 106
<211> LENGTH: 6
<212> TYPE: PRT
<213> ORGANISM: Artificial Sequence
<220> FEATURE:
<223> OTHER INFORMATION: TCR motif

<400> SEQUENCE: 106

Ile Tyr Ser Asn Gly Asp
1 5

<210> SEQ ID NO 107
<211> LENGTH: 3
<212> TYPE: PRT
<213> ORGANISM: Artificial Sequence
<220> FEATURE:
<223> OTHER INFORMATION: TCR motif

<400> SEQUENCE: 107

Gly Gly Glu
1

<210> SEQ ID NO 108
<211> LENGTH: 7
<212> TYPE: PRT
<213> ORGANISM: Artificial Sequence
<220> FEATURE:
<223> OTHER INFORMATION: TCR motif

<400> SEQUENCE: 108

Val Val Thr Gly Gly Glu Val
1 5

<210> SEQ ID NO 109
<211> LENGTH: 2
<212> TYPE: PRT
<213> ORGANISM: Artificial Sequence
<220> FEATURE:
<223> OTHER INFORMATION: TCR motif

<400> SEQUENCE: 109

Tyr Lys
1

<210> SEQ ID NO 110
<211> LENGTH: 8
<212> TYPE: PRT
<213> ORGANISM: Artificial Sequence
<220> FEATURE:
<223> OTHER INFORMATION: TCR motif

<400> SEQUENCE: 110

Gln Glu Ala Tyr Lys Gln Gln Asn
1 5

<210> SEQ ID NO 111
<211> LENGTH: 3
<212> TYPE: PRT
<213> ORGANISM: Artificial Sequence
<220> FEATURE:
<223> OTHER INFORMATION: TCR motif

<400> SEQUENCE: 111

Gly Glu Glu
1

<210> SEQ ID NO 112
<211> LENGTH: 7
<212> TYPE: PRT
<213> ORGANISM: Artificial Sequence
<220> FEATURE:
<223> OTHER INFORMATION: TCR motif

<400> SEQUENCE: 112

Ser Asn Glu Gly Ser Lys Ala
1               5

<210> SEQ ID NO 113
<211> LENGTH: 6
<212> TYPE: PRT
<213> ORGANISM: Artificial Sequence
<220> FEATURE:
<223> OTHER INFORMATION: TCR motif

<400> SEQUENCE: 113

Phe Asn Asn Asn Val Pro
1               5

<210> SEQ ID NO 114
<211> LENGTH: 6
<212> TYPE: PRT
<213> ORGANISM: Artificial Sequence
<220> FEATURE:
<223> OTHER INFORMATION: TCR motif

<400> SEQUENCE: 114

Ser Tyr Asp Val Lys Met
1               5

<210> SEQ ID NO 115
<211> LENGTH: 6
<212> TYPE: PRT
<213> ORGANISM: Artificial Sequence
<220> FEATURE:
<223> OTHER INFORMATION: TCR motif

<400> SEQUENCE: 115

Ser Met Asn Val Glu Val
1               5

<210> SEQ ID NO 116
<211> LENGTH: 4
<212> TYPE: PRT
<213> ORGANISM: Artificial Sequence
<220> FEATURE:
<223> OTHER INFORMATION: TCR motif
<220> FEATURE:
<221> NAME/KEY: misc_feature
<222> LOCATION: (3)..(3)
<223> OTHER INFORMATION: Xaa can be any naturally occurring amino acid

<400> SEQUENCE: 116

Asp Asn Xaa Gly
1

<210> SEQ ID NO 117
<211> LENGTH: 4
<212> TYPE: PRT

<213> ORGANISM: Artificial Sequence
<220> FEATURE:
<223> OTHER INFORMATION: TCR motif

<400> SEQUENCE: 117

Asp Asn Tyr Gly
1

<210> SEQ ID NO 118
<211> LENGTH: 3
<212> TYPE: PRT
<213> ORGANISM: Artificial Sequence
<220> FEATURE:
<223> OTHER INFORMATION: TCR motif

<400> SEQUENCE: 118

Lys Leu Ile
1

<210> SEQ ID NO 119
<211> LENGTH: 4
<212> TYPE: PRT
<213> ORGANISM: Artificial Sequence
<220> FEATURE:
<223> OTHER INFORMATION: TCR motif
<220> FEATURE:
<221> NAME/KEY: misc_feature
<222> LOCATION: (3)..(3)
<223> OTHER INFORMATION: Xaa can be any naturally occurring amino acid

<400> SEQUENCE: 119

Lys Leu Xaa Phe
1

<210> SEQ ID NO 120
<211> LENGTH: 4
<212> TYPE: PRT
<213> ORGANISM: Artificial Sequence
<220> FEATURE:
<223> OTHER INFORMATION: TCR motif
<220> FEATURE:
<221> NAME/KEY: misc_feature
<222> LOCATION: (3)..(3)
<223> OTHER INFORMATION: Xaa can be any naturally occurring amino acid

<400> SEQUENCE: 120

Lys Leu Xaa Phe
1

<210> SEQ ID NO 121
<211> LENGTH: 4
<212> TYPE: PRT
<213> ORGANISM: Artificial Sequence
<220> FEATURE:
<223> OTHER INFORMATION: TCR motif

<400> SEQUENCE: 121

Lys Leu Ile Phe
1

<210> SEQ ID NO 122
<211> LENGTH: 3
<212> TYPE: PRT
<213> ORGANISM: Artificial Sequence
<220> FEATURE:
<223> OTHER INFORMATION: TCR motif

<400> SEQUENCE: 122

Leu Thr Phe
1

<210> SEQ ID NO 123
<211> LENGTH: 6
<212> TYPE: PRT
<213> ORGANISM: Artificial Sequence
<220> FEATURE:
<223> OTHER INFORMATION: TCR motif

<400> SEQUENCE: 123

Ala Gly Asn Met Leu Thr
1 5

<210> SEQ ID NO 124
<211> LENGTH: 7
<212> TYPE: PRT
<213> ORGANISM: Artificial Sequence
<220> FEATURE:
<223> OTHER INFORMATION: TCR motif

<400> SEQUENCE: 124

Ala Gly Asn Met Leu Thr Phe
1 5

<210> SEQ ID NO 125
<211> LENGTH: 5
<212> TYPE: PRT
<213> ORGANISM: Artificial Sequence
<220> FEATURE:
<223> OTHER INFORMATION: TCR motif

<400> SEQUENCE: 125

Gly Gly Lys Leu Ile
1 5

<210> SEQ ID NO 126
<211> LENGTH: 3
<212> TYPE: PRT
<213> ORGANISM: Artificial Sequence
<220> FEATURE:
<223> OTHER INFORMATION: TCR motif

<400> SEQUENCE: 126

Cys Ala Val
1

<210> SEQ ID NO 127
<211> LENGTH: 4
<212> TYPE: PRT
<213> ORGANISM: Artificial Sequence
<220> FEATURE:
<223> OTHER INFORMATION: TCR motif

<400> SEQUENCE: 127

Cys Ala Val Arg
1

<210> SEQ ID NO 128
<211> LENGTH: 6
<212> TYPE: PRT
<213> ORGANISM: Artificial Sequence
<220> FEATURE:
<223> OTHER INFORMATION: TCR motif
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 128

Asn Xaa Arg Leu Xaa Phe
1 5

<210> SEQ ID NO 129
<211> LENGTH: 6
<212> TYPE: PRT
<213> ORGANISM: Artificial Sequence
<220> FEATURE:
<223> OTHER INFORMATION: TCR motif
<220> FEATURE:
<221> NAME/KEY: misc_feature
<222> LOCATION: (5)..(5)
<223> OTHER INFORMATION: Xaa can be any naturally occurring amino acid

<400> SEQUENCE: 129

Asn Arg Arg Leu Xaa Phe
1 5

<210> SEQ ID NO 130
<211> LENGTH: 6
<212> TYPE: PRT
<213> ORGANISM: Artificial Sequence
<220> FEATURE:
<223> OTHER INFORMATION: TCR motif
<220> FEATURE:
<221> NAME/KEY: misc_feature
<222> LOCATION: (5)..(5)
<223> OTHER INFORMATION: Xaa can be any naturally occurring amino acid

<400> SEQUENCE: 130

Asn Ala Arg Leu Xaa Phe
1 5

<210> SEQ ID NO 131
<211> LENGTH: 6
<212> TYPE: PRT
<213> ORGANISM: Artificial Sequence
<220> FEATURE:
<223> OTHER INFORMATION: TCR motif
<220> FEATURE:
<221> NAME/KEY: misc_feature
<222> LOCATION: (2)..(2)
<223> OTHER INFORMATION: Xaa can be any naturally occurring amino acid

<400> SEQUENCE: 131

Asn Xaa Arg Leu Met Phe
1 5

<210> SEQ ID NO 132
<211> LENGTH: 6
<212> TYPE: PRT
<213> ORGANISM: Artificial Sequence
<220> FEATURE:
<223> OTHER INFORMATION: TCR motif
<220> FEATURE:
<221> NAME/KEY: misc_feature
<222> LOCATION: (2)..(2)
<223> OTHER INFORMATION: Xaa can be any naturally occurring amino acid

<400> SEQUENCE: 132

Asn Xaa Arg Leu Ala Phe
1 5

<210> SEQ ID NO 133
<211> LENGTH: 5
<212> TYPE: PRT
<213> ORGANISM: Artificial Sequence
<220> FEATURE:
<223> OTHER INFORMATION: TCR motif

<400> SEQUENCE: 133

Asn Gln Pro Gln His
1               5

<210> SEQ ID NO 134
<211> LENGTH: 3
<212> TYPE: PRT
<213> ORGANISM: Artificial Sequence
<220> FEATURE:
<223> OTHER INFORMATION: TCR motif

<400> SEQUENCE: 134

Ala Ser Ser
1

<210> SEQ ID NO 135
<211> LENGTH: 4
<212> TYPE: PRT
<213> ORGANISM: Artificial Sequence
<220> FEATURE:
<223> OTHER INFORMATION: TCR motif

<400> SEQUENCE: 135

Ala Ser Ser Leu
1

<210> SEQ ID NO 136
<211> LENGTH: 4
<212> TYPE: PRT
<213> ORGANISM: Artificial Sequence
<220> FEATURE:
<223> OTHER INFORMATION: TCR motif

<400> SEQUENCE: 136

Ala Ser Ser Ser
1

<210> SEQ ID NO 137
<211> LENGTH: 4
<212> TYPE: PRT
<213> ORGANISM: Artificial Sequence
<220> FEATURE:
<223> OTHER INFORMATION: TCR motif

<400> SEQUENCE: 137

Cys Ala Ser Ser
1

<210> SEQ ID NO 138
<211> LENGTH: 5
<212> TYPE: PRT
<213> ORGANISM: Artificial Sequence
<220> FEATURE:
<223> OTHER INFORMATION: TCR motif

<400> SEQUENCE: 138

Cys Ala Ser Ser Leu
1               5

<210> SEQ ID NO 139

<211> LENGTH: 4
<212> TYPE: PRT
<213> ORGANISM: Artificial Sequence
<220> FEATURE:
<223> OTHER INFORMATION: TCR motif

<400> SEQUENCE: 139

Glu Gln Phe Phe
1

<210> SEQ ID NO 140
<211> LENGTH: 6
<212> TYPE: PRT
<213> ORGANISM: Artificial Sequence
<220> FEATURE:
<223> OTHER INFORMATION: TCR motif

<400> SEQUENCE: 140

Gly Asn Gln Pro Gln His
1 5

<210> SEQ ID NO 141
<211> LENGTH: 3
<212> TYPE: PRT
<213> ORGANISM: Artificial Sequence
<220> FEATURE:
<223> OTHER INFORMATION: TCR motif

<400> SEQUENCE: 141

Gln Tyr Phe
1

<210> SEQ ID NO 142
<211> LENGTH: 2
<212> TYPE: PRT
<213> ORGANISM: Artificial Sequence
<220> FEATURE:
<223> OTHER INFORMATION: TCR motif

<400> SEQUENCE: 142

Glu Gln
1

<210> SEQ ID NO 143
<211> LENGTH: 4
<212> TYPE: PRT
<213> ORGANISM: Artificial Sequence
<220> FEATURE:
<223> OTHER INFORMATION: TCR motif

<400> SEQUENCE: 143

Glu Gln Tyr Phe
1

<210> SEQ ID NO 144
<211> LENGTH: 5
<212> TYPE: PRT
<213> ORGANISM: Artificial Sequence
<220> FEATURE:
<223> OTHER INFORMATION: TCR motif

<400> SEQUENCE: 144

Tyr Glu Gln Tyr Phe
1 5

<210> SEQ ID NO 145
<211> LENGTH: 3

<212> TYPE: PRT
<213> ORGANISM: Artificial Sequence
<220> FEATURE:
<223> OTHER INFORMATION: TCR motif

<400> SEQUENCE: 145

Glu Gln Phe
1

<210> SEQ ID NO 146
<211> LENGTH: 4
<212> TYPE: PRT
<213> ORGANISM: Artificial Sequence
<220> FEATURE:
<223> OTHER INFORMATION: TCR motif

<400> SEQUENCE: 146

Asn Glu Gln Phe
1

<210> SEQ ID NO 147
<211> LENGTH: 5
<212> TYPE: PRT
<213> ORGANISM: Artificial Sequence
<220> FEATURE:
<223> OTHER INFORMATION: TCR motif

<400> SEQUENCE: 147

Asn Glu Gln Phe Phe
1               5

<210> SEQ ID NO 148
<211> LENGTH: 3
<212> TYPE: PRT
<213> ORGANISM: Artificial Sequence
<220> FEATURE:
<223> OTHER INFORMATION: TCR motif

<400> SEQUENCE: 148

Glu Gln Tyr
1

<210> SEQ ID NO 149
<211> LENGTH: 4
<212> TYPE: PRT
<213> ORGANISM: Artificial Sequence
<220> FEATURE:
<223> OTHER INFORMATION: TCR motif

<400> SEQUENCE: 149

Tyr Glu Gln Tyr
1

<210> SEQ ID NO 150
<211> LENGTH: 4
<212> TYPE: PRT
<213> ORGANISM: Artificial Sequence
<220> FEATURE:
<223> OTHER INFORMATION: TCR motif

<400> SEQUENCE: 150

Gly Tyr Thr Phe
1

<210> SEQ ID NO 151
<211> LENGTH: 13
<212> TYPE: PRT

```
<213> ORGANISM: Artificial Sequence
<220> FEATURE:
<223> OTHER INFORMATION: TCR CDR3a

<400> SEQUENCE: 151

Cys Ala Glu Ser Thr Gly Gly Ser Tyr Ile Pro Thr Phe
1               5                   10


<210> SEQ ID NO 152
<211> LENGTH: 14
<212> TYPE: PRT
<213> ORGANISM: Artificial Sequence
<220> FEATURE:
<223> OTHER INFORMATION: TCR CDR3a

<400> SEQUENCE: 152

Cys Ala Val Asn Ala Pro Gly Gly Tyr Asn Lys Leu Ile Phe
1               5                   10


<210> SEQ ID NO 153
<211> LENGTH: 15
<212> TYPE: PRT
<213> ORGANISM: Artificial Sequence
<220> FEATURE:
<223> OTHER INFORMATION: TCR CDR3a

<400> SEQUENCE: 153

Cys Ala Val Glu Arg Pro Thr Gly Gly Tyr Asn Lys Leu Ile Phe
1               5                   10                  15


<210> SEQ ID NO 154
<211> LENGTH: 12
<212> TYPE: PRT
<213> ORGANISM: Artificial Sequence
<220> FEATURE:
<223> OTHER INFORMATION: TCR CDR3a

<400> SEQUENCE: 154

Cys Ala Val Glu Asp Tyr Gly Gln Asn Phe Val Phe
1               5                   10


<210> SEQ ID NO 155
<211> LENGTH: 15
<212> TYPE: PRT
<213> ORGANISM: Artificial Sequence
<220> FEATURE:
<223> OTHER INFORMATION: TCR CDR3a

<400> SEQUENCE: 155

Cys Ala Leu Ser Asp Ser Ser Gly Gly Ser Tyr Ile Pro Thr Phe
1               5                   10                  15


<210> SEQ ID NO 156
<211> LENGTH: 12
<212> TYPE: PRT
<213> ORGANISM: Artificial Sequence
<220> FEATURE:
<223> OTHER INFORMATION: TCR CDR3a

<400> SEQUENCE: 156

Cys Ala Ala Cys Tyr Ser Gly Tyr Ala Leu Asn Phe
1               5                   10


<210> SEQ ID NO 157
<211> LENGTH: 12
<212> TYPE: PRT
<213> ORGANISM: Artificial Sequence
```

<220> FEATURE:
<223> OTHER INFORMATION: TCR CDR3a

<400> SEQUENCE: 157

Cys Ala Val Val Thr Asn Asp Tyr Lys Leu Ser Phe
1 5 10

<210> SEQ ID NO 158
<211> LENGTH: 15
<212> TYPE: PRT
<213> ORGANISM: Artificial Sequence
<220> FEATURE:
<223> OTHER INFORMATION: TCR CDR3a

<400> SEQUENCE: 158

Cys Ala Met Arg Ser Phe Ala Gln Ala Gly Thr Ala Leu Ile Phe
1 5 10 15

<210> SEQ ID NO 159
<211> LENGTH: 15
<212> TYPE: PRT
<213> ORGANISM: Artificial Sequence
<220> FEATURE:
<223> OTHER INFORMATION: TCR CDR3a

<400> SEQUENCE: 159

Cys Ala Gly Trp Ile Ser Pro Gln Gly Ala Gln Lys Leu Val Phe
1 5 10 15

<210> SEQ ID NO 160
<211> LENGTH: 14
<212> TYPE: PRT
<213> ORGANISM: Artificial Sequence
<220> FEATURE:
<223> OTHER INFORMATION: TCR CDR3b

<400> SEQUENCE: 160

Cys Ala Ser Ala Ser Asp Ser Asp Asp Glu Lys Leu Phe Phe
1 5 10

<210> SEQ ID NO 161
<211> LENGTH: 14
<212> TYPE: PRT
<213> ORGANISM: Artificial Sequence
<220> FEATURE:
<223> OTHER INFORMATION: TCR CDR3b

<400> SEQUENCE: 161

Cys Ala Ser Ser Ile Ser Gln Gly Gly Tyr Gly Tyr Thr Phe
1 5 10

<210> SEQ ID NO 162
<211> LENGTH: 13
<212> TYPE: PRT
<213> ORGANISM: Artificial Sequence
<220> FEATURE:
<223> OTHER INFORMATION: TCR CDR3b

<400> SEQUENCE: 162

Cys Ala Ser Ser Pro Gly Thr Asp Tyr Glu Gln Tyr Phe
1 5 10

<210> SEQ ID NO 163
<211> LENGTH: 16
<212> TYPE: PRT
<213> ORGANISM: Artificial Sequence
<220> FEATURE:

<223> OTHER INFORMATION: TCR CDR3b

<400> SEQUENCE: 163

Cys Ser Ala Arg Asp Leu Ser Gly Arg Ser Leu Asp Thr Gln Tyr Phe
1 5 10 15

<210> SEQ ID NO 164
<211> LENGTH: 15
<212> TYPE: PRT
<213> ORGANISM: Artificial Sequence
<220> FEATURE:
<223> OTHER INFORMATION: TCR CDR3b

<400> SEQUENCE: 164

Cys Ala Ser Ser Leu Gly Arg Gln Thr Asn Thr Glu Ala Phe Phe
1 5 10 15

<210> SEQ ID NO 165
<211> LENGTH: 15
<212> TYPE: PRT
<213> ORGANISM: Artificial Sequence
<220> FEATURE:
<223> OTHER INFORMATION: TCR CDR3b

<400> SEQUENCE: 165

Cys Ala Ser Ser Tyr Arg Pro Lys Leu Asp Thr Glu Ala Phe Phe
1 5 10 15

<210> SEQ ID NO 166
<211> LENGTH: 16
<212> TYPE: PRT
<213> ORGANISM: Artificial Sequence
<220> FEATURE:
<223> OTHER INFORMATION: TCR CDR3b

<400> SEQUENCE: 166

Cys Ala Ser Ser Gln Asp Leu Gly Gln Gly Ser Asp Thr Gln Tyr Phe
1 5 10 15

<210> SEQ ID NO 167
<211> LENGTH: 18
<212> TYPE: PRT
<213> ORGANISM: Artificial Sequence
<220> FEATURE:
<223> OTHER INFORMATION: TCR CDR3b

<400> SEQUENCE: 167

Cys Ala Ser Ser Gln Arg Gly Lys Gly Gln Gly Asp Glu Glu Thr Gln
1 5 10 15

Tyr Phe

<210> SEQ ID NO 168
<211> LENGTH: 13
<212> TYPE: PRT
<213> ORGANISM: Artificial Sequence
<220> FEATURE:
<223> OTHER INFORMATION: TCR CDR3b

<400> SEQUENCE: 168

Cys Ala Ser Ser Leu Ser Thr Asn Thr Glu Ala Phe Phe
1 5 10

<210> SEQ ID NO 169
<211> LENGTH: 8
<212> TYPE: PRT
<213> ORGANISM: Artificial Sequence
<220> FEATURE:
<223> OTHER INFORMATION: TCR CDR2a

<400> SEQUENCE: 169

Tyr Phe Ser Gly Asp Pro Leu Val
1 5

<210> SEQ ID NO 170
<211> LENGTH: 7
<212> TYPE: PRT
<213> ORGANISM: Artificial Sequence
<220> FEATURE:
<223> OTHER INFORMATION: TCR CDR2a

<400> SEQUENCE: 170

Ile Gln Ser Ser Gln Arg Glu
1 5

<210> SEQ ID NO 171
<211> LENGTH: 8
<212> TYPE: PRT
<213> ORGANISM: Artificial Sequence
<220> FEATURE:
<223> OTHER INFORMATION: TCR CDR2a

<400> SEQUENCE: 171

Arg Asn Ser Phe Asp Glu Gln Asn
1 5

<210> SEQ ID NO 172
<211> LENGTH: 7
<212> TYPE: PRT
<213> ORGANISM: Artificial Sequence
<220> FEATURE:
<223> OTHER INFORMATION: TCR CDR2a

<400> SEQUENCE: 172

Ile Arg Ser Asn Val Gly Glu
1 5

<210> SEQ ID NO 173
<211> LENGTH: 8
<212> TYPE: PRT
<213> ORGANISM: Artificial Sequence
<220> FEATURE:
<223> OTHER INFORMATION: TCR CDR2a

<400> SEQUENCE: 173

Gln Gly Ser Tyr Asp Glu Gln Asn
1 5

<210> SEQ ID NO 174
<211> LENGTH: 7
<212> TYPE: PRT
<213> ORGANISM: Artificial Sequence
<220> FEATURE:
<223> OTHER INFORMATION: TCR CDR2a

<400> SEQUENCE: 174

Leu Val Lys Ser Gly Glu Val
1 5

<210> SEQ ID NO 175
<211> LENGTH: 6
<212> TYPE: PRT
<213> ORGANISM: Artificial Sequence
<220> FEATURE:

<223> OTHER INFORMATION: TCR CDR2b

<400> SEQUENCE: 175

Phe Tyr Asn Asn Glu Ile
1 5

<210> SEQ ID NO 176
<211> LENGTH: 6
<212> TYPE: PRT
<213> ORGANISM: Artificial Sequence
<220> FEATURE:
<223> OTHER INFORMATION: TCR CDR2b

<400> SEQUENCE: 176

Tyr Phe Ser Glu Thr Gln
1 5

<210> SEQ ID NO 177
<211> LENGTH: 6
<212> TYPE: PRT
<213> ORGANISM: Artificial Sequence
<220> FEATURE:
<223> OTHER INFORMATION: TCR CDR2b

<400> SEQUENCE: 177

Ser Val Gly Ala Gly Ile
1 5

<210> SEQ ID NO 178
<211> LENGTH: 6
<212> TYPE: PRT
<213> ORGANISM: Artificial Sequence
<220> FEATURE:
<223> OTHER INFORMATION: TCR CDR2b

<400> SEQUENCE: 178

Tyr Asn Asn Lys Glu Leu
1 5

<210> SEQ ID NO 179
<211> LENGTH: 3
<212> TYPE: PRT
<213> ORGANISM: Artificial Sequence
<220> FEATURE:
<223> OTHER INFORMATION: TCR motif

<400> SEQUENCE: 179

Phe Gln Asn
1

<210> SEQ ID NO 180
<211> LENGTH: 6
<212> TYPE: PRT
<213> ORGANISM: Artificial Sequence
<220> FEATURE:
<223> OTHER INFORMATION: TCR CDR2b

<400> SEQUENCE: 180

Phe Asn Tyr Glu Ala Gln
1 5

<210> SEQ ID NO 181
<211> LENGTH: 6
<212> TYPE: PRT
<213> ORGANISM: Artificial Sequence
<220> FEATURE:
<223> OTHER INFORMATION: TCR CDR1a

<400> SEQUENCE: 181

Tyr Gly Gly Thr Val Asn
1               5

<210> SEQ ID NO 182
<211> LENGTH: 6
<212> TYPE: PRT
<213> ORGANISM: Artificial Sequence
<220> FEATURE:
<223> OTHER INFORMATION: TCR CDR1a

<400> SEQUENCE: 182

Asp Ser Ala Ile Tyr Asn
1               5

<210> SEQ ID NO 183
<211> LENGTH: 7
<212> TYPE: PRT
<213> ORGANISM: Artificial Sequence
<220> FEATURE:
<223> OTHER INFORMATION: TCR CDR1a

<400> SEQUENCE: 183

Thr Arg Asp Thr Thr Tyr Tyr
1               5

<210> SEQ ID NO 184
<211> LENGTH: 6
<212> TYPE: PRT
<213> ORGANISM: Artificial Sequence
<220> FEATURE:
<223> OTHER INFORMATION: TCR CDR1a

<400> SEQUENCE: 184

Asp Ser Ala Ser Asn Tyr
1               5

<210> SEQ ID NO 185
<211> LENGTH: 7
<212> TYPE: PRT
<213> ORGANISM: Artificial Sequence
<220> FEATURE:
<223> OTHER INFORMATION: TCR CDR1a

<400> SEQUENCE: 185

Thr Ser Asp Gln Ser Tyr Gly
1               5

<210> SEQ ID NO 186
<211> LENGTH: 5
<212> TYPE: PRT
<213> ORGANISM: Artificial Sequence
<220> FEATURE:
<223> OTHER INFORMATION: TCR CDR1a

<400> SEQUENCE: 186

Thr Thr Leu Ser Asn
1               5

<210> SEQ ID NO 187
<211> LENGTH: 5
<212> TYPE: PRT
<213> ORGANISM: Artificial Sequence
<220> FEATURE:
<223> OTHER INFORMATION: TCR CDR1b

<400> SEQUENCE: 187

Ser Asn His Leu Tyr
1 5

<210> SEQ ID NO 188
<211> LENGTH: 5
<212> TYPE: PRT
<213> ORGANISM: Artificial Sequence
<220> FEATURE:
<223> OTHER INFORMATION: TCR CDR1b

<400> SEQUENCE: 188

Ser Gly His Arg Ser
1 5

<210> SEQ ID NO 189
<211> LENGTH: 5
<212> TYPE: PRT
<213> ORGANISM: Artificial Sequence
<220> FEATURE:
<223> OTHER INFORMATION: TCR CDR1b

<400> SEQUENCE: 189

Ser Glu His Asn Arg
1 5

<210> SEQ ID NO 190
<211> LENGTH: 5
<212> TYPE: PRT
<213> ORGANISM: Artificial Sequence
<220> FEATURE:
<223> OTHER INFORMATION: TCR CDR1b

<400> SEQUENCE: 190

Leu Gly His Asp Thr
1 5

<210> SEQ ID NO 191
<211> LENGTH: 5
<212> TYPE: PRT
<213> ORGANISM: Artificial Sequence
<220> FEATURE:
<223> OTHER INFORMATION: TCR CDR1b

<400> SEQUENCE: 191

Ser Ser His Ala Thr
1 5

<210> SEQ ID NO 192
<211> LENGTH: 5
<212> TYPE: PRT
<213> ORGANISM: Artificial Sequence
<220> FEATURE:
<223> OTHER INFORMATION: TCR motif

<400> SEQUENCE: 192

Thr Glu Ala Phe Phe
1 5

<210> SEQ ID NO 193
<211> LENGTH: 3
<212> TYPE: PRT
<213> ORGANISM: Artificial Sequence
<220> FEATURE:
<223> OTHER INFORMATION: TCR motif

<400> SEQUENCE: 193

-continued

```
Gly Gly Ser
1
```